(12) United States Patent
Bicknell et al.

(10) Patent No.: US 8,394,381 B2
(45) Date of Patent: Mar. 12, 2013

(54) ANTIBODIES, POLYPEPTIDES AND USES THEREOF

(75) Inventors: Roy Bicknell, Oxford (GB); Steven Suchting, Oxford (GB); Lorna Mary Dyet Stewart, London (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 11/429,147

(22) Filed: May 5, 2006

(65) Prior Publication Data
US 2006/0263369 A1    Nov. 23, 2006

(30) Foreign Application Priority Data

Nov. 20, 2002 (GB) .................................. 0227080.9
Sep. 12, 2003 (GB) .................................. 0321401.2

(51) Int. Cl.
*A61K 39/395* (2006.01)
(52) U.S. Cl. .................................................. 424/155.1
(58) Field of Classification Search ................ 424/155.1
See application file for complete search history.

(56) References Cited

U.S. PATENT DOCUMENTS

| | | | |
|---|---|---|---|
| 6,069,007 A | 5/2000 | Rossi et al. | |
| 6,225,118 B1 | 5/2001 | Grant et al. | |
| 7,163,797 B2 | 1/2007 | Ruben et al. | |
| 7,582,440 B2 | 9/2009 | Bicknell et al. | |
| 7,740,830 B2 | 6/2010 | Bicknell et al. | |
| 2003/0072736 A1 | 4/2003 | Baker et al. | |
| 2003/0236210 A1* | 12/2003 | Geng ............................... | 514/44 |
| 2004/0071711 A1 | 4/2004 | Bicknell et al. | |
| 2006/0099143 A1 | 5/2006 | Bicknell et al. | |
| 2007/0025913 A1 | 2/2007 | Bicknell et al. | |
| 2008/0019963 A1 | 1/2008 | Bicknell et al. | |
| 2008/0145359 A1 | 6/2008 | Bicknell et al. | |
| 2008/0166295 A1 | 7/2008 | Bicknell et al. | |
| 2008/0219924 A1 | 9/2008 | Bicknell et al. | |
| 2009/0191572 A1 | 7/2009 | Bicknell et al. | |

FOREIGN PATENT DOCUMENTS

| | | |
|---|---|---|
| EP | 0682113 | 11/1995 |
| EP | 1074617 | 2/2001 |
| WO | WO 95/26364 A1 | 10/1995 |
| WO | WO-99/06423 | 2/1999 |
| WO | WO-99/11293 | 3/1999 |
| WO | WO-99/46281 | 9/1999 |
| WO | WO-99/53051 | 10/1999 |
| WO | WO-00/53756 | 9/2000 |
| WO | WO-01/23523 | 4/2001 |
| WO | WO 02/36771 * | 5/2002 |
| WO | WO-02/36771 | 5/2002 |
| WO | WO 2004/003163 A2 | 1/2004 |
| WO | WO 2004/046191 A2 | 6/2004 |

OTHER PUBLICATIONS

Park et al. (Dev. Biol. 261:251-267 (2003)).*
Rudikoff et al (Proc Natl Acad Sci USA 1982 vol. 79 p. 1979-1983).*
Casset et al. (2003) BBRC 307, 198-205.*
Vajdos et al. (2002) 320, 415-428.*
Holm et al (2007) 44, 1075-1084.*
Trachsel et al. (Adv. Drug•Deliv. Rev. 58:735-754 (2006).*
Jain Scientific American Jul. 1994, 58-65.*
Chatterjee et al Cancer Immunol. Imunother., 1994, 75-80.*
Dermer Biotechnology 12: 320, 1994.*
Gura et al (Science vol. 278 Nov. 1997 1041-1042.*
Seaver (1994; Genetic Engineering vol. 14(14):10 and 21).*
Miller et al. (AntiCancer Res. 17:3299-3306 (1997)).*
Abbas et al. Cellular & Molec. Biol. 1994, pp. 41-43.*
Asano et al. (Cancer Res. 55:5296-5301 (1995).*
Maier et al. (Anti-Cancer Drugs 8:238-244 (1997).*
Genbank Accession No. BB536291 (2001).
Genbank Accession No. AAL31867 (2001).
Genbank Accession No. AC011562 (2001).
Genbank Accession No. Q9NWJ8 (2000).
Genbank Accession No. AK000805 (2000).
Genbank Accession No. AF361473 (2001).
Genbank Accession No. AK025195 (2000).
[No Author Listed] BD BioCoat TM Angiogenesis System— Endothelial Cell Migration; available as Catalog No. 354143 from BD Biosciences, Bedford, MA (2002).
[No Author Listed] AngioKit Protocol, Catalogue No. ZHA-1000, by TCS CellWorks Ltd, Buckingham MK18 2LR, UK.
Aaronson et al., Toward the development of a gene index to the human genome: an assessment of the nature of high-throughput EST sequence data. Genome Res. Sep. 1996;6(9):829-45.
Adams et al., Initial assessment of human gene diversity and expression patterns based upon 83 million nucleotides of cDNA sequence. Nature. Sep. 28, 1995;377(6547 Suppl):3-174.
Adams et al., Roles of ephrinB ligands and EphB receptors in cardiovascular development: demarcation of arterial/venous domains, vascular morphogenesis, and sprouting angiogenesis. Genes Dev. Feb. 1, 1999;13(3):295-306.
Aiello et al., Suppression of retinal neovascularization in vivo by inhibition of vascular endothelial growth factor (VEGF) using soluble VEGF-receptor chimeric proteins. Proc Natl Acad Sci U S A. Nov. 7, 1995;92(23):10457-61.

(Continued)

*Primary Examiner* — Lynn Bristol
(74) *Attorney, Agent, or Firm* — Wolf, Greenfield & Sacks, P.C.

(57) ABSTRACT

A method of inhibiting angiogenesis in an individual in need thereof comprising administering an antibody that selectively binds to the extracellular region of human magic roundabout (MR) to the individual. An antibody that has the amino acid sequences i) to iii), the amino acid sequences iv) to vi), or the amino acid sequences i) to vi). i) S A S S S V S Y M Y ii) L T S N L A S iii) Q Q W S S N P L T iv) D Y N L N v) V I N P N Y G T T S Y N Q K F K G vi) G R D Y F G Y. A method of inhibiting angiogenesis in an individual in need thereof comprising administering the extracellular domain (residues 1-467) of MR, or a fragment thereof that inhibits angiogenesis, to the individual. A method of inhibiting endothelial cell migration and/or proliferation comprising administering the extracellular domain of MR, or a fragment thereof that inhibits endothelial cell migration and/or proliferation.

13 Claims, 15 Drawing Sheets

OTHER PUBLICATIONS

Banerji et al., LYVE-1, a new homologue of the CD44 glycoprotein, is a lymph-specific receptor for hyaluronan. J Cell Biol. Feb. 22, 1999;144(4):789-801.

Bashaw et al., Repulsive axon guidance: Abelson and Enabled play opposing roles downstream of the roundabout receptor. Cell. Jun. 23, 2000;101(7):703-15.

Bashaw et al., Chimeric axon guidance receptors: the cytoplasmic domains of slit and netrin receptors specify attraction versus repulsion. Cell. Jun. 25, 1999;97(7):917-26.

Bates et al., Identification and analysis of a novel member of the ubiquitin family expressed in dendritic cells and mature B cells. Eur J Immunol. Oct. 1997;27(10):2471-7.

Bernstein et al., Characterization of a human fovea cDNA library and regional differential gene expression in the human retina. Genomics. Mar. 15, 1996;32(3):301-8.

Bortoluzzi et al., The human adult skeletal muscle transcriptional profile reconstructed by a novel computational approach. Genome Res. Mar. 2000;10(3):344-9.

Boyle et al., DNA immunization: induction of higher avidity antibody and effect of route on T cell cytotoxicity. Proc Natl Acad Sci U S A. Dec. 23, 1997;94(26):14626-31.

Brose et al., Slit proteins bind Robo receptors and have an evolutionarily conserved role in repulsive axon guidance. Cell. Mar. 19, 1999;96(6):795-806.

Chen et al., Characterization of gene expression in resting and activated mast cells. J Exp Med. Nov. 2, 1998;188(9):1657-68.

Clark et al., Localization of VEGF and expression of its receptors flt and KDR in human placenta throughout pregnancy. Hum Reprod. May 1996;11(5):1090-8.

Cole et al., The genetics of cancer—a 3D model. Nat Genet. Jan. 1999;21(1 Suppl):38-41.

Compton, Nucleic acid sequence-based amplification. Nature. Mar. 7, 1997;350(6313):91-2.

Cross et al., FGF and VEGF function in angiogenesis: signalling pathways, biological responses and therapeutic inhibition. Trends Pharmacol Sci. Apr. 2001;22(4):201-7.

Cserzo et al., Prediction of transmembrane alpha-helices in prokaryotic membrane proteins: the dense alignment surface method. Protein Eng. Jun. 1997;10(6):673-6.

Cwirla et al., Peptides on phage: a vast library of peptides for identifying ligands. Proc Natl Acad Sci U S A. Aug. 1990;87(16):6378-82.

Dillon et al., Functional gene expression domains: defining the functional unit of eukaryotic gene regulation. Bioessays. Jul. 2000;22(7):657-65.

Felbor et al., Genomic organization and chromosomal localization of the interphotoreceptor matrix proteoglycan-1 (IMPG1) gene: a candidate for 6q-linked retinopathies. Cytogenet Cell Genet. 1998;81(1)12-7.

Fong et al., Role of the Flt-1 receptor tyrosine kinase in regulating the assembly of vascular endothelium. Nature. Jul. 6, 1995;376(6535):66-70.

Gerhold et al., It's the genes! EST access to human genome content. Bioessays. Dec. 1996;18(12):973-81.

Ginsburg et al., Human von Willebrand factor (vWF): isolation of complementary DNA (cDNA) clones and chromosomal localization. Science. Jun. 21, 1985;228(4706):1401-6.

Goetze et al., Leptin induces endothelial cell migration through Akt, which is inhibited by PPARgamma-ligands. Hypertension. Nov. 2002;40(5):748-54.

Hayward et al., An autosomal dominant, qualitative platelet disorder associated with multimerin deficiency, abnormalities in platelet factor V, thrombospondin, von Willebrand factor, and fibrinogen and an epinephrine aggregation defect. Blood. Jun. 15, 1996;87(12):4967-78.

Hayward et al., Multimerin is found in the alpha-granules of resting platelets and is synthesized by a megakaryocytic cell line. J Clin Invest. Jun. 1993;91(6):2630-9.

Hayward et al., Studies of multimerin in human endothelial cells. Blood. Feb. 15, 1998;91(4):1304-17.

Hockel et al., Tumor hypoxia: definitions and current clinical, biologic, and molecular aspects. J Natl Cancer Inst. Feb. 21, 2001;93(4):266-76.

Hori et al., Differential effects of angiostatic steroids and dexamethasone on angiogenesis and cytokine levels in rat sponge implants. Br J Pharmacol. Aug. 1996;118(7):1584-91.

Huminiecki et al., In silico cloning of novel endothelial-specific genes. Genome Res. Nov. 2000;10(11):1796-806.

Huminiecki et al., Magic roundabout is a new member of the roundabout receptor family that is endothelial specific and expressed at sites of active angiogenesis. Genomics. Apr. 2002;79(4):547-52.

Itoh et al., Expression profile of active genes in granulocytes. Blood. Aug. 15, 1998;92(4):1432-41.

Kettleborough et al., Humanization of a mouse monoclonal antibody by CDR-grafting: the importance of framework residues on loop conformation. Protein Eng. Oct. 1991;4(7):773-83.

Kidd et al., Roundabout controls axon crossing of the CNS midline and defines a novel subfamily of evolutionarily conserved guidance receptors. Cell. Jan. 23, 1998;92(2):205-15.

Landis et al., The measurement of observer agreement for categorical data. Biometrics. Mar. 1977; 33(1):159-74.

Li et al., Vertebrate slit, a secreted ligand for the transmembrane protein roundabout, is a repellent for olfactory bulb axons. Cell. Mar. 19, 1999;96(6):807-18.

Matthews et al., A receptor tyrosihe kinase cDNA isolated from a population of enriched primitive hematopoietic cells and exhibiting close genetic linkage to c-kit. Proc Natl Acad Sci U S A. Oct. 15, 1991;88(20):9026-30.

Maxwell et al., The tumour suppressor protein VHL targets hypoxia-inducible factors for oxygen-dependent proteolysis. Nature. May 20, 1999;399(6733):271-5.

Nichols et al., Identification of human megakaryocyte coagulation factor V. Blood. Jun. 1985;65(6):1396-406.

Nielsen et al., Identification of prokaryotic and eukaryotic signal peptides and prediction of their cleavage sites. Protein Eng. Jan. 1997;10(1):1-6.

Obermair et al., Vascular endothelial growth factor and its receptors in male fertility. Fertil Steril. Aug. 1999;72(2):269-75.

Park et al., Robo4 is a vascular-specific receptor that inhibits endothelial migration. Dev Biol. Sep. 1, 2003;261(1):251-67.

Partanen et al., A novel endothelial cell surface receptor tyrosine kinase with extracellular epidermal growth factor homology domains. Mol Cell Biol. Apr. 1992;12(4):1698-707.

Petrenko et al., The molecular characterization of the fetal stem cell marker AA4. Immunity. Jun. 1999;10(6):691-700.

Rupnick et al., Adipose tissue mass can be regulated through the vasculature. Proc Natl Acad Sci U S A. Aug. 6, 2002;99(16):10730-5.

Sato et al., Tie-1 and tie-2 define another class of putative receptor tyrosine kinase genes expressed in early embryonic vascular system. Proc Natl Acad Sci U S A. Oct. 15, 1993;90(20):9355-8.

Sato et al., Distinct roles of the receptor tyrosine kinases Tie-1 and Tie-2 in blood vessel formation. Nature. Jul. 6, 1995;376(6535):70-4.

Schuler, Pieces of the puzzle: expressed sequence tags and the catalog of human genes. J Mol Med. Oct. 1997;75(10):694-8.

Shalaby et al., Failure of blood-island formation and vasculogenesis in Flk-1-deficient mice. Nature. Jul. 6, 1995;376(6535):62-6.

Shibuya et al., Nucleotide sequence and expression of a novel human receptor-type tyrosine kinase gene (flt) closely related to the fms family. Oncogene. Apr. 1990;5(4):519-24.

Sierra-Honigmann et al., Biological action of leptin as an angiogenic factor. Science. Sep. 11, 1998;281(5383):1683-6.

Soker et al., Neuropilin-1 is expressed by endothelial and tumor cells as an isoform-specific receptor for vascular endothelial growth factor. Cell. Mar. 20, 1998;92(6):735-45.

Sporn et al., Biosynthesis of von Willebrand protein by human megakaryocytes. J Clin Invest. Sep. 1985;76(3):1102-6.

Strausberg et al., New opportunities for uncovering the molecular basis of cancer. Nat Genet. Apr. 15, 1997 Spec No. 415-6.

Suda et al., Hematopoiesis and angiogenesis. Int J Hematol. Feb. 2000;71(2):99-107.

Tamura et al., cDNA cloning and gene expression of human type Ialpha cGMP-dependent protein kinase. Hypertension. Mar 1996;27(3 Pt 2):552-7.

Vasmatzis et al., Discovery of three genes specifically expressed in human prostate by expressed sequence tag database analysis. Proc Natl Acad Sci U S A. Jan. 6, 1998;95(1):300-4.

Velculescu et al., Serial analysis of gene expression. Science. Oct. 20, 1995;270(5235):484-7.

Verhoeyen et al., Reshaping human antibodies: grafting an antilysozyme activity. Science. Mar. 25, 1988;239(4847):1534-6.

Vikkula et al., Vascular dysmorphogenesis caused by an activating mutation in the receptor tyrosine kinase TIE2. Cell. Dec. 27, 1996;87(7):1181-90.

Von Heijne et al., Membrane protein structure prediction. Hydrophobicity analysis and the positive-inside rule. J Mol Biol. May 20, 1992;225(2):487-94.

Welle et al., Inventory of high-abundance mRNAs in skeletal muscle of normal men. Genome Res. May 1999;9(5):506-13.

Ziegler et al., KDR receptor: a key marker defining hematopoietic stem cells. Science. Sep. 3, 1999;285(5433):1553-8.

Legg et al., Slits and Roundabouts in cancer, tumour angiogenesis and endothelial cell migration. Angiogenesis. 2008;11(1):13-21. Epub Feb. 9, 2008.

Gariano, R.F. et al., "Retinal angiogenesis in development and disease," *Nature* Dec. 15, 2005; 438:960-966.

Khurana, R. et al., "Role of Angiogenesis in Cardiovascular Disease: A Critical Appraisal," *Circulation* 2005; 112:1813-1824.

Amalfitano et al., "Separating fact from fiction: assessing the potential of modified adenovirus vectors for use in human gene therapy." *Current Gene Therapy* 2002, 2:111-133.

Bechard et al., "Characterization of the secreted form of endothelial-cell-specific molecule 1 by specific monoclonal antibodies." *Journal of Vascular Research* (2000) 37:417-425.

Carmeliet et al., "Angiogenesis in cancer and other diseases." *Naure* (2000) 407:249-257.

Dorai et al., "Development of a hammerhead ribozyme against BCL-2. II. Ribozyme treatment sensitizes hormone-resistant prostate cancer cells to apoptotic agents." *Anticancer Res.*, (1997) vol. 17, 3307-12.

Dobrzanski et al., "Antiangiogenic and antitumor efficacy of EphA2 receptor antagonist", *Cancer Research*, (Feb. 1, 2004) vol. 64, 910-919.

Hagedorn et al., "A short peptide domain of platelet factor 4 blocks angiogenic key events induced by FGF-2[1]", *The FASEB Journal*, (Mar. 2001) vol. 15, 550-552.

Hortsch, "The L1 family of neural cell adhesion molecules: old proteins performing new tricks." *Neuron* 17, 587-593.

Huminiecki et al, "In Silico cloning of novel endothelial specific genes: Their role in Angiogenesis." *Angiogenesis*. 2001 S7:220-221.

Jain, "Tumor angiogenesis and accessibility: role of vascular endothelial growth factor", *Seminars in Oncology*, (Dec. 2002) vol. 29, No. 6, Suppl. 16, 3-9.

Kuwano et al., "Angiogenesis factors." *Internal medicine* (2001) vol. 40, No. 7, pp. 565-572.

Lassalle et al., "ESM-1 is a novel human endothelial cell-specific molecule expressed in lung and regulated by cytokines."*J. Biol. Chem.* 1996, 271(34):20458-20464.

Min et al., "Capsaicin inhibits in Vitro and in Vivo angiogenesis", *Cancer Research*, (Jan. 15, 2004) vol. 64, 644-651.

Ruggeri et al., "CEP-7055: A novel, orally active pan inhibitor of vascular endothelial growth factor receptor tyrosine kinases with potent antiangiogenic activity and antitumor efficacy in preclinical models[1]", *Cancer Research*, (Sep. 15, 2003) vol. 63, 5978-5991.

Skolnick et al., "From genes to protein structure and function: novel applications of computational approaches in the genomic era." *Trends in Biotech* 2000, 18(1):34-39.

Smith et al., "Angiogenesis, vascular endothelial growth factor and the endometrium." *Human Reproduction Update* 1998 vol. 4, No. 5 pp. 509-519.

Stein et al., "Antisense oligonucleotides as therapeutic agents—is the bullet really magical?" *Science* 1993, 261:1004-1012.

Sun et al., "Blocking angiogenesis and tumorigenesis with GFA-116, a synthetic molecule that inhibits binding of vascular endothelial growth factor to its receptor", *Cancer Research*, (May 15, 2004) vol. 64, 3586-3592.

Van Der Schaft et al., "The designer antiangiogenic peptide anginex targets tumor endothelial cells and inhibits tumor growth in animal models", *The FASEB Journal*, (Oct. 18, 2002).

Verma, et al., "Gene therapy—promises, problems and prospects." *Nature* 1997, 389:239-242.

Beckman et al., Antibody constructs in cancer therapy: protein engineering strategies to improve exposure in solid tumors. Cancer. Jan. 15, 2007;109(2):170-9.

Cespedes et al., Mouse models in oncogenesis and cancer therapy. Clin Transl Oncol. May 2006;8(5):318-29.

Dennis, Cancer: off by a whisker. Nature. Aug. 17, 2006;442(7104):739-41.

Fujimori et al., A modeling analysis of monoclonal antibody percolation through tumors: a binding-site barrier. J Nucl Med. Jul. 1990;31(7):1191-8.

Rudnick et al., Affinity and avidity in antibody-based tumor targeting. Cancer Biother Radiopharm. Apr. 2009;24(2):155-61.

Sheldon et al., Active involvement of Robo1 and Robo4 in filopodia formation and endothelial cell motility mediated via WASP and other actin nucleation-promoting factors. FASEB J. Feb. 2009;23(2):513-22.

Suchting et al., Soluble Robo4 receptor inhibits in vivo angiogenesis and endothelial cell migration. FASEB J. Jan. 2005;19(1):121-3.

Talmadge et al., Murine models to evaluate novel and conventional therapeutic strategies for cancer. Am J Pathol. Mar. 2007;170(3):793-804.

Thurber et al., Antibody tumor penetration: transport opposed by systemic and antigen-mediated clearance. Adv Drug Deliv Rev. Sep. 2008;60(12):1421-34. Epub Apr. 24, 2008.

Voskoglou-Nomikos et al., Clinical predictive value of the in vitro cell line, human xenograft, and mouse allograft preclinical cancer models. Clin Cancer Res. Sep. 15, 2003;9(11):4227-39.

Fuchs et al., Species specificity of anti-acetylcholine receptor antibodies elicited by synthetic peptides. Biochemistry. Jul. 28, 1987;26(15):4611-6.

Görn et al., Serum levels of Magic Roundabout protein in patients with advanced non-small cell lung cancer (NSCLC). Lung Cancer. Jul. 2005;49(1):71-6.

Oshima et al., Generation of species-specific antihemoglobin antibodies by immunization with synthetic peptides of human hemoglobin. Protein Chem. Dec. 1989;8(6):767-78.

Rankin et al., Regulation of left-right patterning in mice by growth/differentiation factor-1. Nat Genet. Mar. 2000;24(3):262-5.

Sipos et al., Cloning and sequencing of the genes coding for the 10- and 60-kDa heat shock proteins from *Pseudomonas aeruginosa* and mapping of a species-specific epitope. Infect Immun. Sep. 1991;59(9):3219-26.

[No Author] Recombinant Mouse EphA2/Fc Chimera. R & D Systems, Catalog No. 639-A2. Lot No. BCB08. Mar. 31, 2005.

Auerbach et al., Angiogenesis assays: problems and pitfalls. Cancer Metastasis Rev. 2000;19(1-2):167-72. Review.

Bohlen et al., Chapter 24: Vascular Endothelial Growth Factor Receptor: Antibodies for Anti-Angiogenesis Therapy. Tumor Angiogenesis: Basic Mechanisms and Cancer Therapy. Dieter Marmé and Norbert Fusenig, eds. Published by Springer, 2007: 425-452. ISBN 354033176X, 9783540331766.

Freshney et al., Culture of Animal Cells. A Manual of Basic Technique. Alan R. Liss, Inc. 1983; New York: 3-4.

Staton et al., Current methods for assaying angiogenesis in vitro and in vivo. Int J Exp Pathol. Oct. 2004;85(5):233-48. Review.

Tockman et al., Considerations in bringing a cancer biomarker to clinical application. Cancer Res. May 1, 1992;52(9 Suppl):2711s-2718s. Review.

Trikha et al., CNTO 95, a fully human monoclonal antibody that inhibits alphav integrins, has antitumor and antiangiogenic activity in vivo. Int J Cancer. Jun. 20, 2004;110(3):326-35.

West et al., Chapter 11: Three-Dimensional in Vitro Angiogenesis in the Rat Aortic Ring Model. Methods in Molecular Biology, Angiogenesis Protocols. S. Martin and C. Murray, eds. $2^{nd}$ Ed: 467:189-210. Humana Press, 2009.

Notice of Opposition to EP Patent 1 565 491; dated Dec. 29, 2010.

Declaration of Dr. Yoshitaka Isumi, together with his Curriculum Vitae and Experimental Results, signed Dec. 22, 2010.

Ducancel et al., Recombinant colorimetric antibodies: construction and characterization of a bifunctional F(ab)2/alkaline phosphatase conjugate produced in *Escherichia coli*. Biotechnology (NY). May 1993;11(5):601-5.

Ducancel et al., Recombinant colorimetric antibodies: genetic construction and production from *E. coli*. C R Acad Sci III. 1992;315(6):221-4. French.

Weiss et al., Application of an alkaline phosphatase fusion protein system suitable for efficient screening and production of Fab-enzyme conjugates in *Escherichia coli*. J Biotechnol. Mar. 15, 1994;33(1):43-53.

\* cited by examiner

FIG. 1A

NotI site

```
GCGGCCGCGAATTCGGCACGAGCAGCAGGACAAAGTGCTCGGGACAAGGACATAG
GGCTGAGAGTAGCCATGGGCTCTGGAGGAGACAGCCTCCTGGGGGGCAGGGGTTC
CCTGCCTCTGCTGCTCCTGCTCATCATGGGAGGCATGGCTCAGGACTCCCCGCCC
CAGATCCTAGTCCACCCCCAGGACCAGCTGTTCCAGGGCCCTGGCCCTGCCAGGA
TGAGCTGCCAAGCCTCAGGCCAGCCACCTCCCACCATCCGCTGGTTGCTGAATGG
GCAGCCCTGAGCATGGTGCCCCAGACCCACACCACCTCCTGCCTGATGGGACC
CTTCTGCTGCTACAGCCCCCTGCCCGGGGACATGCCCACGATGGCCAGGCCCTGT
CCACAGACCTGGGTGTCTACACATGTGAGGCCAGCAACCGGCTTGGCACGGCAGT
CAGCAGAGGCGCTCGGCTGTCTGTGGCTGTCCTCCGGGAGGATTTCCAGATCCAG
CCTCGGGACATGGTGGCTGTGGTGGGTGAGCAGTTTACTCTGGAATGTGGGCCGC
CCTGGGGCCACCCAGAGCCCACAGTCTCATGGTGGAAAGATGGGAAACCCCTGGC
CCTCCAGCCCGGAAGGCACACAGTGTCCGGGGGTCCCTGCTGATGGCAAGAGCA
GAGAAGAGTGACGAAGGGACCTACATGTGTGTGGCCACCAACAGCGCAGGACATA
GGGAGAGCCGCGCAGCCCGGGTTTCCATCCAGGAGCCCCAGGACTACACGGAGCC
TGTGGAGCTTCTGGCTGTGCGAATTCAGCTGGAAAATGTGACACTGCTGAACCCG
GATCCTGCAGAGGGCCCCAAGCCTAGACCGGCGGTGTGGCTCAGCTGGAAGGTCA
GTGGCCCTGCTGCGCCTGCCCAATCTTACACGGCCTTGTTCAGGACCCAGACTGC
CCCGGGAGGCCAGGGAGCTCCGTGGGCAGAGGAGCTGCTGGCCGGCTGGCAGAGC
GCAGAGCTTGGAGGCCTCCACTGGGGCCAAGACTACGAGTTCAAAGTGAGACCAT
CCTCTGGCCGGGCTCGAGGCCCTGACAGCAACGTGCTGCTCCTGAGGCTGCCGGA
AAAAGTGCCCAGTGCCCCACCTCAGGAAGTGACTCTAAAGCCTGGCAATGGCACT
GTCTTTGTGAGCTGGGTCCCACCACCTGCTGAAAACCACAATGGCATCATCCGTG
GCTACCAGGTCTGGAGCCTGGGCAACACATCACTGCCACCAGCCAACTGGACTGT
AGTTGGTGAGCAGACCCAGCTGGAAATCGCCACCCATATGCCAGGCTCCTACTGC
GTGCAAGTGGCTGCAGTCACTGGTGCTGGAGCTGGGGAGCCCAGTAGACCTGTCT
GCCTCCTTTTAGAGCAGGCCATGGAGCGAGCCACCCAAGAACCCAGTGAGCATGG
TCCCTGGACCCTGGAGCAGCTGAGGGCTACCTTGAAGCGGCCTGAGGTCATTGCC
ACCTGCGGTGTTGCACTCTGGCTGCTGCTTCTGGGCACCGCCGTGTGTATCCACC
GCCGGCGCCGAGCTAGGGTGCACCTGGGCCCAGGTCTGTACAGATATACCAGTGA
GGATGCCATCCTAAAACACAGGATGGATCACAGTGACTCCCAGTGGTTGGCAGAC
ACTTGGCGTTCCACCTCTGGCTCTCGGGACCTGAGCAGCAGCAGCAGCCTCAGCA
GTCGGCTGGGGGCGGATGCCCGGGACCCACTAGACTGTCGTCGCTCCTTGCTCTC
CTGGGACTCCCGAAGCCCCGGCGTGCCCCTGCTTCCAGACACCAGCACTTTTTAT
GGCTCCCTCATCGCTGAGCTGCCCTCCAGTACCCCAGCCAGGCCAAGTCCCCAGG
TCCCAGCTGTCAGGCGCCTCCCACCCCAGCTGGCCCAGCTCTCCAGCCCCTGTTC
```

FIG. 1B

```
CAGCTCAGACAGCCTCTGCAGCCGCAGGGGACTCTCTTCTCCCCGCTTGTCTCTG
GCCCCTGCAGAGGCTTGGAAGGCCAAAAAGAAGCAGGAGCTGCAGCATGCCAACA
GTTCCCCACTGCTCCGGGGCAGCCACTCCTTGGAGCTCCGGGCCTGTGAGTTAGG
AAATAGAGGTTCCAAGAACCTTTCCCAAAGCCCAGGAGCTGTGCCCCAAGCTCTG
GTTGCCTGGCGGGCCCTGGGACCGAAACTCCTCAGCTCCTCAAATGAGCTGGTTA
CTCGTCATCTCCCTCCAGCACCCTCTTTCCTCATGAAACTCCCCCAACTCAGAG
TCAACAGACCCAGCCTCCGGTGGCACCACAGGCTCCCTCCTCCATCCTGCTGCCA
GCAGCCCCATCCCCATCCTTAGCCCTGCAGTCCCCTAGCCCCAGGCCTCTT
CCCTCTCTGGCCCCAGCCCAGCTTCCAGTCGCCTGTCCAGCTCCTCACTGTCATC
CCTGGGGGAGGATCAAGACAGCGTGCTGACCCCTGAGGAGGTAGCCCTGTGCTTG
GAACTCAGTGAGGGTGAGGAGACTCCCAGGAACAGCGTCTCTCCCATGCCAAGGG
CTCCTTCACCCCCCACCACCTATGGGTACATCAGCGTCCCAACAGCCTCAGAGTT
CACGGACATGGGCAGGACTGGAGGAGGGTGGGGCCCAAGGGGGAGTCTTGCTG
TGCCCACCTCGGCCCTGCCTCACCCCCACCCCAGCGAGGGCTCCTTAGCCAATG
GTTGGGGCTCAGCCTCTGAGGACAATGCCGCCAGCGCCAGAGCCAGCCTTGTCAG
CTCCTCCGATGGCTCCTTCCTCGCTGATGCTCACTTTGCCCGGGCCCTGGCAGTG
GCTGTGGATAGCTTTGGTTTCGGTCTAGAGCCCAGGGAGGCAGACTGCGTCTTCA
TAGATGCCTCATCACCTCCCTCCCCACGGGATGAGATCTTCCTGACCCCCAACCT
CTCCCTGCCCCTGTGGGAGTGGAGGCCAGACTGGTTGGAAGACATGGAGGTCAGC
CACACCCAGCGGCTGGGAAGGGGATGCCTCCCTGGCCCCCTGACTCTCAGATCT
CTTCCCAGAGAAGTCAGCTCCACTGTCGTATGCCCAAGGCTGGTGCTTCTCCTGT
AGATTACTCCTGAACCGTGTCCCTGAGACTTCCCAGACGGGAATCAGAACCACTT
CTCCTGTCCACCCACAAGACCTGGGCTGTGGTGTGTGGGTCTTGGCCTGTGTTTC
TCTGCAGCTGGGGTCCACCTTCCCAAGCCTCCAGAGAGTTCTCCCTCCACGATTG
TGAAAACAAATGAAAACAAAATTAGAGCAAAGCTGACCTGGAGCCCTCAGGGAGC
AAAACATCATCTCCACCTGACTCCTAGCCACTGCTTTCTCCTCTGTGCCATCCAC
TCCCACCACCAGGTTGTTTTGGCCTGAGGAGCAGCCCTGCCTGCTGCTCTTCCCC
CACCATTTGGATCACAGGAAGTGGAGGAGCCAGAGGTGCCTTTGTGGAGGACAGC
AGTGGCTGCTGGGAGAGGGCTGTGGAGGAAGGAGCTTCTCGGAGCCCCCTCTCAG
CCTTACCTGGGCCCCTCCTCTAGAGAAGAGCTCAACTCTCTCCCAACCTCACCAT
GGAAGAAAATAATTATGAATGCCACTGAGGCACTGAGGCCCTACCTCATGCCAA
ACAAAGGGTTCAAGGCTGGGTCTAGCGAGGATGCTGAAGGAAGGGAGGTATGAGA
CCGTAGGTCAAAAGCACCATCCTCGTACTGTTGTCACTATGAGCTTAAGAAATTT
GATACCATAAAATGGTAAAGACTTGAAAAAAAAAAAAAAAAAAAAAAAAAAAAA
AAAAAAAAAAAAAAAAAAAAAAAAAAAAAAAAAAAAAAAAAAAAAAAAAAAAA
AAAAAAAAAAAAAAAAAAA
```

NotI site downstream of polyA tail

FIG. 1C

```
   1 MGSGGDSLLG GRGSLPLLLL LIMGGMAQDS PPQILVHPQD QLFQGPGPAR
  51 MSCQASGQPP PTIRWLLNGQ PLSMVPPDPH HLLPDGTLLL LQPPARGHAH
 101 DGQALSTDLG VYTCEASNRL GTAVSRGARL SVAVLREDFQ IQPRDMVAVV
 151 GEQFTLECGP PWGHPEPTVS WWKDGKPLAL QPGRHTVSGG SLLMARAEKS
 201 DEGTYMCVAT NSAGHRESRA ARVSIQEPQD YTEPVELLAV RIQLENVTLL
 251 NPDPAEGPKP RPAVWLSWKV SGPAAPAQSY TALFRTQTAP GGQGAPWAEE
 301 LLAGWQSAEL GGLHWGQDYE FKVRPSSGRA RGPDSNVLLL RLPEKVPSAP
 351 PQEVTLKPGN GTVFVSWVPP PAENHNGIIR GYQVWSLGNT SLPPANWTVV
 401 GEQTQLEIAT HMPGSYCVQV AAVTGAGAGE PSRPVCLLLE QAMERATQEP
 451 SEHGPWTLEQ LRATLKRPEV IATCGVALWL LLLGTAVCIH RRRRARVHLG
 501 PGLYRYTSED AILKHRMDHS DSQWLADTWR STSGSRDLSS SSSLSSRLGA
 551 DARDPLDCRR SLLSWDSRSP GVPLLPDTST FYGSLIAELP SSTPARPSPQ
 601 VPAVRRLPPQ LAQLSSPCSS SDSLCSRRGL SSPRLSLAPA EAWKAKKKQE
 651 LQHANSSPLL RGSHSLELRA CELGNRGSKN LSQSPGAVPQ ALVAWRALGP
 701 KLLSSSNELV TRHLPPAPLF PHETPPTQSQ QTQPPVAPQA PSSILLPAAP
 751 IPILSPCSPP SPQASSLSGP SPASSRLSSS SLSSLGEDQD SVLTPEEVAL
 801 CLELSEGEET PRNSVSPMPR APSPPTTYGY ISVPTASEFT DMGRTGGGVG
 851 PKGGVLLCPP RPCLTPTPSE GSLANGWGSA SEDNAASARA SLVSSSDGSF
 901 LADAHFARAL AVAVDSFGFG LEPREADCVF IDASSPPSPR DEIFLTPNLS
 951 LPLWEWRPDW LEDMEVSHTQ RLGRGMPPWP PDSQISSQRS QLHCRMPKAG
1001 ASPVDYS
```

Figure 2A

HinDIII site

AAGCTTAAAGTGCTCGGGACAAGGACATAGGGCTGAGAGTAGCCATGGGCTCTGG
AGGAGACAGCCTCCTGGGGGGCAGGGGTTCCCTGCCTCTGCTGCTCCTGCTCATC
ATGGGAGGCATGGCTCAGGACTCCCCGCCCCAGATCCTAGTCCACCCCCAGGACC
AGCTGTTCCAGGGCCCTGGCCCTGCCAGGATGAGCTGCCAAGCCTCAGGCCAGCC
ACCTCCCACCATCCGCTGGTTGCTGAATGGGCAGCCCCTGAGCATGGTGCCCCCA
GACCCACACCACCTCCTGCCTGATGGGACCCTTCTGCTGCTACAGCCCCCTGCCC
GGGGACATGCCCACGATGGCCAGGCCCTGTCCACAGACCTGGGTGTCTACACATG
TGAGGCCAGCAACCGGCTTGGCACGGCAGTCAGCAGAGGCGCTCGGCTGTCTGTG
GCTGTCCTCCGGGAGGATTTCCAGATCCAGCCTCGGGACATGGTGGCTGTGGTGG
GTGAGCAGTTTACTCTGGAATGTGGGCCGCCCTGGGGCCACCCAGAGCCCACAGT
CTCATGGTGGAAAGATGGGAAACCCCTGGCCCTCCAGCCCGGAAGGCACACAGTG
TCCGGGGGTCCCTGCTGATGGCAAGAGCAGAGAAGAGTGACGAAGGGACCTACA
TGTGTGTGGCCACCAACAGCGCAGGACATAGGGAGAGCCGCGCAGCCCGGGTTTC
CATCCAGGAGCCCCAGGACTACACGGAGCCTGTGGAGCTTCTGGCTGTGCGAATT
CAGCTGGAAAATGTGACACTGCTGAACCCGGATCCTGCAGAGGGCCCCAAGCCTA
GACCGGCGGTGTGGCTCAGCTGGAAGGTCAGTGGCCCTGCTGCGCCTGCCCAATC
TTACACGGCCTTGTTCAGGACCCAGACTGCCCCGGGAGGCCAGGGAGCTCCGTGG
GCAGAGGAGCTGCTGGCCGGCTGGCAGAGCGCAGAGCTTGGAGGCCTCCACTGGG
GCCAAGACTACGAGTTCAAAGTGAGACCATCCTCTGGCCGGGCTCGAGGCCCTGA
CAGCAACGTGCTGCTCCTGAGGCTGCCGGAAAAAGTGCCCAGTGCCCCACCTCAG
GAAGTGACTCTAAAGCCTGGCAATGGCACTGTCTTTGTGAGCTGGGTCCCACCAC
CTGCTGAAAACCACAATGGCATCATCCGTGGCTACCAGGTCTGGAGCCTGGGCAA
CACATCACTGCCACCAGCCAACTGGACTGTAGTTGGTGAGCAGACCCAGCTGGAA
ATCGCCACCCATATGCCAGGCTCCTACTGCGTGCAAGTGGCTGCAGTCACTGGTG
CTGGAGCTGGGGAGCCCAGTAGACCTGTCTGCCTCCTTTTAGAGCAGGCCATGGA
GCGAGCCACCCAAGAACCCAGTGAGCATGGTCCCTGGACCCTGGAGCAGCTGAGG
GCTACCTTGAAGCGGTAGTAAGCGGCCGC (STOP,STOP NotI Site)

Figure 2B

MGSGGDSLLGGRGSLPLLLLLIMGGMAQDSPPQILVHPQDQLFQGPGPARMSCQA
SGQPPPTIRWLLNGQPLSMVPPDPHHLLPDGTLLLLQPPARGHAHDGQALSTDLG
VYTCEASNRLGTAVSRGARLSVAVLREDFQIQPRDMVAVVGEQFTLECGPPWGHP
EPTVSWWKDGKPLALQPGRHTVSGGSLLMARAEKSDEGTYMCVATNSAGHRESRA
ARVSIQEPQDYTEPVELLAVRIQLENVTLLNPDPAEGPKPRPAVWLSWKVSGPAA
PAQSYTALFRTQTAPGGQGAPWAEELLAGWQSAELGGLHWGQDYEFKVRPSSGRA
RGPDSNVLLLRLPEKVPSAPPQEVTLKPGNGTVFVSWVPPPAENHNGIIRGYQVW
SLGNTSLPPANWTVVGEQTQLEIATHMPGSYCVQVAAVTGAGAGEPSRPVCLLLE
QAMERATQEPSEHGPWTLEQLRATLKR

Figure 3

PGPARMSCQASGQPPPTIRWLLNGQPLSMVPPDPHHLLPDGTLLLLQPPARGHAH
DGQALSTDLGVYTCEASNRLGTAVSRGARLSVAVLREDFQIQPRDMVAVVGEQFT
LECGPPWGHPEPTVSWWKDGKPLALQPGRHTVSGGSLLMARAEKSDEGTYMCVA

Figure 4A

PGPARMSCQASGQPPPTIRWLLNGQPLSMVPPDPHHLLPDGTLLLLQPPARGHAH
DGQALSTDLGVYTCEA

Figure 4B

GEQFTLECGPPWGHPEPTVSWWKDGKPLALQPGRHTVSGGSLLMARAEKSDEGTY
MCVA

| Treatment | Average | Variance |
| --- | --- | --- |
| Control | 2.77 | 0.18 |
| 100 ug/ml MR-7 | 1.04 | 0.43 |
| 100 ug/ml MR-Ecto | 0.74 | 0.34 |

| Treatment | Mean | Standard Deviation |
|---|---|---|
| Control | 2.91489 | 0.1579 |
| Human IgG | 3.42857 | 0.409303 |
| MR ectodomain | 0.632258 | 0.194497 |

FIG. 7A Untreated
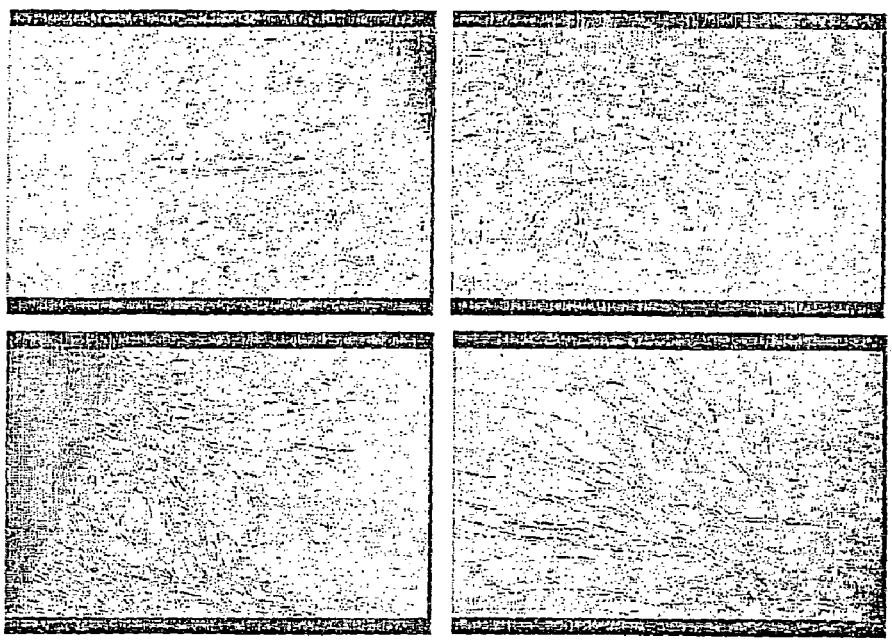
FIG. 7B 100 µg/ml MR-7 Ab
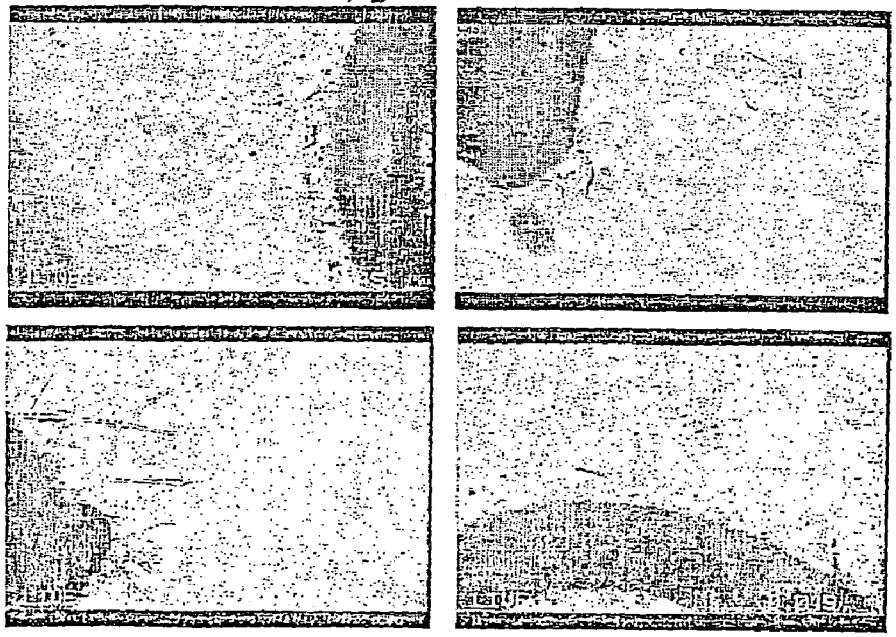

FIG. 7C 15 µg/ml MR Ectodomain
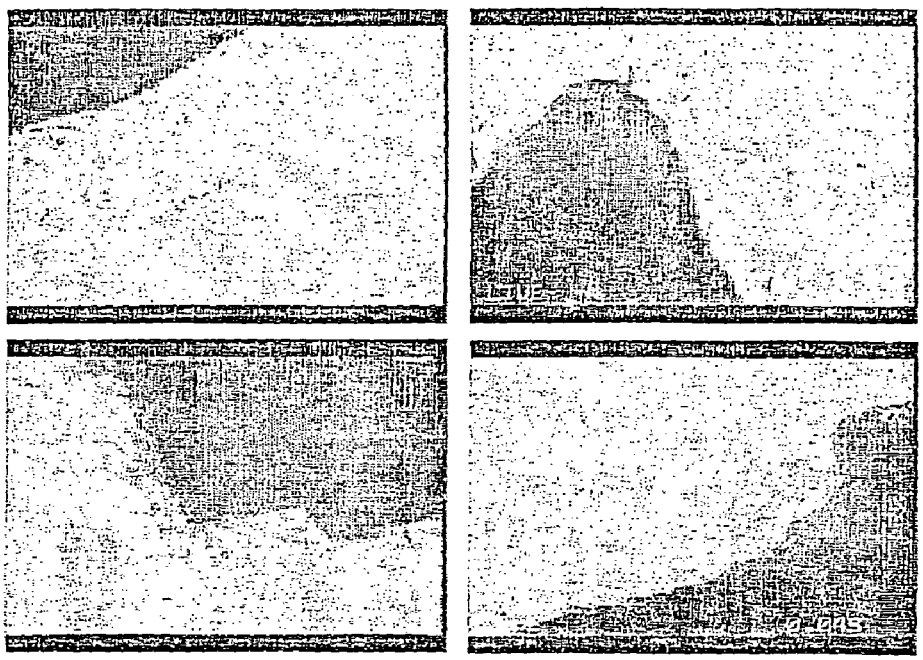

| Group | Mean | Standard deviation |
|---|---|---|
| bFGF | 57.63 | 19.01 |
| bFGF + MR ectodomain | 21.5 | 10.89 |

| Treatment | Mean | Standard Deviation |
|---|---|---|
| Control | 60.5 | 10.41 |
| VEGF | 131.33 | 29.70 |
| VEGF + MR ectodomain | 21.67 | 4.04 |

| Treatment | Mean | Standard deviation |
|---|---|---|
| Control | 66.33 | 10.41 |
| BFGF | 152.00 | 27.62 |
| bFGF + MR ectodomain | 21.67 | 1.53 |

| Treatment | Average of Replicates | Standard Deviation |
|---|---|---|
| Control | 1957 | 57 |
| 100 µg/ml Robo4-Fc | 683 | 73 |
| 50 µg/ml Robo4-Fc | 1122 | 92 |
| 25 µg/ml Robo4-Fc | 1401 | 134 |
| 12.5 µg/ml Robo4-Fc | 1483 | 54 |
| 6.25 µg/ml Robo4-Fc | 1991 | 596 |
| 100 µg/ml Human IgG | 2015 | 93 |

ID NO: 1). FIG. 1C shows

SEQUENCE LISTING

```
<160> NUMBER OF SEQ ID NOS: 46

<210> SEQ ID NO 1
<211> LENGTH: 3870
<212> TYPE: DNA
<213> ORGANISM: Homo sapiens

<400> SEQUENCE: 1
gcggccgcga attcggcacg agcagcagga caaagtgctc gggacaagga catagggctg      60
agagtagcca tgggctctgg aggagacagc ctcctggggg gcaggggttc cctgcctctg     120
ctgctcctgc tcatcatggg aggcatggct caggactccc cgcccagat cctagtccac      180 ccccaggacc agctgttcca gggccctggc cctgccagga tgagctgcca agcctcaggc     240
cagccacctc ccaccatccg ctggttgctg aatgggcagc cctgagcat ggtgccccca      300 gacccacacc acctcctgcc tgatgggacc cttctgctgc tacagccccc tgcccgggga     360
catgcccacg atggccaggc cctgtccaca gacctgggtg tctacacatg tgaggccagc     420
aaccggcttg gcacggcagt cagcagaggc gctcggctgt ctgtggctgt cctccgggag     480
gatttccaga tccagcctcg ggacatggtg gctgtggtgg gtgagcagtt tactctggaa     540
tgtgggccgc cctggggcca cccagagccc acagtctcat ggtggaaaga tgggaaaccc     600
ctggccctcc agcccggaag gcacacagtg tccgggggt ccctgctgat ggcaagagca      660
gagaagagtg acgaagggac ctacatgtgt gtggccacca acagcgcagg acatagggag     720
agccgcgcag cccgggtttc catccaggag ccccaggact cacggagcc tgtggagctt      780 ctggctgtgc gaattcagct ggaaaatgtg acactgctga acccggatcc tgcagagggc     840
cccaagccta gaccggcggt gtggctcagc tggaaggtca gtggccctgc tgcgcctgcc      900
caatcttaca cggccttgtt caggacccag actgccccgg gaggccaggg agctccgtgg     960
gcagaggagc tgctggccgg ctggcagagc gcagagcttg gaggcctcca ctggggccaa    1020
gactacgagt tcaaagtgag accatcctct ggccgggctc gaggccctga cagcaacgtg    1080
ctgctcctga ggctgccgga aaaagtgccc agtgccccac ctcaggaagt gactctaaag    1140
cctggcaatg gcactgtctt tgtgagctgg gtcccaccac ctgctgaaaa ccacaatggc    1200
atcatccgtg gctaccaggt ctggagcctg ggcaacacat cactgccacc agccaactgg    1260
actgtagttg gtgagcagac ccagctggaa atcgccaccc atatgccagg ctcctactgc    1320
gtgcaagtgg ctgcagtcac tggtgctgga ctggggagc ccagtagacc tgtctgcctc    1380
cttttagagc aggccatgga gcgagccacc caagaaccca gtgagcatgg tcctggacc    1440
```

```
ctggagcagc tgagggctac cttgaagcgg cctgaggtca ttgccacctg cggtgttgca    1500
ctctggctgc tgcttctggg caccgccgtg tgtatccacc gccggcgccg agctagggtg    1560
cacctgggcc caggtctgta cagatatacc agtgaggatg ccatcctaaa acacaggatg    1620
gatcacagtg actcccagtg gttggcagac acttggcgtt ccacctctgg ctctcgggac    1680
ctgagcagca gcagcagcct cagcagtcgg ctggggcgg atgcccggga cccactagac    1740
tgtcgtcgct ccttgctctc ctgggactcc cgaagcccg gcgtgcccct gcttccagac    1800
accagcactt tttatggctc cctcatcgct gagctgccct ccagtacccc agccaggcca    1860
agtccccagg tcccagctgt caggcgcctc ccaccccagc tggcccagct ctccagcccc    1920
tgttccagct cagacagcct ctgcagccgc aggggactct cttctccccg cttgtctctg    1980
gcccctgcag aggcttggaa ggccaaaaag aagcaggagc tgcagcatgc caacagttcc    2040
ccactgctcc ggggcagcca ctccttggag ctccgggcct gtgagttagg aaatagaggt    2100
tccaagaacc tttcccaaag cccaggagct gtgcccaag ctctggttgc ctggcgggcc    2160
ctgggaccga aactcctcag ctcctcaaat gagctggtta ctcgtcatct ccctccagca    2220
cccctctttc ctcatgaaac tcccccaact cagagtcaac agaccagcc tccggtggca    2280 ccacaggctc cctcctccat cctgctgcca gcagccccca tcccatcct tagcccctgc    2340 agtccccta gcccccaggc ctcttccctc tctggcccca gcccagcttc cagtcgcctg    2400
tccagctcct cactgtcatc cctggggag atcaagaca gcgtgctgac ccctgaggag    2460
gtagccctgt gcttggaact cagtgagggt gaggagactc ccaggaacag cgtctctccc    2520
atgccaaggg ctccttcacc ccccaccacc tatgggtaca tcagcgtccc aacagcctca    2580
gagttcacgg acatgggcag gactggagga ggggtggggc ccaagggggg agtcttgctg    2640
tgcccacctc ggccctgcct cacccccacc cccagcgagg gctccttagc caatggttgg    2700
ggctcagcct ctgaggacaa tgccgccagc gccagagcca gccttgtcag ctcctccgat    2760
ggctccttcc tcgctgatgc tcactttgcc cgggccctgg cagtggctgt ggatagcttt    2820
ggtttcggtc tagagcccag ggaggcagac tgcgtcttca tagatgcctc atcacctccc    2880
tccccacggg atgagatctt cctgaccccc aactctcccc tgcccctgtg ggagtggagg    2940
ccagactggt tggaagacat ggaggtcagc cacacccagc ggctgggaag ggggatgcct    3000
ccctggcccc ctgactctca gatctcttcc cagagaagtc agctccactg tcgtatgccc    3060
aaggctggtg cttctcctgt agattactcc tgaaccgtgt ccctgagact tcccagacgg    3120
gaatcagaac cacttctcct gtccacccac aagacctggg ctgtggtgtg tgggtcttgg    3180
cctgtgtttc tctgcagctg gggtccacct tcccaagcct ccagagagtt ctccctccac    3240
gattgtgaaa acaaatgaaa acaaaattag agcaaagctg acctggagcc ctcagggagc    3300
aaaacatcat ctcccacctga ctcctagcca ctgctttctc ctctgtgcca tccactccca    3360
ccaccaggtt gttttggcct gaggagcagc cctgcctgct gctcttcccc caccatttgg    3420
atcacaggaa gtggaggagc cagaggtgcc tttgtggagg acagcagtgg ctgctgggag    3480
agggctgtgg aggaaggagc ttctcggagc cccctctcag ccttacctgg gcccctcctc    3540
tagagaagag ctcaactctc tcccaacctc accatggaaa gaaaataatt atgaatgcca    3600
ctgaggcact gaggccctac ctcatgccaa acaagggtt caaggctggg tctagcgagg    3660
atgctgaagg aagggaggta tgagaccgta ggtcaaaagc accatcctcg tactgttgtc    3720
actatgagct taagaaattt gataccataa aatggtaaag acttgaaaaa aaaaaaaaaa    3780
```

-continued

```
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa                                     3870

<210> SEQ ID NO 2
<211> LENGTH: 1007
<212> TYPE: PRT
<213> ORGANISM: Homo sapiens

<400> SEQUENCE: 2

Met Gly Ser Gly Gly Asp Ser Leu Leu Gly Arg Gly Ser Leu Pro
1               5                   10                  15

Leu Leu Leu Leu Leu Ile Met Gly Gly Met Ala Gln Asp Ser Pro Pro
                20                  25                  30

Gln Ile Leu Val His Pro Gln Asp Gln Leu Phe Gln Gly Pro Gly Pro
        35                  40                  45

Ala Arg Met Ser Cys Gln Ala Ser Gly Gln Pro Pro Pro Thr Ile Arg
    50                  55                  60

Trp Leu Leu Asn Gly Gln Pro Leu Ser Met Val Pro Pro Asp Pro His
65                  70                  75                  80

His Leu Leu Pro Asp Gly Thr Leu Leu Leu Gln Pro Pro Ala Arg
                85                  90                  95

Gly His Ala His Asp Gly Gln Ala Leu Ser Thr Asp Leu Gly Val Tyr
            100                 105                 110

Thr Cys Glu Ala Ser Asn Arg Leu Gly Thr Ala Val Ser Arg Gly Ala
        115                 120                 125

Arg Leu Ser Val Ala Val Leu Arg Glu Asp Phe Gln Ile Gln Pro Arg
    130                 135                 140

Asp Met Val Ala Val Gly Glu Gln Phe Thr Leu Glu Cys Gly Pro
145                 150                 155                 160

Pro Trp Gly His Pro Glu Pro Thr Val Ser Trp Trp Lys Asp Gly Lys
                165                 170                 175

Pro Leu Ala Leu Gln Pro Gly Arg His Thr Val Ser Gly Gly Ser Leu
            180                 185                 190

Leu Met Ala Arg Ala Glu Lys Ser Asp Glu Gly Thr Tyr Met Cys Val
        195                 200                 205

Ala Thr Asn Ser Ala Gly His Arg Glu Ser Arg Ala Ala Arg Val Ser
    210                 215                 220

Ile Gln Glu Pro Gln Asp Tyr Thr Glu Pro Val Glu Leu Leu Ala Val
225                 230                 235                 240

Arg Ile Gln Leu Glu Asn Val Thr Leu Leu Asn Pro Asp Pro Ala Glu
                245                 250                 255

Gly Pro Lys Pro Arg Pro Ala Val Trp Leu Ser Trp Lys Val Ser Gly
            260                 265                 270

Pro Ala Ala Pro Ala Gln Ser Tyr Thr Ala Leu Phe Arg Thr Gln Thr
        275                 280                 285

Ala Pro Gly Gly Gln Gly Ala Pro Trp Ala Glu Leu Leu Ala Gly
    290                 295                 300

Trp Gln Ser Ala Glu Leu Gly Gly Leu His Trp Gly Gln Asp Tyr Glu
305                 310                 315                 320

Phe Lys Val Arg Pro Ser Ser Gly Arg Ala Arg Gly Pro Asp Ser Asn
                325                 330                 335

Val Leu Leu Leu Arg Leu Pro Glu Lys Val Pro Ser Ala Pro Pro Gln
            340                 345                 350

Glu Val Thr Leu Lys Pro Gly Asn Gly Thr Val Phe Val Ser Trp Val
        355                 360                 365
```

-continued

Pro Pro Pro Ala Glu Asn His Asn Gly Ile Ile Arg Gly Tyr Gln Val
370                 375                 380

Trp Ser Leu Gly Asn Thr Ser Leu Pro Pro Ala Asn Trp Thr Val Val
385                 390                 395                 400

Gly Glu Gln Thr Gln Leu Glu Ile Ala Thr His Met Pro Gly Ser Tyr
            405                 410                 415

Cys Val Gln Val Ala Ala Val Thr Gly Ala Gly Ala Gly Glu Pro Ser
            420                 425                 430

Arg Pro Val Cys Leu Leu Glu Gln Ala Met Glu Arg Ala Thr Gln
            435                 440                 445

Glu Pro Ser Glu His Gly Pro Trp Thr Leu Glu Gln Leu Arg Ala Thr
450                 455                 460

Leu Lys Arg Pro Glu Val Ile Ala Thr Cys Gly Val Ala Leu Trp Leu
465                 470                 475                 480

Leu Leu Leu Gly Thr Ala Val Cys Ile His Arg Arg Arg Ala Arg
            485                 490                 495

Val His Leu Gly Pro Gly Leu Tyr Arg Tyr Thr Ser Glu Asp Ala Ile
            500                 505                 510

Leu Lys His Arg Met Asp His Ser Asp Ser Gln Trp Leu Ala Asp Thr
            515                 520                 525

Trp Arg Ser Thr Ser Gly Ser Arg Asp Leu Ser Ser Ser Ser Ser Leu
530                 535                 540

Ser Ser Arg Leu Gly Ala Asp Ala Arg Asp Pro Leu Asp Cys Arg Arg
545                 550                 555                 560

Ser Leu Leu Ser Trp Asp Ser Arg Ser Pro Gly Val Pro Leu Leu Pro
            565                 570                 575

Asp Thr Ser Thr Phe Tyr Gly Ser Leu Ile Ala Glu Leu Pro Ser Ser
            580                 585                 590

Thr Pro Ala Arg Pro Ser Pro Gln Val Pro Ala Val Arg Arg Leu Pro
            595                 600                 605

Pro Gln Leu Ala Gln Leu Ser Ser Pro Cys Ser Ser Asp Ser Leu
610                 615                 620

Cys Ser Arg Arg Gly Leu Ser Ser Pro Arg Leu Ser Leu Ala Pro Ala
625                 630                 635                 640

Glu Ala Trp Lys Ala Lys Lys Gln Glu Leu Gln His Ala Asn Ser
            645                 650                 655

Ser Pro Leu Leu Arg Gly Ser His Ser Leu Glu Leu Arg Ala Cys Glu
            660                 665                 670

Leu Gly Asn Arg Gly Ser Lys Asn Leu Ser Gln Ser Pro Gly Ala Val
            675                 680                 685

Pro Gln Ala Leu Val Ala Trp Arg Ala Leu Gly Pro Lys Leu Leu Ser
690                 695                 700

Ser Ser Asn Glu Leu Val Thr Arg His Leu Pro Pro Ala Pro Leu Phe
705                 710                 715                 720

Pro His Glu Thr Pro Thr Gln Ser Gln Thr Gln Pro Val
            725                 730                 735

Ala Pro Gln Ala Pro Ser Ser Ile Leu Leu Pro Ala Ala Pro Ile Pro
            740                 745                 750

Ile Leu Ser Pro Cys Ser Pro Pro Ser Pro Gln Ala Ser Ser Leu Ser
            755                 760                 765

Gly Pro Ser Pro Ala Ser Ser Arg Leu Ser Ser Ser Leu Ser Ser
770                 775                 780

Leu Gly Glu Asp Gln Asp Ser Val Leu Thr Pro Glu Glu Val Ala Leu
785                 790                 795                 800

-continued

```
Cys Leu Glu Leu Ser Glu Gly Glu Glu Thr Pro Arg Asn Ser Val Ser
            805                 810                 815

Pro Met Pro Arg Ala Pro Ser Pro Thr Thr Tyr Gly Tyr Ile Ser
        820                 825                 830

Val Pro Thr Ala Ser Glu Phe Thr Asp Met Gly Arg Thr Gly Gly Gly
        835                 840                 845

Val Gly Pro Lys Gly Gly Val Leu Leu Cys Pro Pro Arg Pro Cys Leu
        850                 855                 860

Thr Pro Thr Pro Ser Glu Gly Ser Leu Ala Asn Gly Trp Gly Ser Ala
865                 870                 875                 880

Ser Glu Asp Asn Ala Ala Ser Ala Arg Ala Ser Leu Val Ser Ser Ser
                885                 890                 895

Asp Gly Ser Phe Leu Ala Asp Ala His Phe Ala Arg Ala Leu Ala Val
            900                 905                 910

Ala Val Asp Ser Phe Gly Phe Gly Leu Glu Pro Arg Glu Ala Asp Cys
        915                 920                 925

Val Phe Ile Asp Ala Ser Ser Pro Pro Ser Pro Arg Asp Glu Ile Phe
    930                 935                 940

Leu Thr Pro Asn Leu Ser Leu Pro Leu Trp Glu Trp Arg Pro Asp Trp
945                 950                 955                 960

Leu Glu Asp Met Glu Val Ser His Thr Gln Arg Leu Gly Arg Gly Met
                965                 970                 975

Pro Pro Trp Pro Pro Asp Ser Gln Ile Ser Ser Gln Arg Ser Gln Leu
            980                 985                 990

His Cys Arg Met Pro Lys Ala Gly Ala Ser Pro Val Asp Tyr Ser
        995                 1000                1005

<210> SEQ ID NO 3
<211> LENGTH: 467
<212> TYPE: PRT
<213> ORGANISM: Homo sapiens

<400> SEQUENCE: 3

Met Gly Ser Gly Gly Asp Ser Leu Leu Gly Gly Arg Gly Ser Leu Pro
1               5                   10                  15

Leu Leu Leu Leu Leu Ile Met Gly Gly Met Ala Gln Asp Ser Pro Pro
            20                  25                  30

Gln Ile Leu Val His Pro Gln Asp Gln Leu Phe Gln Gly Pro Gly Pro
        35                  40                  45

Ala Arg Met Ser Cys Gln Ala Ser Gly Gln Pro Pro Pro Thr Ile Arg
    50                  55                  60

Trp Leu Leu Asn Gly Gln Pro Leu Ser Met Val Pro Pro Asp Pro His
65                  70                  75                  80

His Leu Leu Pro Asp Gly Thr Leu Leu Leu Gln Pro Pro Ala Arg
                85                  90                  95

Gly His Ala His Asp Gly Gln Ala Leu Ser Thr Asp Leu Gly Val Tyr
            100                 105                 110

Thr Cys Glu Ala Ser Asn Arg Leu Gly Thr Ala Val Ser Arg Gly Ala
        115                 120                 125

Arg Leu Ser Val Ala Val Leu Arg Glu Asp Phe Gln Ile Gln Pro Arg
    130                 135                 140

Asp Met Val Ala Val Gly Glu Gln Phe Thr Leu Glu Cys Gly Pro
145                 150                 155                 160

Pro Trp Gly His Pro Glu Pro Thr Val Ser Trp Trp Lys Asp Gly Lys
                165                 170                 175
```

Pro Leu Ala Leu Gln Pro Gly Arg His Thr Val Ser Gly Gly Ser Leu
            180                 185                 190

Leu Met Ala Arg Ala Glu Lys Ser Asp Glu Gly Thr Tyr Met Cys Val
        195                 200                 205

Ala Thr Asn Ser Ala Gly His Arg Glu Ser Arg Ala Ala Arg Val Ser
210                 215                 220

Ile Gln Glu Pro Gln Asp Tyr Thr Glu Pro Val Glu Leu Leu Ala Val
225                 230                 235                 240

Arg Ile Gln Leu Glu Asn Val Thr Leu Leu Asn Pro Asp Pro Ala Glu
                245                 250                 255

Gly Pro Lys Pro Arg Pro Ala Val Trp Leu Ser Trp Lys Val Ser Gly
            260                 265                 270

Pro Ala Ala Pro Ala Gln Ser Tyr Thr Ala Leu Phe Arg Thr Gln Thr
        275                 280                 285

Ala Pro Gly Gly Gln Gly Ala Pro Trp Ala Glu Glu Leu Leu Ala Gly
290                 295                 300

Trp Gln Ser Ala Glu Leu Gly Gly Leu His Trp Gly Gln Asp Tyr Glu
305                 310                 315                 320

Phe Lys Val Arg Pro Ser Ser Gly Arg Ala Arg Gly Pro Asp Ser Asn
                325                 330                 335

Val Leu Leu Leu Arg Leu Pro Glu Lys Val Pro Ser Ala Pro Pro Gln
            340                 345                 350

Glu Val Thr Leu Lys Pro Gly Asn Gly Thr Val Phe Val Ser Trp Val
        355                 360                 365

Pro Pro Pro Ala Glu Asn His Asn Gly Ile Ile Arg Gly Tyr Gln Val
370                 375                 380

Trp Ser Leu Gly Asn Thr Ser Leu Pro Pro Ala Asn Trp Thr Val Val
385                 390                 395                 400

Gly Glu Gln Thr Gln Leu Glu Ile Ala Thr His Met Pro Gly Ser Tyr
                405                 410                 415

Cys Val Gln Val Ala Ala Val Thr Gly Ala Gly Ala Gly Glu Pro Ser
            420                 425                 430

Arg Pro Val Cys Leu Leu Leu Glu Gln Ala Met Glu Arg Ala Thr Gln
        435                 440                 445

Glu Pro Ser Glu His Gly Pro Trp Thr Leu Glu Gln Leu Arg Ala Thr
450                 455                 460

Leu Lys Arg
465

<210> SEQ ID NO 4
<211> LENGTH: 164
<212> TYPE: PRT
<213> ORGANISM: Homo sapiens

<400> SEQUENCE: 4

Pro Gly Pro Ala Arg Met Ser Cys Gln Ala Ser Gly Gln Pro Pro Pro
1               5                   10                  15

Thr Ile Arg Trp Leu Leu Asn Gly Gln Pro Leu Ser Met Val Pro Pro
            20                  25                  30

Asp Pro His His Leu Leu Pro Asp Gly Thr Leu Leu Leu Leu Gln Pro
        35                  40                  45

Pro Ala Arg Gly His Ala His Asp Gly Gln Ala Leu Ser Thr Asp Leu
    50                  55                  60

Gly Val Tyr Thr Cys Glu Ala Ser Asn Arg Leu Gly Thr Ala Val Ser
65                  70                  75                  80

```
Arg Gly Ala Arg Leu Ser Val Ala Val Leu Arg Glu Asp Phe Gln Ile
                 85                  90                  95

Gln Pro Arg Asp Met Val Ala Val Val Gly Glu Gln Phe Thr Leu Glu
            100                 105                 110

Cys Gly Pro Pro Trp Gly His Pro Glu Pro Thr Val Ser Trp Trp Lys
            115                 120                 125

Asp Gly Lys Pro Leu Ala Leu Gln Pro Gly Arg His Thr Val Ser Gly
            130                 135                 140

Gly Ser Leu Leu Met Ala Arg Ala Glu Lys Ser Asp Glu Gly Thr Tyr
145                 150                 155                 160

Met Cys Val Ala

<210> SEQ ID NO 5
<211> LENGTH: 71
<212> TYPE: PRT
<213> ORGANISM: Homo sapiens

<400> SEQUENCE: 5

Pro Gly Pro Ala Arg Met Ser Cys Gln Ala Ser Gly Gln Pro Pro Pro
1               5                   10                  15

Thr Ile Arg Trp Leu Leu Asn Gly Gln Pro Leu Ser Met Val Pro Pro
            20                  25                  30

Asp Pro His His Leu Leu Pro Asp Gly Thr Leu Leu Leu Leu Gln Pro
            35                  40                  45

Pro Ala Arg Gly His Ala His Asp Gly Gln Ala Leu Ser Thr Asp Leu
        50                  55                  60

Gly Val Tyr Thr Cys Glu Ala
65                  70

<210> SEQ ID NO 6
<211> LENGTH: 59
<212> TYPE: PRT
<213> ORGANISM: Homo sapiens

<400> SEQUENCE: 6

Gly Glu Gln Phe Thr Leu Glu Cys Gly Pro Trp Gly His Pro Glu
1               5                   10                  15

Pro Thr Val Ser Trp Trp Lys Asp Gly Lys Pro Leu Ala Leu Gln Pro
            20                  25                  30

Gly Arg His Thr Val Ser Gly Gly Ser Leu Leu Met Ala Arg Ala Glu
            35                  40                  45

Lys Ser Asp Glu Gly Thr Tyr Met Cys Val Ala
            50                  55

<210> SEQ ID NO 7
<211> LENGTH: 84
<212> TYPE: PRT
<213> ORGANISM: Homo sapiens

<400> SEQUENCE: 7

Pro Asp Pro Ala Glu Gly Pro Lys Pro Arg Pro Ala Val Trp Leu Ser
1               5                   10                  15

Trp Lys Val Ser Gly Pro Ala Ala Pro Ala Gln Ser Tyr Thr Ala Leu
            20                  25                  30

Phe Arg Thr Gln Thr Ala Pro Gly Gly Gln Gly Ala Pro Trp Ala Glu
            35                  40                  45

Glu Leu Leu Ala Gly Trp Gln Ser Ala Glu Leu Gly Gly Leu His Trp
        50                  55                  60
```

```
Gly Gln Asp Tyr Glu Phe Lys Val Arg Pro Ser Ser Gly Arg Ala Arg
65                  70                  75                  80

Gly Pro Asp Ser

<210> SEQ ID NO 8
<211> LENGTH: 86
<212> TYPE: PRT
<213> ORGANISM: Homo sapiens

<400> SEQUENCE: 8

Pro Ser Ala Pro Pro Gln Glu Val Thr Leu Lys Pro Gly Asn Gly Thr
1               5                   10                  15

Val Phe Val Ser Trp Val Pro Pro Ala Glu Asn His Asn Gly Ile
            20                  25                  30

Ile Arg Gly Tyr Gln Val Trp Ser Leu Gly Asn Thr Ser Leu Pro Pro
        35                  40                  45

Ala Asn Trp Thr Val Val Gly Glu Gln Thr Gln Leu Glu Ile Ala Thr
    50                  55                  60

His Met Pro Gly Ser Tyr Cys Val Gln Val Ala Ala Val Thr Gly Ala
65                  70                  75                  80

Gly Ala Gly Glu Pro Ser
                85

<210> SEQ ID NO 9
<211> LENGTH: 10
<212> TYPE: PRT
<213> ORGANISM: Artificial
<220> FEATURE:
<223> OTHER INFORMATION: MR7 Ab light chain CDR1

<400> SEQUENCE: 9

Ser Ala Ser Ser Ser Val Ser Tyr Met Tyr
1               5                   10

<210> SEQ ID NO 10
<211> LENGTH: 7
<212> TYPE: PRT
<213> ORGANISM: Artificial
<220> FEATURE:
<223> OTHER INFORMATION: MR7 Ab light chain CDR2

<400> SEQUENCE: 10

Leu Thr Ser Asn Leu Ala Ser
1               5

<210> SEQ ID NO 11
<211> LENGTH: 9
<212> TYPE: PRT
<213> ORGANISM: Artificial
<220> FEATURE:
<223> OTHER INFORMATION: MR7 Ab light chain CDR3

<400> SEQUENCE: 11

Gln Gln Trp Ser Ser Asn Pro Leu Thr
1               5

<210> SEQ ID NO 12
<211> LENGTH: 106
<212> TYPE: PRT
<213> ORGANISM: Artificial
<220> FEATURE:
<223> OTHER INFORMATION: MR7 Ab light chain
```

-continued

```
<400> SEQUENCE: 12

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 13
<211> LENGTH: 5
<212> TYPE: PRT
<213> ORGANISM: Artificial
<220> FEATURE:
<223> OTHER INFORMATION: MR7 Ab heavy chain CDR1

<400> SEQUENCE: 13

Asp Tyr Asn Leu Asn
1               5

<210> SEQ ID NO 14
<211> LENGTH: 17
<212> TYPE: PRT
<213> ORGANISM: Artificial
<220> FEATURE:
<223> OTHER INFORMATION: MR7 Ab heavy chain CDR2

<400> SEQUENCE: 14

Val Ile Asn Pro Asn Tyr Gly Thr Thr Ser Tyr Asn Gln Lys Phe Lys
1               5                   10                  15

Gly

<210> SEQ ID NO 15
<211> LENGTH: 7
<212> TYPE: PRT
<213> ORGANISM: Artificial
<220> FEATURE:
<223> OTHER INFORMATION: MR7 Ab heavy chain CDR3

<400> SEQUENCE: 15

Gly Arg Asp Tyr Phe Gly Tyr
1               5

<210> SEQ ID NO 16
<211> LENGTH: 116
<212> TYPE: PRT
<213> ORGANISM: Artificial
<220> FEATURE:
<223> OTHER INFORMATION: MR7 Ab heavy chain

<400> SEQUENCE: 16

Gln Val Lys Leu Gln Glu Ser Gly Pro Glu Leu Val Lys Pro Gly Ala
1               5                   10                  15

Ser Val Lys Ile Ser Cys Lys Ala Ser Gly Tyr Ser Leu Thr Asp Tyr
            20                  25                  30
```

Asn Leu Asn Trp Val Lys Gln Asn Lys Gly Lys Ser Leu Glu Trp Ile
            35                  40                  45

Gly Val Ile Asn Pro Asn Tyr Gly Thr Thr Ser Tyr Asn Gln Lys Phe
        50                  55                  60

Lys Gly Lys Ala Thr Leu Thr Val Asp Gln Ser Ser Thr Thr Tyr
 65                  70                  75                  80

Met Gln Leu Asn Ser Leu Thr Ser Glu Asp Ser Ala Val Tyr Tyr Cys
                85                  90                  95

Ala Arg Gly Arg Asp Tyr Phe Gly Tyr Trp Gly Gln Gly Thr Thr Val
            100                 105                 110

Thr Val Ser Ser
        115

<210> SEQ ID NO 17
<211> LENGTH: 116
<212> TYPE: PRT
<213> ORGANISM: Artificial
<220> FEATURE:
<223> OTHER INFORMATION: MR7 Ab heavy chain

<400> SEQUENCE: 17

Gln Val Gln Leu Gln Glu Ser Gly Pro Glu Leu Val Lys Pro Gly Ala
 1               5                  10                  15

Ser Val Lys Ile Ser Cys Lys Ala Ser Gly Tyr Ser Leu Thr Asp Tyr
            20                  25                  30

Asn Leu Asn Trp Val Lys Gln Asn Lys Gly Lys Ser Leu Glu Trp Ile
            35                  40                  45

Gly Val Ile Asn Pro Asn Tyr Gly Thr Thr Ser Tyr Asn Gln Lys Phe
        50                  55                  60

Lys Gly Lys Ala Thr Leu Thr Val Asp Gln Ser Ser Thr Thr Tyr
 65                  70                  75                  80

Met Gln Leu Asn Ser Leu Thr Ser Glu Asp Ser Ala Val Tyr Tyr Cys
                85                  90                  95

Ala Arg Gly Arg Asp Tyr Phe Gly Tyr Trp Gly Gln Gly Thr Thr Val
            100                 105                 110

Thr Val Ser Ser
        115

<210> SEQ ID NO 18
<211> LENGTH: 30
<212> TYPE: DNA
<213> ORGANISM: Artificial
<220> FEATURE:
<223> OTHER INFORMATION: Polynucleotide encoding MR7 Ab CDR

<400> SEQUENCE: 18
agtgccagct caagtgtaag ttacatgtac                                       30

<210> SEQ ID NO 19
<211> LENGTH: 22
<212> TYPE: DNA
<213> ORGANISM: Artificial
<220> FEATURE:
<223> OTHER INFORMATION: Polynucleotide encoding MR7 Ab CDR

<400> SEQUENCE: 19
tctcacatcc aacctggctt ct                                               22

-continued

<210> SEQ ID NO 20
<211> LENGTH: 27
<212> TYPE: DNA
<213> ORGANISM: Artificial
<220> FEATURE:
<223> OTHER INFORMATION: Polynucleotide encoding MR7 Ab CDR

<400> SEQUENCE: 20
cagcagtgga gtagtaaccc actcacg                                        27

<210> SEQ ID NO 21
<211> LENGTH: 318
<212> TYPE: DNA
<213> ORGANISM: Artificial
<220> FEATURE:
<223> OTHER INFORMATION: Polynucleotide encoding MR7 Ab chain

<400> SEQUENCE: 21
caaattgttc tcacccagtc tccagcactc atgtctgcat ctccagggga gaaggtcacc    60
atgacctgca gtgccagctc aagtgtaagt tacatgtact ggtaccagca gaagccaaga  120
tcctccccca aaccctggat ttatctcaca tccaacctgg cttctggagt ccctgctcgc  180
ttcagtggca gtgggtctgg gacctcttac tctctcacaa tcagcagcat ggaggctgaa  240
gatgctgcca cttattactg ccagcagtgg agtagtaacc cactcacgtt cggtgctggg  300
accaagctgg agctgaaa                                                318

<210> SEQ ID NO 22
<211> LENGTH: 15
<212> TYPE: DNA
<213> ORGANISM: Artificial
<220> FEATURE:
<223> OTHER INFORMATION: Polynucleotide encoding MR7 Ab CDR

<400> SEQUENCE: 22
gactacaacc tgaac                                                    15

<210> SEQ ID NO 23
<211> LENGTH: 48
<212> TYPE: DNA
<213> ORGANISM: Artificial
<220> FEATURE:
<223> OTHER INFORMATION: Polynucleotide encoding MR7 Ab CDR

<400> SEQUENCE: 23
gtaattaatc caaactatgg tactagttac aatcagaagt tcaagggc                48

<210> SEQ ID NO 24
<211> LENGTH: 21
<212> TYPE: DNA
<213> ORGANISM: Artificial
<220> FEATURE:
<223> OTHER INFORMATION: Polynucleotide encoding MR7 Ab CDR

<400> SEQUENCE: 24
gggagggatt acttcggcta c                                             21

<210> SEQ ID NO 25
<211> LENGTH: 345
<212> TYPE: DNA
<213> ORGANISM: Artificial
<220> FEATURE:
<223> OTHER INFORMATION: Polynucleotide encoding MR7 Ab chain

<400> SEQUENCE: 25

```
caggtcaagc tgcaggagtc aggacctgag ctggtgaagc ctggcgcttc agtgaagata      60
tcctgcaagg cttctggtta ctcactcact gactacaacc tgaactgggt gaagcagaac    120
aaaggaaaga gccttgagtg gattggagta attaatccaa actatggtac tagttacaat    180
cagaagttca aggcaaggc cacattgact gtagaccaat cttccagcac aacctacatg     240
cagctcaaca gcctgacatc tgaggactct gcagtctatt actgtgcaag agggagggat    300
tacttcggct actggggcca aggaccacg gtcaccgtct cctca                     345
```

<210> SEQ ID NO 26
<211> LENGTH: 345
<212> TYPE: DNA
<213> ORGANISM: Artificial
<220> FEATURE:
<223> OTHER INFORMATION: Polynucleotide encoding MR7 Ab chain

<400> SEQUENCE: 26

```
caggtcaaac tgcaggagtc aggacctgag ctggtgaagc ctggcgcttc agtgaagata      60
tcctgcaagg cttctggtta ctcactcact gactacaacc tgaactgggt gaagcagaac    120
aaaggaaaga gccttgagtg gattggagta attaatccaa actatggtac tagttacaat    180
cagaagttca aggcaaggc cacattgact gtagaccaat cttccagcac aacctacatg     240
cagctcaaca gcctgacatc tgaggactct gcagtctatt actgtgcaag agggagggat    300
tacttcggct actggggcca aggaccacg gtcaccgtct cctca                     345
```

<210> SEQ ID NO 27
<211> LENGTH: 345
<212> TYPE: DNA
<213> ORGANISM: Artificial
<220> FEATURE:
<223> OTHER INFORMATION: Polynucleotide encoding MR7 Ab chain

<400> SEQUENCE: 27

```
caggtccaac tgcaggagtc aggacctgag ctggtgaagc ctggcgcttc agtgaagata      60
tcctgcaagg cttctggtta ctcactcact gactacaacc tgaactgggt gaagcagaac    120
aaaggaaaga gccttgagtg gattggagta attaatccaa actatggtac tagttacaat    180
cagaagttca aggcaaggc cacattgact gtagaccaat cttccagcac aacctacatg     240
cagctcaaca gcctgacatc tgaggactct gcagtctatt actgtgcaag agggagggat    300
tacttcggct actggggcca aggaccacg gtcaccgtct cctca                     345
```

<210> SEQ ID NO 28
<211> LENGTH: 20
<212> TYPE: PRT
<213> ORGANISM: Homo sapiens

<400> SEQUENCE: 28

```
Leu Leu Gln Pro Pro Ala Arg Gly His Ala His Asp Gly Gln Ala Leu
1               5                   10                  15
Ser Thr Asp Leu
            20
```

<210> SEQ ID NO 29
<211> LENGTH: 17
<212> TYPE: PRT
<213> ORGANISM: Homo sapiens -continued

<400> SEQUENCE: 29

Leu Ser Gln Ser Pro Gly Ala Val Pro Gln Ala Leu Val Ala Trp Arg
1               5                   10                  15

Ala

<210> SEQ ID NO 30
<211> LENGTH: 1459
<212> TYPE: DNA
<213> ORGANISM: Artificial
<220> FEATURE:
<223> OTHER INFORMATION: Plasmid NH10 insert

<400> SEQUENCE: 30
aagcttaaag tgctcgggac aaggacatag ggctgagagt agccatgggc tctggaggag      60
acagcctcct gggggggcagg ggttccctgc ctctgctgct cctgctcatc atgggaggca    120
tggctcagga ctccccgccc cagatcctag tccaccccca ggaccagctg ttccagggcc    180
ctggccctgc caggatgagc tgccaagcct caggccagcc acctcccacc atccgctggt    240
tgctgaatgg gcagcccctg agcatggtgc cccagaccc acaccacctc ctgcctgatg      300
ggacccttct gctgctacag ccccctgccc ggggacatgc ccacgatggc caggccctgt    360
ccacagacct gggtgtctac acatgtgagg ccagcaaccg gcttggcacg gcagtcagca    420
gaggcgctcg gctgtctgtg gctgtcctcc gggaggattt ccagatccag cctcgggaca    480
tggtggctgt ggtgggtgag cagtttactc tggaatgtgg ccgccctgg ggccacccag      540 agcccacagt ctcatggtgg aaagatggga accccctggc cctccagccc ggaaggcaca    600
cagtgtccgg ggggtccctg ctgatggcaa gagcagagaa gagtgacgaa gggacctaca    660
tgtgtgtggc caccaacagc gcaggacata gggagagccg cgcagcccgg gtttccatcc    720
aggagcccca ggactacacg gagcctgtgg agcttctggc tgtgcgaatt cagctggaaa    780
atgtgacact gctgaacccg gatcctcag agggccccaa gcctagaccg gcggtgtggc      840
tcagctggaa ggtcagtggc cctgctgcgc ctgcccaatc ttacacggcc ttgttcagga    900
cccagactgc cccggggagc cagggagctc cgtgggcaga ggagctgctg gccggctggc    960
agagcgcaga gcttggaggc ctccactggg gccaagacta cgagttcaaa gtgagaccat   1020
cctctggccg ggctcgaggc cctgacagca acgtgctgct cctgaggctg ccggaaaaag   1080
tgcccagtgc cccacctcag gaagtgactc taaagcctgg caatggcact gtctttgtga   1140
gctgggtccc accacctgct gaaaaccaca atggcatcat ccgtggctac caggtctgga   1200
gcctgggcaa cacatcactg ccaccagcca actggactgt agttggtgag cagacccagc   1260
tggaaatcgc cacccatatg ccaggctcct actgcgtgca agtggctgca gtcactggtg   1320
ctggagctgg ggagcccagt agacctgtct gcctccttt agagcaggcc atggagcgag   1380
ccacccaaga acccagtgag catggtccct ggaccctgga gcagctgagg gctaccttga   1440
agcggtagta agcggccgc                                                  1459

<210> SEQ ID NO 31
<211> LENGTH: 1533
<212> TYPE: DNA
<213> ORGANISM: Artificial
<220> FEATURE:
<223> OTHER INFORMATION: pIG vector

<400> SEQUENCE: 31
aagcttgata tcgaattctg cagcccgggg gatccggagg gagggtgtct gctggaagca     60
ggctcagcgc tcctgcctgg acgcatcccg gctatgcagc cccagtccag ggcagcaagg    120

```
caggccccgt ctgcctcttc acccggaggc ctctgcccgc cccactcatg ctcagggaga      180
gggtcttctg gctttttccc caggctctgg gcaggcacag gctaggtgcc cctaacccag      240
gccctgcaca caaaggggca ggtgctgggc tcagacctgc caagagccat atccgggagg      300
accctgcccc tgacctaagc ccaccccaaa ggcaaactc tccactccct cagctcggac       360
accttctctc ctcccagatt ccagtaactc caatcttct ctctgcagag cccaaatctt       420
gtgacaaaac tcacacatgc ccaccgtgcc caggtaagcc agcccaggcc tcgccctcca      480
gctcaaggcg ggacaggtgc cctagagtag cctgcatcca gggacaggcc ccagccgggt      540
gctgacacgt ccacctccat ctcttcctca gcacctcaac tcctgggggg accgtcagtc      600
ttcctcttcc ccccaaaacc caaggacacc ctcatgatct cccggacccc tgaggtcaca      660
tgcgtggtgg tggacgtgag ccacgaagac cctgaggtca agttcaactg gtacgtggac      720
ggcgtggagg tgcataatgc caagacaaag ccgcgggagg agcagtacaa cagcacgtac      780
cgggtggtca gcgtcctcac cgtcctgcac caggactggc tgaatggcaa ggagtacaag      840
tgcaaggtct ccaacaaagc cctcccagcc cccatcgaga aaaccatctc caaagccaaa      900
ggtgggaccc gtggggtgcg agggccacat ggacagaggc cggctcggcc caccctctgc      960
cctgagagtg accgctgtac caacctctgt cctacagggc agccccgaga accacaggtg     1020
tacaccctgc ccccatcccg ccatgacctg accaagaacc aggtcagcct gacctgcctg     1080
gtcaaaggct tctatcccag cgacatcgcc gtggagtggg agagcaatgg gcagccggag     1140
aacaactaca agaccacgcc tcccgtgctg gactccgacg gctccttctt cctctacagc     1200
aagctcaccg tggacaagag caggtggcag caggggaacg tcttctcatg ctccgtgatg     1260
catgaggctc tgcacaacca ctacacgcag aagagcctct ccctgtctcc gggtaaatga     1320
gtgcgacggc cggcaagccc cgctccccgg gctctcgcgg tcgcacgacc atgcttggca     1380
cgtaccccct gtacatactt cccgggcgcc cagcatggaa ataaagcacc cagcgctgcc     1440 ctgggccct gcgagactgt gatggttctt tccacgggtc accccgagtc tgaggcctga     1500
gtggcatgag ggaggcagcg gccgcgactc tag                                  1533
```

```
<210> SEQ ID NO 32
<211> LENGTH: 40
<212> TYPE: DNA
<213> ORGANISM: Artificial
<220> FEATURE:
<223> OTHER INFORMATION: Kappa light chain 5' oligonucleotide primer

<400> SEQUENCE: 32
actagtcgac atgaagttgc ctgttaggct gttggtgctg                            40

<210> SEQ ID NO 33
<211> LENGTH: 39
<212> TYPE: DNA
<213> ORGANISM: Artificial
<220> FEATURE:
<223> OTHER INFORMATION: Kappa light chain 5' oligonucleotide primer

<400> SEQUENCE: 33
actagtcgac atggagwcag acacactcct gytatgggt                             39

<210> SEQ ID NO 34
<211> LENGTH: 41
<212> TYPE: DNA
<213> ORGANISM: Artificial
<220> FEATURE:
<223> OTHER INFORMATION: Kappa light chain 5' oligonucleotide primer
```

<400> SEQUENCE: 34
actagtcgac atgagtgtgg ctcactcagg tcctggsgtt g                41

<210> SEQ ID NO 35
<211> LENGTH: 41
<212> TYPE: DNA
<213> ORGANISM: Artificial
<220> FEATURE:
<223> OTHER INFORMATION: Kappa light chain 5' oligonucleotide primer

<400> SEQUENCE: 35
actagtcgac atgaggrccc ctgctcagwt tyttggmwtc t                41

<210> SEQ ID NO 36
<211> LENGTH: 40
<212> TYPE: DNA
<213> ORGANISM: Artificial
<220> FEATURE:
<223> OTHER INFORMATION: Kappa light chain 5' oligonucleotide primer

<400> SEQUENCE: 36
actagtcgac atggatttwc aggtgcagat twtcagcttc                  40

<210> SEQ ID NO 37
<211> LENGTH: 37
<212> TYPE: DNA
<213> ORGANISM: Artificial
<220> FEATURE:
<223> OTHER INFORMATION: Kappa light chain 5' oligonucleotide primer

<400> SEQUENCE: 37
actagtcgac atgaggtkcc ytgytcagyt yctgrgg                     37

<210> SEQ ID NO 38
<211> LENGTH: 41
<212> TYPE: DNA
<213> ORGANISM: Artificial
<220> FEATURE:
<223> OTHER INFORMATION: Kappa light chain 5' oligonucleotide primer

<400> SEQUENCE: 38
actagtcgac atgggcwtca agatggagtc acakwyycwg g                41

<210> SEQ ID NO 39
<211> LENGTH: 41
<212> TYPE: DNA
<213> ORGANISM: Artificial
<220> FEATURE:
<223> OTHER INFORMATION: Kappa light chain 5' oligonucleotide primer

<400> SEQUENCE: 39
actagtcgac atgtggggay cttkttyamm tttttcaatt g                41

<210> SEQ ID NO 40
<211> LENGTH: 35
<212> TYPE: DNA
<213> ORGANISM: Artificial
<220> FEATURE:
<223> OTHER INFORMATION: Kappa light chain 5' oligonucleotide primer

<400> SEQUENCE: 40
actagtcgac atggtrtccw casctcagtt ccttg                       35

```
<210> SEQ ID NO 41
<211> LENGTH: 37
<212> TYPE: DNA
<213> ORGANISM: Artificial
<220> FEATURE:
<223> OTHER INFORMATION: Kappa light chain 5' oligonucleotide primer

<400> SEQUENCE: 41
actagtcgac atgtatatat gtttgttgtc tatttct                              37

<210> SEQ ID NO 42
<211> LENGTH: 39
<212> TYPE: DNA
<213> ORGANISM: Artificial
<220> FEATURE:
<223> OTHER INFORMATION: Kappa light chain 5' oligonucleotide primer

<400> SEQUENCE: 42
actagtcgac atggaagccc catgctcagc ttctcttcc                            39

<210> SEQ ID NO 43
<211> LENGTH: 22
<212> TYPE: DNA
<213> ORGANISM: Artificial
<220> FEATURE:
<223> OTHER INFORMATION: Kappa light chain 3' oligonucleotide primer

<400> SEQUENCE: 43
gtttgatcta gagcttggtc cc                                              22

<210> SEQ ID NO 44
<211> LENGTH: 20
<212> TYPE: DNA
<213> ORGANISM: Artificial
<220> FEATURE:
<223> OTHER INFORMATION: Kappa light chain constant region 3'
      oligonucleotide primer

<400> SEQUENCE: 44
ttggagggcg ttatccacct                                                 20

<210> SEQ ID NO 45
<211> LENGTH: 31
<212> TYPE: DNA
<213> ORGANISM: Artificial
<220> FEATURE:
<223> OTHER INFORMATION: Heavy chain 5' primer

<400> SEQUENCE: 45
atcggatcca ggtsmarctg cagsagtcwg g                                    31

<210> SEQ ID NO 46
<211> LENGTH: 41
<212> TYPE: DNA
<213> ORGANISM: Artificial
<220> FEATURE:
<223> OTHER INFORMATION: Heavy chain 3' primer

<400> SEQUENCE: 46
ctcgaattct gaggagacgg tgaccgtggt cccttggccc c                         41
```

ANTIBODIES, POLYPEPTIDES AND USES THEREOF

RELATED APPLICATIONS

This application is a continuation of U.S. application Ser. No. 10/535,873, filed Nov. 21, 2005, which is a National Stage of International Application No.: PCT/GB03/05059, filed Nov. 20, 2003, which claims priority to United Kingdom Application No.: 0321401.2, filed Sep. 12, 2003 and United Kingdom Application No.: 0227080.9, filed Nov. 20, 2002, the entire contents of which are hereby incorporated by reference.

FIELD OF THE INVENTION

The present invention relates to antibodies and polypeptides, and in particular to ECSM4 antibodies and polypeptides that inhibit angiogenesis and their use therefor.

BACKGROUND OF THE INVENTION

Endothelial cells form a single cell layer that lines all blood vessels and regulates exchanges between the blood stream and the surrounding tissues. New blood vessels develop from the walls of existing small vessels by the outgrowth of these endothelial cells which have the capacity to form hollow capillary tubes even when isolated in culture. In vivo, damaged tissues and some tumours attract a blood supply by secreting factors that stimulate nearby endothelial cells to construct new capillary sprouts. Tumours that fail to attract a blood supply are severely limited in their growth.

The process whereby new vessels originate as capillaries, which sprout from existing small vessels, is called angiogenesis. It can therefore be seen that angiogenesis plays a major role in normal tissue development and repair and in the progression of some pathological conditions.

Once the vascular system is fully developed, endothelial cells of blood vessels normally remain quiescent with no new vessel formation, with the exception of the formation of new blood vessels in natural wound healing. However, a deregulation of blood vessel growth and an abnormal increase in vessel density can occur in diseases or conditions such as tumourigenesis, diabetic retinopathy, psoriasis and inflammation. Therefore the ability to inhibit inappropriate or undesirable angiogenesis may be useful in the treatment of these diseases or conditions.

FIGURE DESCRIPTIONS

The invention will now be described in more detail by reference to the following Examples and Figures.

FIGS. 1A and 1B show the DNA sequence of the insert used to generate plasmid N1 (SEQ ID NO: 1). FIG. 1C shows the amino acid sequence encoded by the insert (SEQ ID NO: 2). This sequence is the full length MR amino acid sequence.

FIG. 2A shows the DNA sequence of the insert used to generate plasmid NH10 (SEQ ID NO: 30). FIG. 2B shows the amino acid sequence encoded by the insert used for generating plasmid NH10. This sequence is designated as the MR ectodomain and is the amino acid sequence of the entire extracellular fragment of MR (residues 1-467, SEQ ID NO: 3).

FIG. 3 shows the amino acid sequence of the Ig region of MR (residues 46-209, SEQ ID NO: 4).

FIG. 4A shows the amino acid sequence of the IgA domain of MR (residues 46-116, SEQ ID NO: 5). FIG. 4B shows the amino acid sequence of the IgB domain of MR (residues 151-209, SEQ ID NO: 5).

FIG. 7 shows sprout formation from rat aorta in the presence of antibody or soluble MR extracellular domain. Rat aorta sections were cultured for 5 days in the presence of media alone (A), or in media containing 100 µg/ml MR-7 antibody (B), or 15 µg/ml soluble MR extracellular domain (residues 1-467) (C). Four pictures are shown for each treatment group and are representative of sprouting levels from duplicate aortas.

Figure 8:
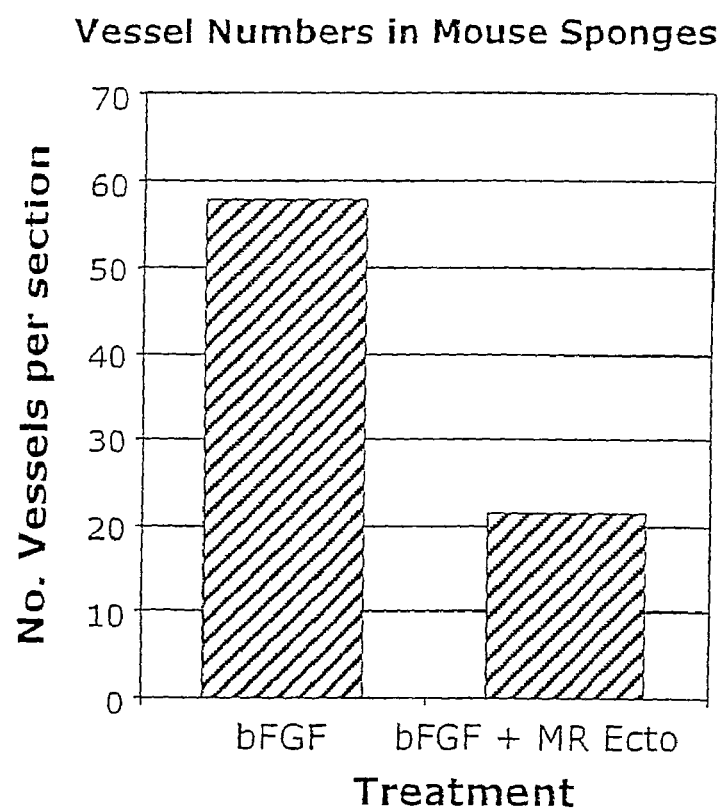

FIG. 8 is a graph and a table showing the effect of the soluble extracellular domain of MR (MR ectodomain) on formation of new blood vessels in the sponge angiogenesis assay.

Figure 9A:
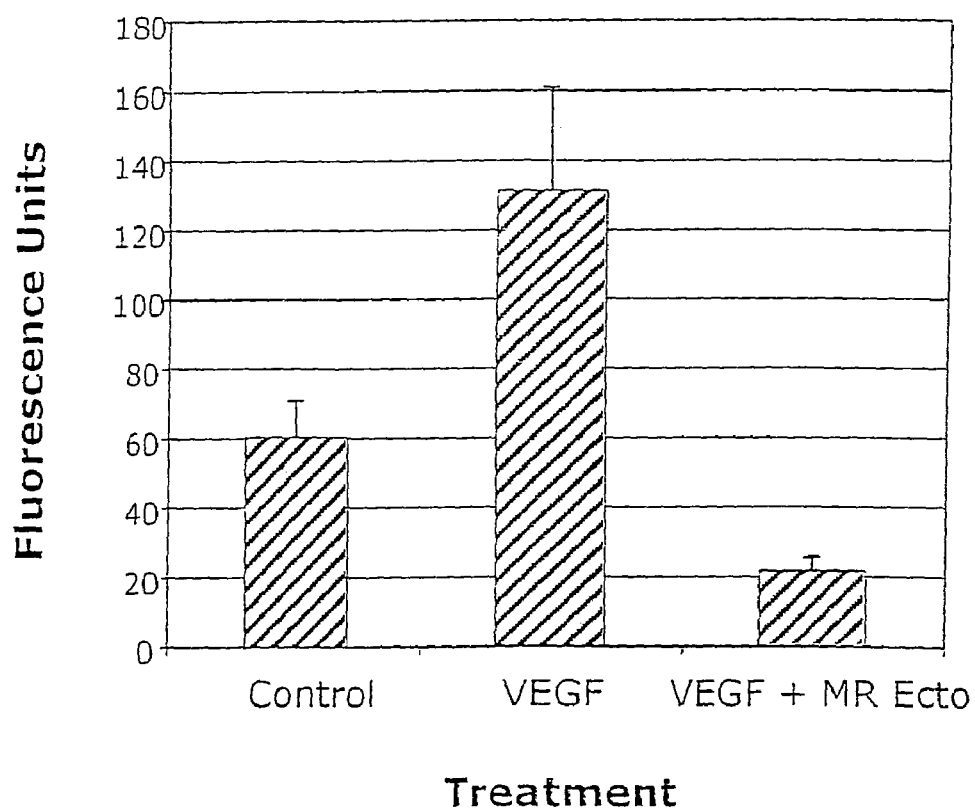

FIG. 9A is a graph and a table showing that the vascular endothelial growth factor (VEGF) induced migration of primary human endothelial cells is inhibited by the MR extracellular domain.

Figure 9B:
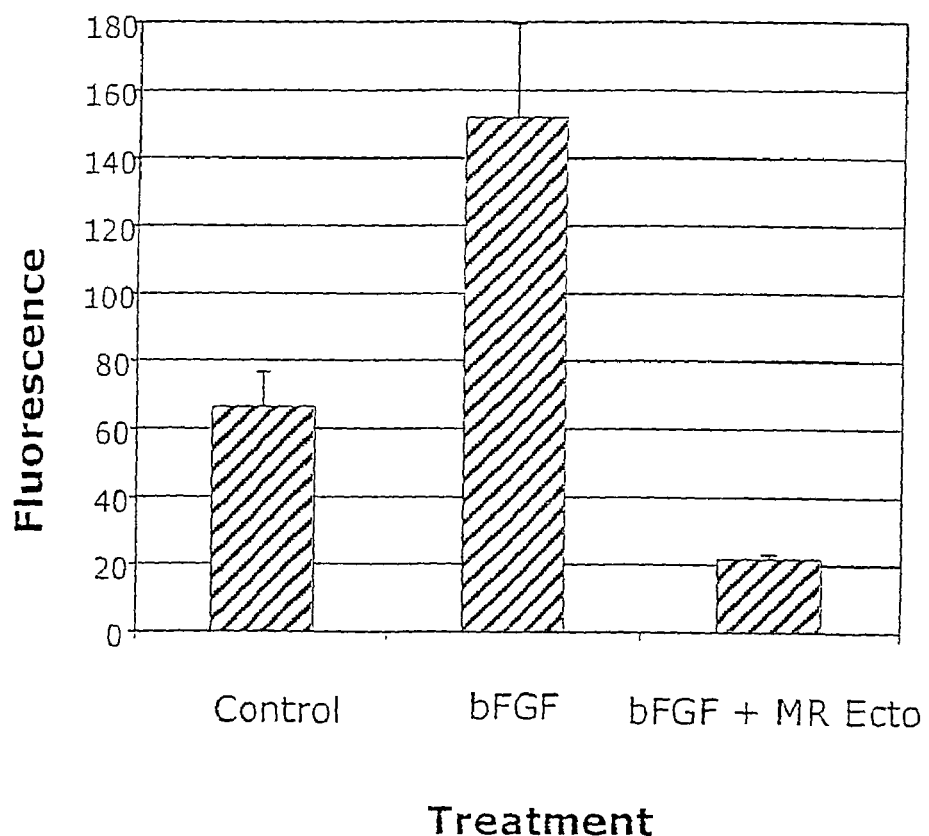

FIG. 9B is a graph and a table showing that the basic fibroblast growth factor (bFGF) induced migration of primary human endothelial cells is inhibited by the MR extracellular domain.

Figure 10:
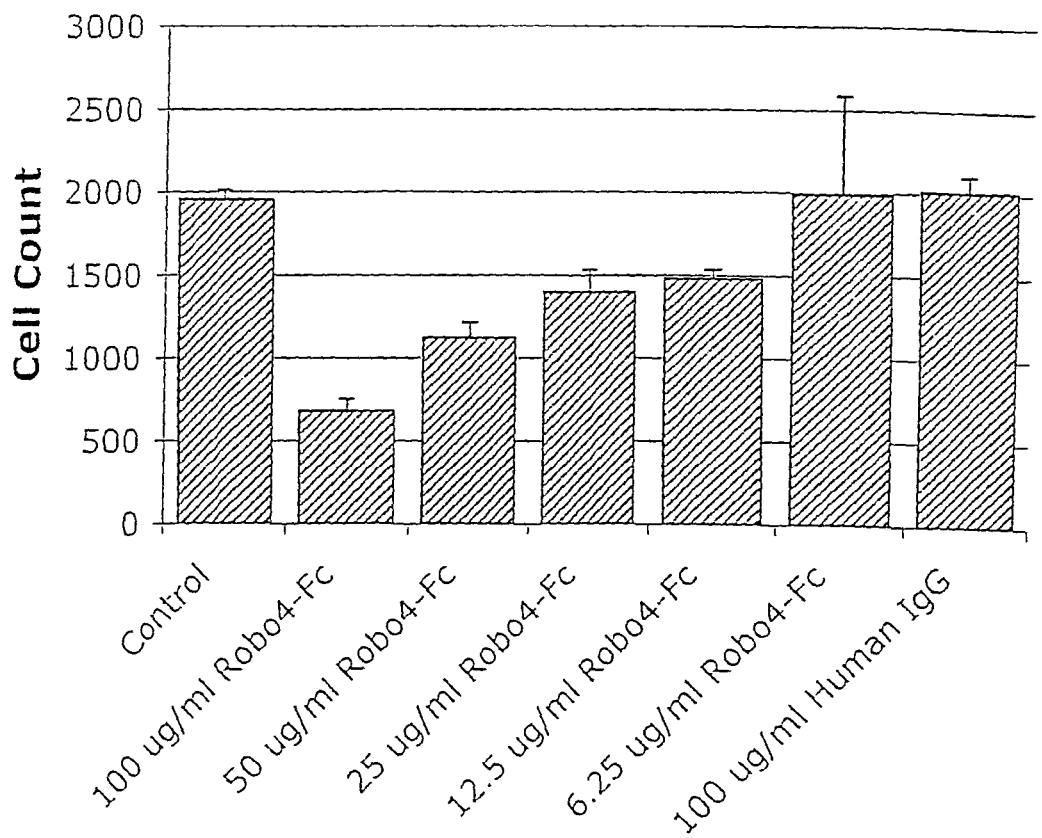

FIG. 10 is a graph and a table showing that the MR ectodomain (Robo4-Fc) inhibits proliferation of primary human endothelial cells.

DETAILED DESCRIPTION

Human magic roundabout (MR; also known as endothelial cell-specific molecule 4, ECSM4) has previously been shown to have a highly endothelial-cell selective expression profile (Huminiecki & Bicknell (2000), *Genome Research*, 10, 1796-1806; and WO 02/36771). MR expression in vivo was shown to be restricted to sites of active angiogenesis, notably tumour vessels (Huminiecki et al. (2002) *Genomics*, 79(4), 547-552).

Based on this information it was suggested in WO 02/36771 that compounds comprising a moiety that binds to MR, such as an antibody, and a further functional moiety, may be useful for a variety of medical purposes including imaging the vascular epithelium; diagnosing or prognosing a condition involving the vascular endothelium; assessing the efficacy of anti-angiogenic therapies; detecting endothelial damage; detecting a tumour or tumour neovasculature or cardiac disease or endometriosis or atherosclerosis; treating a proliferative disease involving the vascular endothelium such as cancer, psoriasis, diabetic retinopathy, artherosclerosis or menorrhagia; introducing genetic material into vascular endothelial cells; and modulating angiogenesis.

For example, WO 02/36771 teaches a compound comprising a moiety that binds to MR, such as an antibody, and a further moiety such as an inhibitor of angiogenesis (page 27). WO 02/36771 also teaches a compound comprising a moiety that binds to MR, such as an antibody, and a further moiety such as a cytotoxic moiety that destroys or slows or reverses the growth of the neovasculature (page 35).

However, in each case, the moiety that binds to MR merely directs the functional moiety to a desired endothelial location for use. WO 02/36771 does not suggest that the moiety that binds to MR is itself functional, let alone that it inhibits MR or can be used to inhibit angiogenesis.

We have now shown that an antibody that selectively binds to the extracellular region of MR results in inhibition of angiogenesis.

On the paragraph spanning pages 71-72, WO 02/36771 states that both antibodies which stimulate or activate MR and antibodies which prevent stimulation and activation of MR could be used to modulate angiogenesis. However, it does not suggest that an antibody that selectively binds to the extracellular region of MR can be used to inhibit angiogenesis. Moreover, to the best of the inventors' knowledge, neither WO 02/36771 nor any other document shows any evidence that an antibody that selectively binds to the extracellular region of MR does, in fact, inhibit angiogenesis.

There is thus provided in accordance with a first aspect of the invention a method of inhibiting angiogenesis in an individual in need thereof comprising administering an antibody that selectively binds to the extracellular region of human magic roundabout (MR) to the individual.

By "inhibiting angiogenesis" we include the meaning of reducing the rate or level of angiogenesis. The reduction can be a low level reduction of about 10%, or about 20%, or about 30%, or about 40% of the rate or level of angiogenesis. Preferably, the reduction is a medium level reduction of about 50%, or about 60%, or about 70%, or about 80% reduction of the rate or level of angiogenesis. More preferably, the reduction is a high level reduction of about 90%, or about 95%, or about 99%, or about 99.9%, or about 99.99% of the rate or level of angiogenesis. Most preferably, inhibition can also include the elimination of angiogenesis or its reduction to an undetectable level.

Methods and assays for determining the rate or level of angiogenesis, and hence for determining whether and to what extent an antibody inhibits angiogenesis, are known in the art.

For example, U.S. Pat. No. 6,225,118 B1 to Grant et al, incorporated herein by reference, describes a multicellular in vitro assay for modelling the combined stages of angiogenesis namely the proliferation, migration and differentiation stages of cell development.

The AngioKit, Catalogue No. ZHA-1000, by TCS Cell-Works Ltd, Buckingham MK18 2LR, UK, is a suitable model of human angiogenesis for analysing the angiogenic or anti-angiogenic properties of test compounds.

The rate or level of angiogenesis can also be determined using the aortic ring assay described in Example 2.

Preferably, the antibody also inhibits angiogenesis in vivo, especially in mammals, and most preferably in humans By "MR" we include the gene product of the human magic roundabout gene (also known as ECSM4) and naturally occurring variants thereof. The cDNA and amino acid sequence of MR are found in Genbank Accession Nos. AF361473 and AAL31867, and are shown in FIG. 1 (SEQ ID NOs: 1 and 2, respectively).

MR is a transmembrane protein and has been predicted to have an extracellular region at residues 1-467 (SEQ ID NO: 3), a transmembrane region at residues 468-490, and an intracellular region at residues 491-1007 (Huminiecki et al., 2002). The extracellular region of MR has an immunoglobulin (Ig) region at residues 46-209 (SEQ ID NO: 4), which can be further subdefined into an IgA domain at residues 46-116 (SEQ ID NO: 5), and an IgB domain at residues 151-209 (SEQ ID NO: 6), and two fibronectin type III domains at residues 252-335 (SEQ ID NO: 7) and 347-432 (SEQ ID NO: 8). The MR amino acid residue numbering is that given in AF361473, AAL31867 and in FIG. 1C.

By an antibody that "selectively binds" a specified domain or region of MR, such as an Ig domain, we include the meaning that the antibody binds the specific domain with a greater affinity than for any other region of MR. Preferably, the antibody binds the specified domain of MR with at least 2, or at least 5, or at least 10 or at least 50 times greater affinity than any other region of MR. More preferably, the antibody binds the specific domain of MR with at least 100, or at least 1,000, or at least 10,000 times greater affinity than any other region of MR. Such binding may be determined by methods well known in the art. Preferably, the antibody selectively binds a particular epitope within MR and does not bind other epitopes.

Preferably, when the antibody is administered to an individual, the antibody binds MR at the specified domain with a greater affinity than for any other molecule in the individual. Preferably, the agent binds MR at the specific domain with at least 2, or at least 5, or at least 10 or at least 50 times greater affinity than for any other molecule in the individual. More preferably, the agent binds MR at the specific domain with at least 100, or at least 1,000, or at least 10,000 times greater affinity than any other molecule in the individual.

Inhibition of angiogenesis may be useful in combating any disease or condition involving unwanted, undesirable or inappropriate angiogenesis. Such conditions include tumours/cancer, psoriasis, atherosclerosis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation.

By cancer is included Kaposi's sarcoma, leukaemia, lymphoma, myeloma, solid carcinomas (both primary and secondary (metastasis), vascular tumours including haemangioma (both capillary and juvenile (infantile)), haemangiomatosis and haemagioblastoma.

The tumours that may be treated by the methods of the invention include any tumours which are associated with new blood vessel production.

The term "tumour" is to be understood as referring to all forms of neoplastic cell growth, including tumours of the lung, liver, blood cells, skin, pancreas, stomach, colon, prostate, uterus, breast, lymph glands and bladder. Solid tumours are especially suitable. However, blood cancers, including leukaemias and lymphomas are now also believed to involve new blood vessel formation and may be treated by the methods of the invention.

The invention thus includes a method of combating a disease or condition selected from tumours/cancer, psoriasis, atherosclerosis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation in an individual, the method comprising administering an antibody that selectively binds to the extracellular region of MR to the individual.

By "combating" we include the meaning that the method can be used to alleviate symptoms of the disorder (ie the method is used palliatively), or to treat the disorder, or to prevent the disorder (ie the method is used prophylactically).

Thus, the invention comprises a method of treating a patient who has a disease in which angiogenesis contributes to pathology, the method comprising the step of administering to the patient an antibody that selectively binds to the extracellular region of MR.

Typically, the disease is associated with undesirable neovasculature formation and the treatment reduces this to a useful extent.

The therapy (treatment) may be on humans or animals. Preferably, the methods of the inventions are used to treat humans.

By "antibody" we include not only whole immunoglobulin molecules but also fragments thereof such as Fab, F(ab')2, Fv and other fragments thereof that retain the antigen-binding site. Similarly the term "antibody" includes genetically engineered derivatives of antibodies such as single chain Fv molecules (scFv) and domain antibodies (dAbs). The term also includes antibody-like molecules which may be produced using phage-display techniques or other random selection techniques for molecules which bind to MR or to specified regions of MR. Thus, the term antibody includes all molecules which contain a structure, preferably a peptide structure, which is part of the recognition site (ie the part of the antibody that binds or combines with the epitope or antigen) of a natural antibody.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

By "ScFv molecules" we mean molecules wherein the $V_H$ and $V_L$ partner domains are linked via a flexible oligopeptide. Engineered antibodies, such as ScFv antibodies, can be made using the techniques and approaches described in J. Huston et al., (1988) "Protein engineering of antibody binding sites: recovery of specific activity in an anti-digoxin single chain Fv analogue produced in *E. coli*", *Proc. Natl. Acad. Sci. USA*, 85, pp. 5879-5883, and in A. Pluckthun, (June 1991) "Antibody engineering; Advances from use of *E. coli* expression systems", *Bio/technology vol* 9, incorporated herein by reference.

The advantages of using antibody fragments, rather than whole antibodies, are several-fold. The smaller size of the fragments may lead to improved pharmacological properties, such as better penetration to the target site. Effector functions of whole antibodies, such as complement binding, are removed. Fab, Fv, ScFv and dAb antibody fragments can all be expressed in and secreted from *E. coli*, thus allowing the facile production of large amounts of the fragments.

Whole antibodies, and F(ab')$_2$ fragments are "bivalent". By "bivalent" we mean that the antibodies and F(ab')$_2$ fragments have two antigen combining sites. In contrast, Fab, Fv, ScFv and dAb fragments are monovalent, having only one antigen combining site.

Although the antibody may be a polyclonal antibody, it is preferred if it is a monoclonal antibody. In some circumstance, particularly if the antibody is going to be administered repeatedly to a human patient, it is preferred if the monoclonal antibody is a human monoclonal antibody or a humanised monoclonal antibody.

Suitable monoclonal antibodies which are reactive as described herein may be prepared by known techniques, for example those disclosed in "*Monoclonal Antibodies; A manual of techniques*", H Zola (CRC Press, 1988) and in "*Monoclonal Hybridoma Antibodies: Techniques and Application*", SGR Hurrell (CRC Press, 1982). Polyclonal antibodies may be produced which are polyspecific or monospecific. It is preferred that they are monospecific.

Chimaeric antibodies are discussed by Neuberger et al (1998, 8th *International Biotechnology Symposium* Part 2, 792-799).

It is preferred if the antibody is a humanised antibody. Suitably prepared non-human antibodies can be "humanised" in known ways, for example by inserting the CDR regions of mouse antibodies into the framework of human antibodies. Humanised antibodies can be made using the techniques and approaches described in M. Verhoeyen, C. Milstein and G. Winter (1988) "Reshaping human antibodies: Grafting an antilysozyme activity", *Science*, 239, 1534-1536, and in C. Kettleborough et al., (1991) "Humanisation of a mouse monoclonal antibody by CDR grafting; The importance of framework residues in loop conformation", *Protein Engineering*, 14(7), 773-783, incorporated herein by reference.

The antibodies may be human antibodies in the sense that they have the amino acid sequence of human anti-MR antibodies but they may be prepared using methods known in the art that do not require immunisation of humans. For example, transgenic mice are available which contain, in essence, human immunoglobulin genes (see Vaughan et al (1998) *Nature Biotechnol.* 16, 535-539.

A second aspect of the invention provides use of an antibody that selectively binds to the extracellular region of MR in the preparation of a medicament for inhibiting angiogenesis.

The medicament may be useful in combating any disease or condition involving unwanted or inappropriate angiogenesis. Such conditions include those described above with reference to the first aspect of the invention.

The invention thus includes the use of an antibody that selectively binds to the extracellular region of MR in the preparation of a medicament for combating a disease or condition selected from tumours/cancer, especially solid tumours, psoriasis, atherosclerosis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation.

A third aspect of the invention provides an in vitro method of inhibiting angiogenesis comprising administering an antibody that selectively binds to the extracellular region of MR to tissue or cells in vitro. The cells may be established cell lines, or cells that have been removed from an individual. The tissue or cells are preferably mammalian tissue or cells, and most preferably are human tissue or cells.

In an embodiment of each of the first three aspects of the invention, the antibody selectively binds to the Ig region of MR. The Ig region of MR is located at residues 46-209 of MR (FIG. 3, SEQ ID NO: 4).

In one preferred embodiment, the antibody selectively binds to the IgA domain of MR, which is located at residues 46-116 of MR (FIG. 4A, SEQ ID NO: 5).

In an alternative preferred embodiment, the antibody selectively binds to the IgB domain of MR, which is located at residues 151-209 of MR (FIG. 4B, SEQ ID NO: 6).

In an embodiment of each of the first three aspects of the invention, the antibody has at least one light chain variable region incorporating the following CDRs:

```
CDR1:
SASSSVSYMY            (SEQ ID NO: 9)

CDR2:
LTSNLAS               (SEQ ID NO: 10)

CDR3:
QQWSSNPLT             (SEQ ID NO: 11)
```

In a more specific embodiment, the antibody may have at least one light chain variable region comprising the amino acid sequence:

```
                                          (SEQ ID NO: 12)
QIVLTQSPALMSASPGEKVTMTCSASSSVSYMYWYQQKPRSSPKPWIYL

TSNLASGVPARFSGSGSGTSYSLTISSMEAEDAATYYCQQWSSNPLTFG

AGTKLELK.
```

Preferably, the light chain is a kappa light chain.

In an embodiment of each of the first three aspects of the invention, the antibody has at least one heavy chain variable region incorporating the following CDRs:

```
CDR1:
DYNLN                 (SEQ ID NO: 13)

CDR2:
VINPNYGTTSYNQKFKG     (SEQ ID NO: 14)

CDR3:
GRDYFGY               (SEQ ID NO: 15)
```

In a more specific embodiment, the antibody may have at least one heavy chain variable region comprising the amino acid sequence:

```
                                     (SEQ ID NOs: 16 and 17)
QVK/QLQESGPELVKPGASVKISCKASGYSLTDYNLNWVKQNKGKSLEW

IGVINPNYGTTSYNQKFKGKATLTVDQSSSTTYMQLNSLTSEDSAVYYC

ARGRDYFGYWGQGTTVTVSS,
``` where K/Q means that either K or Q is present at that position (K is present in SEQ ID NO: 16, while Q is present in SEQ ID NO: 17).

In a yet more specific embodiment, the antibody has at least one light chain variable region as defined above and at least one heavy chain variable region as defined above.

A fourth aspect of the invention provides a method of inhibiting angiogenesis in an individual in need thereof comprising administering a polynucleotide encoding an antibody as defined above to the individual.

A fifth aspect of the invention provides the use of a polynucleotide encoding an antibody as defined above in the preparation of a medicament for inhibiting angiogenesis.

A sixth aspect of the invention provides an in vitro method of inhibiting angiogenesis comprising administering a polynucleotide encoding an antibody as defined above to tissue or cells in vitro.

A seventh aspect of the invention provides an antibody that contains the amino acid sequences i) to iii), the amino acid sequences iv) to vi), or preferably the amino acid sequences i) to vi):

```
i)
SASSSVSYMY            (SEQ ID NO: 9)

ii)
LTSNLAS               (SEQ ID NO: 10)

iii)
QQWSSNPLT             (SEQ ID NO: 11)

iv)
DYNLN                 (SEQ ID NO: 13)

v)
VINPNYGTTSYNQKFKG     (SEQ ID NO: 14)

vi)
GRDYFGY.              (SEQ ID NO: 15)
```

While the CDRs that determine specificity of binding to an antigen may be determined empirically, it has been demonstrated that in a significant number of cases the IgH CDR3 is the most important CDR region. The invention thus includes an antibody with an Ig heavy chain CDR3 region having the amino acid sequence GRDYFGY (SEQ ID NO: 15).

Preferably, the antibody selectively binds to the extracellular region of MR (residues 1-467 of MR, FIG. 2B, SEQ ID NO: 3), and the selective binding to MR is conferred by the presence of these amino acid sequences. Preferably, the antibody inhibits a function of MR. Such functions include the inhibition of ligand binding, the interaction with other cell surface molecules and the inhibition of activation of the receptor.

Preferably, the antibody has at least one light chain variable region incorporating the following CDRs:

```
CDR1:
SASSSVSYMY            (SEQ ID NO: 9)

CDR2:
LTSNLAS               (SEQ ID NO: 10)

CDR3:
QQWSSNPLT             (SEQ ID NO: 11)
```

More preferably, the antibody has at least one light chain variable region comprising the amino acid sequence:

```
                                          (SEQ ID NO: 12)
QIVLTQSPALMSASPGEKVTMTCSASSSVSYMYWYQQKPRSSPKPWIYLT

SNLASGVPARFSGSGSGTSYSLTISSMEAEDAATYYCQQWSSNPLTFGAG

TKLELK.
```

Preferably, the light chain is a kappa light chain.

Preferably, the antibody has at least one heavy chain variable region incorporating the following CDRs:

```
CDR1:
DYNLN                       (SEQ ID NO: 13)

CDR2:
VINPNYGTTSYNQKFKG           (SEQ ID NO: 14)

CDR3:
GRDYFGY                     (SEQ ID NO: 15)
```

More preferably, the antibody has at least one heavy chain variable region comprising the amino acid sequence:

```
                            (SEQ ID NOs: 16 and 17)
QVK/QLQESGPELVKPGASVKISCKASGYSLTDYNLNWVKQNKGKSLEWI

GVINPNYGTTSYNQKFKGKATLTVDQSSSTTYMQLNSLTSEDSAVYYCAR

GRDYFGYWGQGTTVTVSS.
```

Yet more preferably, the antibody has at least one light chain variable region as defined above as defined above in the seventh aspect of the invention and at least one heavy chain variable region as defined above in the seventh aspect of the invention.

Most preferably, the antibody has at least one light chain variable region comprising the amino acid sequence:

```
                            (SEQ ID NO: 12)
QIVLTQSPALMSASPGEKVTMTCSASSSVSYMYWYQQKPRSSPKPWIYLTS

NLASGVPARFSGSGSGTSYSLTISSMEAEDAATYYCQQWSSNPLTFGAGTK

LELK
``` and at least one heavy chain variable region comprising the amino acid sequence:

```
                            (SEQ ID NOs: 16 and 17)
QVK/QLQESGPELVKPGASVKISCKASGYSLTDYNLNWVKQNKGKSLEWI

GVINPNYGTTSYNQKFKGKATLTVDQSSSTTYMQLNSLTSEDSAVYYCAR

GRDYFGYWGQGTTVTVSS.
```

It is preferred if the antibody is a humanised antibody.

It is further preferred if the antibody is a humanised antibody having the following CDRs:

```
light chain CDR1:
SASSSVSYMY                  (SEQ ID NO: 9)

light chain CDR2:
LTSNLAS                     (SEQ ID NO: 10)

light chain CDR3:
QQWSSNPLT                   (SEQ ID NO: 11)

heavy chain CDR1:
DYNLN                       (SEQ ID NO: 13)

heavy chain CDR2:
VINPNYGTTSYNQKFKG           (SEQ ID NO: 14)

heavy chain CDR3:
GRDYFGY                     (SEQ ID NO: 15)
```

An eighth aspect of the invention provides an antibody that selectively binds to the MR epitope selectively bound by an antibody having at least one light chain variable region comprising the amino acid sequence:

```
                            (SEQ ID NO: 12)
QIVLTQSPALMSASPGEKVTMTCSASSSVSYMYWYQQKPRSSPKPWIYLTS

NLASGVPARFSGSGSGTSYSLTISSMEAEDAATYYCQQWSSNPLTFGAGTK

LELK
``` and at least one heavy chain variable region comprising the amino acid sequence:

```
                            (SEQ ID NOs: 16 and 17)
QVK/QLQESGPELVKPGASVKISCKASGYSLTDYNLNWVKQNKGKSLEWI

GVINPNYGTTSYNQKFKGKATLTVDQSSSTTYMQLNSLTSEDSAVYYCAR

GRDYFGYWGQGTTVTVSS.
```

By an antibody that selectively binds to an MR epitope selectively bound by another defined antibody, we include an antibody that competes with the defined antibody. Such antibodies can be determined, for example, using competitive binding assays, preferably high throughput binding assays, as are well known to a person of skill in the art. Suitable assays include a cross-competition ELISA in which an extracellular fragment of MR is incubated with the defined antibody and a test antibody, to determine whether or not the test antibody competes with the defined antibody for binding to the MR epitope.

A ninth aspect of the invention provides a polynucleotide encoding an antibody as defined in the seventh or eighth aspects of the invention.

In an embodiment, the polynucleotide comprises at least one of the nucleotide sequences:

```
i)
AGT GCC AGC TCA AGT GTA AGT TAC ATG   (SEQ ID NO: 18)
TAC ii)
TGT CAC ATC CAA CCT GGC TTC T         (SEQ ID NO: 19)

iii)
CAG CAG TGG AGT AGT AAC CCA CTC ACG   (SEQ ID NO: 20)
```

Preferably, the polynucleotide comprises two or all three of the nucleotide sequences i), ii) and iii).

Preferably, the polynucleotide comprises the nucleotide sequence:

```
                                      (SEQ ID NO: 21)
CAA ATT GTT CTC ACC CAG TCT CCA GCA CTC ATG TCT

GCA TCT CCA GGG GAG AAG GTC ACC ATG ACC TGC AGT

GCC AGC TCA AGT GTA AGT TAC ATG TAC TGG TAC CAG

CAG AAG CCA AGA TCC TCC CCC AAA CCC TGG ATT TAT

CTC ACA TCC AAC CTG GCT TCT GGA GTC CCT GCT CGC

TTC AGT GGC AGT GGG TCT GGG ACC TCT TAC TCT CTC

ACA ATC AGC AGC ATG GAG GCT GAA GAT GCT GCC ACT

TAT TAC TGC CAG CAG TGG AGT AGT AAC CCA CTC ACG

TTC GGT GCT GGG ACC AAG CTG GAG CTG AAA.
```

In an alternative or additional embodiment, the polynucleotide comprises at least one of the nucleotide sequences:

iv)
GAC TAC AAC CTG AAC                          (SEQ ID NO: 22)

v)
GTA ATT AAT CCA AAC TAT GGT ACT AGT          (SEQ ID NO: 23)
TAC AAT CAG AAG TTC AAG GGC,
and vi)
GGG AGG GAT TAC TTC GGC TAC                  (SEQ ID NO: 24)

Preferably, the polynucleotide comprises two or all three of the nucleotide sequences iv), v) and vi).

Preferably, the polynucleotide comprises the nucleotide sequence:

CAG GTC AAG(or A/CAA) CTG CAG GAG TCA GGA CCT GAG

CTG GTG AAG CCT GGC GCT TCA GTG AAG ATA TCC TGC

AAG GCT TCT GGT TAC TCA CTC ACT GAC TAC AAC CTG

AAC TGG GTG AAG CAG AAC AAA GGA AAG AGC CTT GAG

TGG ATT GGA GTA ATT AAT CCA AAC TAT GGT ACT AGT

TAC AAT CAG AAG TTC AAG GGC AAG GCC ACA TTG ACT

GTA GAC CAA TCT TCC AGC ACA ACC TAC ATG CAG CTC

AAC AGC CTG ACA TCT GAG GAC TCT GCA GTC TAT TAC

TGT GCA AGA GGG AGG GAT TAC TTC GGC TAC TGG GGC

CAA GGG ACC ACG GTC ACC GTC TCC TCA.

(The polynucleotide having AAG in the third codon is SEQ ID NO: 25; the polynucleotide having AAA in the third codon is SEQ ID NO: 26; and the polynucleotide having CAA in the third codon is SEQ ID NO: 27).

Most preferably, the polynucleotide comprises at least one nucleotide sequence:

(SEQ ID NO: 21)
CAA ATT GTT CTC ACC CAG TCT CCA GCA CTC ATG TCT

GCA TCT CCA GGG GAG AAG GTC ACC ATG ACC TGC AGT

GCC AGC TCA AGT GTA AGT TAC ATG TAC TGG TAC CAG

CAG AAG CCA AGA TCC TCC CCC AAA CCC TGG ATT TAT

CTC ACA TCC AAC CTG GCT TCT GGA GTC CCT GCT CGC

TTC AGT GGC AGT GGG TCT GGG ACC TCT TAC TCT CTC

ACA ATC AGC AGC ATG GAG GCT GAA GAT GCT GCC ACT

TAT TAC TGC CAG CAG TGG AGT AGT AAC CCA CTC ACG

TTC GGT GCT GGG ACC AAG CTG GAG CTG AAA, and at least one nucleotide sequence:

(SEQ ID NOs: 25-27)
CAG GTC AAG(or A/CAA) CTG CAG GAG TCA GGA CCT GAG

CTG GTG AAG CCT GGC GCT TCA GTG AAG ATA TCC TGC

AAG GCT TCT GGT TAC TCA CTC ACT GAC TAC AAC CTG

AAC TGG GTG AAG CAG AAC AAA GGA AAG AGC CTT GAG

TGG ATT GGA GTA ATT AAT CCA AAC TAT GGT ACT AGT

TAC AAT CAG AAG TTC AAG GGC AAG GCC ACA TTG ACT

GTA GAC CAA TCT TCC AGC ACA ACC TAC ATG CAG CTC

AAC AGC CTG ACA TCT GAG GAC TCT GCA GTC TAT TAC

TGT GCA AGA GGG AGG GAT TAC TTC GGC TAC TGG GGC

CAA GGG ACC ACG GTC ACC GTC TCC TCA.

In an embodiment, the two coding regions may be on the same polynucleotide, for example on a polynucleotide for expression of a ScFv antibody.

A tenth aspect of the invention provides an antibody that selectively binds the Ig region of MR (residues 46-209, SEQ ID NO: 4) but which does not selectively bind to the peptide LLQPPARGHAHDGQALSTDL (residues 91-109 of MR, SEQ ID NO: 28) or to the peptide LSQSPGAVPQALVAWRA (residues 165-181 of MR, SEQ ID NO: 29).

In an embodiment, the invention includes an antibody that selectively binds the IgA region of MR (residues 46-116, SEQ ID NO: 5) but does not selectively bind to the peptide LLQPPARGHAHDGQALSTDL (residues 91-109 of MR, SEQ ID NO: 28).

In an alternative embodiment, the invention includes an antibody that to selectively binds the IgB region of MR (residues 151-209, SEQ ID NO: 6) but does not selectively bind to the peptide LSQSPGAVPQALVAWRA (residues 165-181 of MR, SEQ ID NO: 29).

An eleventh aspect of the invention provides a polynucleotide that encodes an antibody as defined in the tenth aspect of the invention.

A twelfth aspect of the invention provides a compound comprising an antibody as defined above in the seventh, eighth and tenth aspects of the invention, and a cytotoxic moiety.

The cytotoxic moiety is preferably directly or indirectly toxic to cells in neovasculature or cells which are in close proximity to and associated with neovasculature.

By "directly cytotoxic" we include the meaning that the moiety is one which on its own is cytotoxic. By "indirectly cytotoxic" we include the meaning that the moiety is one which, although is not itself cytotoxic, can induce cytotoxicity, for example by its action on a further molecule or by further action on it.

In one embodiment the cytotoxic moiety is a cytotoxic chemotherapeutic agent. Cytotoxic chemotherapeutic agents are well known in the art.

Cytotoxic chemotherapeutic agents, such as anticancer agents, include: alkylating agents including nitrogen mustards such as mechlorethamine (HN$_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin). Natural Products including vinca alkaloids such as vinblastine (VLB) and vincristine; epipodophyllotoxins such as etoposide and teniposide; antibiotics such as dactinomycin (actinomycin D), daunorubicin (daunomycin;

rubidomycin), doxorubicin, bleomycin, plicamycin (mithramycin) and mitomycin (mitomycin C); enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; and hormone agonists/antagonists such as flutamide and tamoxifen.

Various of these agents have previously been attached to antibodies and other target site-delivery agents, and so compounds of the invention comprising these agents may readily be made by the person skilled in the art. For example, carbodiimide conjugation (Bauminger & Wilchek (1980) *Methods Enzymol.* 70, 151-159; incorporated herein by reference) may be used to conjugate a variety of agents, including doxorubicin, to antibodies.

Carbodiimides comprise a group of compounds that have the general formula R—N═C═N—RN, where R and RN can be aliphatic or aromatic, and are used for synthesis of peptide bonds. The preparative procedure is simple, relatively fast, and is carried out under mild conditions. Carbodiimide compounds attack carboxylic groups to change them into reactive sites for free amino groups.

The water soluble carbodiimide, 1-ethyl-3-(3-dimethylaminopropyl) carbodiimide (EDC) is particularly useful for conjugating a functional moiety to an antibody and may be used to conjugate doxorubicin to tumor homing peptides. The conjugation of doxorubicin and an antibody requires the presence of an amino group, which is provided by doxorubicin, and a carboxyl group, which is provided by the antibody such as an antibody or peptide.

In addition to using carbodiimides for the direct formation of peptide bonds, EDC also can be used to prepare active esters such as N-hydroxysuccinimide (NHS) ester. The NHS ester, which binds only to amino groups, then can be used to induce the formation of an amide bond with the single amino group of the doxorubicin. The use of EDC and NHS in combination is commonly used for conjugation in order to increase yield of conjugate formation (Bauminger & Wilchek, supra, 1980).

Other methods for conjugating a cytotoxic moiety to an antibody can also be used. For example, sodium periodate oxidation followed by reductive alkylation of appropriate reactants can be used, as can glutaraldehyde cross-linking. However, it is recognised that, regardless of which method of producing a compound of the invention is selected, a determination must be made that the antibody maintains its targeting ability and that the attached moiety maintains its relevant function.

In a further embodiment of the invention, the cytotoxic moiety is a cytotoxic peptide or polypeptide moiety by which we include any moiety which leads to cell death. Cytotoxic peptide and polypeptide moieties are well known in the art and include, for example, ricin, abrin, *Pseudomonas* exotoxin, tissue factor and the like. Methods for linking them to targeting moieties such as antibodies are also known in the art. The use of ricin as a cytotoxic agent is described in Burrows & Thorpe (1993) *Proc. Natl. Acad. Sci. USA* 90, 8996-9000, incorporated herein by reference, and the use of tissue factor, which leads to localised blood clotting and infarction of a tumour, has been described by Ran et al (1998) *Cancer Res.* 58, 4646-4653 and Huang et al (1997) *Science* 275, 547-550. Tsai et al (1995) *Dis. Colon Rectum* 38, 1067- 1074 describes the abrin A chain conjugated to a monoclonal antibody and is incorporated herein by reference. Other ribosome inactivating proteins are described as cytotoxic agents in WO 96/06641. *Pseudomonas* exotoxin may also be used as the cytotoxic polypeptide moiety (see, for example, Aiello et al (1995) *Proc. Natl. Acad. Sci. USA* 92, 10457-10461; incorporated herein by reference).

Certain cytokines, such as TNFα and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the compound of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the antibody in known ways. For example EDTA or another chelating agent may be attached to the antibody and used to attach $^{111}$In or $^{90}$Y. Tyrosine residues may be labelled with $^{125}$I or $^{131}$I.

The cytotoxic moiety may be a suitable indirectly cytotoxic polypeptide. In a particularly preferred embodiment, the indirectly cytotoxic polypeptide is a polypeptide which has enzymatic activity and can convert a relatively non-toxic prodrug into a cytotoxic drug. When the targeting moiety is an antibody this type of system is often referred to as ADEPT (Antibody-Directed Enzyme Prodrug Therapy). The system requires that the targeting moiety locates the enzymatic portion to the desired site in the body of the patient (ie the site expressing MR, such as new vascular tissue associated with a tumour) and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues (see Senter, P. D. et al (1988) "Anti-tumor effects of antibody-alkaline phosphatase conjugates in combination with etoposide phosphate" *Proc. Natl. Acad. Sci. USA* 85, 4842-4846; Bagshawe (1987) *Br. J. Cancer* 56, 531-2; and Bagshawe, K. D. et al (1988) "A cytotoxic agent can be generated selectively at cancer sites" *Br. J. Cancer.* 58, 700-703.)

The cytotoxic substance may be any existing anti-cancer drug such as an alkylating agent; an agent which intercalates in DNA; an agent which inhibits any key enzymes such as dihydrofolate reductase, thymidine synthetase, ribonucleotide reductase, nucleoside kinases or topoisomerase; or an agent which effects cell death by interacting with any other cellular constituent. Etoposide is an example of a topoisomerase inhibitor.

Reported prodrug systems include: a phenol mustard prodrug activated by an *E. coli* β-glucuronidase (Wang et al, 1992 and Roffler et al, 1991); a doxorubicin prodrug activated by a human β-glucuronidase (Bosslet et al, 1994); further doxorubicin prodrugs activated by coffee bean α-galactosidase (Azoulay et al, 1995); daunorubicin prodrugs, activated by coffee bean α-D-galactosidase (Gesson et al, 1994); a 5-fluorouridine prodrug activated by an *E. coli* β-D-galactosidase (Abraham et al, 1994); and methotrexate prodrugs (eg methotrexate-alanine) activated by carboxypeptidase A (Kuefner et al, 1990, Vitols et al, 1992 and Vitols et al, 1995). These and others are included in Table 1.

TABLE 1

| Enzyme | Prodrug |
| --- | --- |
| Carboxypeptidase G2 | Derivatives of L-glutamic acid and benzoic acid mustards, aniline mustards, phenol mustards and phenylenediamine mustards; fluorinated derivatives of these |
| Alkaline phosphatase | Etoposide phosphate<br>Mitomycin phosphate |
| Beta-glucuronidase | p-Hydroxyaniline mustard-glucuronide<br>Epirubicin-glucuronide |
| Penicillin-V-amidase | Adriamycin-N phenoxyacetyl |
| Penicillin-G-amidase | N-(4'-hydroxyphenyl acetyl) palytoxin<br>Doxorubicin and melphalan |
| Beta-lactamase | Nitrogen mustard-cephalosporin p-phenylenediamine; doxorubicin derivatives; vinblastine derivative-cephalosporin, cephalosporin mustard; a taxol derivative |
| Beta-glucosidase | Cyanophenylmethyl-beta-D-gluco-pyranosiduronic acid |
| Nitroreductase | 5-(Azaridin-1-yl-)-2,4-dinitrobenzamide |
| Cytosine deaminase | 5-Fluorocytosine |
| Carboxypeptidase A | Methotrexate-alanine |

(This table is adapted from Bagshawe (1995) *Drug Dev. Res.* 34, 220-230, from which full references for these various systems may be obtained; the taxol derivative is described in Rodrigues, M. L. et al (1995) *Chemistry & Biology* 2, 223).

Suitable enzymes for forming part of the enzymatic portion of the invention include: exopeptidases, such as carboxypeptidases G, G1 and G2 (for glutamylated mustard prodrugs), carboxypeptidases A and B (for MTX-based prodrugs) and aminopeptidases (for 2-α-aminocyl MTC prodrugs); endopeptidases, such as eg thrombolysin (for thrombin prodrugs); hydrolases, such as phosphatases (eg alkaline phosphatase) or sulphatases (eg aryl sulphatases) (for phosphylated or sulphated prodrugs); amidases, such as penicillin amidases and arylacyl amidase; lactamases, such as β-lactamases; glycosidases, such as β-glucuronidase (for β-glucuronomide anthracyclines), α-galactosidase (for amygdalin) and β-galactosidase (for β-galactose anthracycline); deaminases, such as cytosine deaminase (for 5FC); kinases, such as urokinase and thymidine kinase (for gancyclovir); reductases, such as nitroreductase (for CB1954 and analogues), azoreductase (for azobenzene mustards) and DT-diaphorase (for CB1954); oxidases, such as glucose oxidase (for glucose), xanthine oxidase (for xanthine) and lactoperoxidase; DL-racemases, catalytic antibodies and cyclodextrins.

The prodrug is relatively non-toxic compared to the cytotoxic drug. Typically, it has less than 10% of the toxicity, preferably less than 1% of the toxicity as measured in a suitable in vitro cytotoxicity test.

It is likely that the moiety which is able to convert a prodrug to a cytotoxic drug will be active in isolation from the rest of the compound but it is necessary only for it to be active when (a) it is in combination with the rest of the compound and (b) the compound is attached to, adjacent to or internalised in target cells.

When each moiety of the compound is a polypeptide, the two portions may be linked together by any of the conventional ways of cross-linking polypeptides, such as those generally described in O'Sullivan et al (1979) *Anal. Biochem.* 100, 100-108. For example, the anti-MR antibody may be enriched with thiol groups and the further moiety reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Alternatively, the compound may be produced as a fusion compound by recombinant DNA techniques whereby a length of DNA comprises respective regions encoding the two moieties of the compound of the invention either adjacent one another or separated by a region encoding a linker peptide which does not destroy the desired properties of the compound. Conceivably, the two portions of the compound may overlap wholly or partly.

The DNA is then expressed in a suitable host to produce a polypeptide comprising the compound of the invention.

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole (see, for example, McGinn et al (1996) *J. Natl. Cancer Inst.* 88, 1193-11203; Shewach & Lawrence (1996) *Invest. New Drugs* 14, 257-263; Horsman (1995) *Acta Oncol.* 34, 571-587; Shenoy & Singh (1992) *Clin. Invest.* 10, 533-551; Mitchell et al (1989) *Int. J. Radiat. Biol.* 56, 827-836; Iliakis & Kurtzman (1989) *Int. J. Radiat. Oncol. Biol. Phys.* 16, 1235-1241; Brown (1989) *Int. J. Radiat. Oncol. Biol. Phys.* 16, 987-993; Brown (1985) *Cancer* 55, 2222-2228).

Also, delivery of genes into cells can radiosensitise them, for example delivery of the p53 gene or cyclin D (Lang et al (1998) *J. Neurosurg.* 89, 125-132; Coco Martin et al (1999) *Cancer Res.* 59, 1134-1140).

The further moiety may be one which becomes cytotoxic, or releases a cytotoxic moiety, upon irradiation. For example, the boron-10 isotope, when appropriately irradiated, releases a particles which are cytotoxic (see for example, U.S. Pat. No. 4,348,376 to Goldenberg; Primus et al (1996) *Bioconjug. Chem.* 7, 532-535).

Similarly, the cytotoxic moiety may be one which is useful in photodynamic therapy such as photofrin (see, for example, Dougherty et al (1998) *J. Natl. Cancer Inst.* 90, 889-905).

The cytotoxic moiety may be a nucleic acid molecule which is directly or indirectly cytotoxic. For example, the nucleic acid molecule may be an antisense oligonucleotide which, upon localisation at the target site is able to enter cells and lead to their death. The oligonucleotide, therefore, may be one which prevents expression of an essential gene, or one which leads to a change in gene expression which causes apoptosis.

Examples of suitable oligonucleotides include those directed at bcl-2 (Ziegler et al (1997) *J. Natl. Cancer Inst.* 89, 1027-1036), and DNA polymerase a and topoisomerase IIa (Lee et al (1996) *Anticancer Res.* 16, 1805-1811.

Peptide nucleic acids may be useful in place of conventional nucleic acids (see Knudsen & Nielsen (1997) *Anticancer Drugs* 8, 113-118).

A thirteenth aspect of the invention provides a polynucleotide encoding a compound as defined above in the twelfth aspect of the invention, wherein the antibody and the cytotoxic moiety are polypeptides which are fused.

A fourteenth aspect of the invention provides a compound comprising an antibody as defined above in the seventh, eighth and tenth aspects of the invention, and a readily detectable moiety.

A compound comprising an anti-MR antibody as defined above and a readily detectable moiety can be used, in combination with an appropriate detection method, to detect the location of the compound in the individual, and hence to identify the sites and extent of angiogenesis in the individual, as well as inhibiting the angiogenesis in the individual.

By a "readily detectable moiety" we include the meaning that the moiety is one which, when located at the target site following administration of the compound of the invention into a patient, may be detected, typically non-invasively from outside the body and the site of the target located. Thus, the compounds of this embodiment of the invention are useful in imaging and diagnosis.

Typically, the readily detectable moiety is or comprises a radioactive atom which is useful in imaging. Suitable radioactive atoms include technetium-99m or iodine-123 for scintigraphic studies. Other readily detectable moieties include, for example, spin labels for magnetic resonance imaging (MRI) such as iodine-123 again, iodine-131, indium-111, fluorine-19, carbon-13, nitrogen-15, oxygen-17, gadolinium, manganese or iron. Clearly, the compound of the invention must have sufficient of the appropriate atomic isotopes in order for the molecule to be readily detectable.

The radio- or other labels may be incorporated in the compound of the invention in known ways. For example, if the antibody is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the antibody. Yttrium-90 can be attached via a lysine residue. The IODOGEN method (Fraker er al (1978) *Biochem. Biophys. Res. Comm.* 80, 49-57) can be used to incorporate iodine-123. Reference ("Monoclonal Antibodies in Immunoscintigraphy", J-F Chatal, CRC Press, 1989) describes other methods in detail.

A fifteenth aspect of the invention provides a vector comprising a polynucleotide as defined above in the ninth, eleventh and thirteenth aspects of the invention.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. An example of an inducible mammalian expression vector is pMSG, also available from Pharmacia (Piscataway, N.J., USA). This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

Methods well known to those skilled in the art can be used to construct expression vectors containing the coding sequence and, for example appropriate transcriptional or translational controls. One such method involves ligation via homopolymer tails. Homopolymer polydA (or polydC) tails are added to exposed 3'-OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic molecules called linkers and adaptors. DNA fragments with blunt ends are generated by bacteriophage T4 DNA polymerase or *E. coli* DNA polymerase I which remove protruding 3' termini and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487-491. In this method the DNA to be enzymatically amplified is flanked by two specific oligonucleotide primers which themselves become incorporated into the amplified DNA. The specific primers may contain restriction endonuclease recognition sites which can be used for cloning into expression vectors using methods known in the art.

A sixteenth aspect of the invention provides a host cell comprising a polynucleotide as defined in the ninth, eleventh and thirteenth aspects of the invention, or a vector as defined in the fifteenth aspect of the invention.

Many expression systems are known, including systems employing: bacteria (eg. *E. coli* and *Bacillus subtilis*) transformed with, for example, recombinant bacteriophage, plasmid or cosmid DNA expression vectors; yeasts (eg. *Saccharomyces cerevisiae*) transformed with, for example, yeast expression vectors; insect cell systems transformed with, for example, viral expression vectors (eg. baculovirus); plant cell systems transfected with, for example viral or bacterial expression vectors; animal cell systems transfected with, for example, adenovirus expression vectors.

The vectors can include a prokaryotic replicon, such as the Col E1 ori, for propagation in a prokaryote, even if the vector is to be used for expression in other, non-prokaryotic cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

The polynucleotide in a suitable host cell may be expressed to produce the antibody or compound of the invention. Thus, the polynucleotide may be used in accordance with known techniques, appropriately modified in view of the teachings contained herein, to construct an expression vector, which is then used to transform an appropriate host cell for the expression and production of the antibody or compound of the invention. Such techniques include those disclosed in U.S. Pat. Nos. 4,440,859 issued 3 Apr. 1984 to Rutter et al, 4,530,901 issued 23 Jul. 1985 to Weissman, 4,582,800 issued 15 Apr. 1986 to Crowl, 4,677,063 issued 30 Jun. 1987 to Mark et al, 4,678,751 issued 7 Jul. 1987 to Goeddel, 4,704,362 issued 3 Nov. 1987 to Itakura et al, 4,710,463 issued 1 Dec. 1987 to Murray, 4,757,006 issued 12 Jul. 1988 to Toole, Jr. et al, 4,766,075 issued 23 Aug. 1988 to Goeddel et al and 4,810,648 issued 7 Mar. 1989 to Stalker, all of which are incorporated herein by reference.

The polynucleotide may be joined to a wide variety of other DNA sequences for introduction into an appropriate host. The companion DNA will depend upon the nature of the host, the manner of the introduction of the DNA into the host, and whether episomal maintenance or integration is desired.

Generally, the polynucleotide is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. Thus, the DNA insert may be operatively linked to an appropriate promoter. Bacterial promoters include the *E. coli* lad and lacZ promoters, the T3 and T7 promoters, the gpt promoter, the phage λ PR and PL promoters, the phoA promoter and the trp promoter. Eukaryotic promoters include the CMV immediate early promoter, the HSV thymidine kinase promoter, the early and late SV40 promoters and the promoters of retroviral LTRs. Other suitable promoters will be known to the skilled artisan. The expression constructs will desirably also contain sites for transcription initiation and termination, and in the transcribed region, a ribosome binding site for translation. (Hastings et al, International Patent No. WO 98/16643, published 23 Apr. 1998)

The vector is then introduced into the host through standard techniques. Generally, not all of the hosts will be transformed by the vector and it will therefore be necessary to select for transformed host cells. One selection technique involves incorporating into the expression vector a DNA sequence marker, with any necessary control elements, that codes for a selectable trait in the transformed cell. These markers include dihydrofolate reductase, G418 or neomycin resistance for eukaryotic cell culture, and tetracyclin, kanamycin or ampicillin resistance genes for culturing in *E. coli* and other bacteria. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

The antibody or compound can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

An seventeenth aspect of the invention provides a stable host cell line producing an antibody as defined in the seventh, eighth or tenth aspects of the invention, or a compound as defined in the twelfth aspect of the invention wherein the antibody and the cytotoxic moiety are polypeptides which are fused, resulting from incorporation in the cell line an exogenous polynucleotide as defined in the ninth, eleventh and thirteenth aspects of the invention, or a vector as defined in the fifteenth aspect of the invention.

A eighteenth aspect of the invention provides a pharmaceutical composition or formulation comprising an antibody as defined in the seventh, eighth or tenth aspects of the invention, or a polynucleotide as defined in the ninth, eleventh and thirteenth aspects of the invention, or a compound as defined in the twelfth or fourteenth aspects of the invention, and a pharmaceutically acceptable carrier.

By "pharmaceutically acceptable" is included that the formulation is sterile and pyrogen free. Suitable pharmaceutical carriers are well known in the art of pharmacy.

The carrier(s) must be "acceptable" in the sense of being compatible with the compound of the invention and not deleterious to the recipients thereof. Typically, the carriers will be water or saline which will be sterile and pyrogen free; however, other acceptable carriers may be used.

In an embodiment, the pharmaceutical compositions or formulations of the invention are for parenteral administration, more particularly for intravenous administration.

In a preferred embodiment, the pharmaceutical composition is suitable for intravenous administration to a patient, for example by injection.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

In an alternative preferred embodiment, the pharmaceutical composition is suitable for topical administration to a patient.

Preferably, the formulation is a unit dosage containing a daily dose or unit, daily sub-dose or an appropriate fraction thereof, of the active ingredient.

The antibody, polynucleotide or compound of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the antibody, polynucleotide or compound of the invention can be administered alone but will generally be administered in admixture with a suitable pharmaceutical excipient, diluent or carrier selected with regard to the intended route of administration and standard pharmaceutical practice.

For example, the antibody, polynucleotide or compound of the invention can be administered orally, buccally or sublingually in the form of tablets, capsules, ovules, elixirs, solutions or suspensions, which may contain flavouring or colouring agents, for immediate-, delayed- or controlled-release applications. The antibody, polynucleotide or compound of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin is capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The antibody, polynucleotide or compound of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the antibody, polynucleotide or compound of the invention will usually be from 1 to 1000 mg per adult (i.e. from about 0.015 to 15 mg/kg), administered in single or divided doses.

Thus, for example, the tablets or capsules of the antibody, polynucleotide or compound of the invention may contain from 1 mg to 1000 mg of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The antibody, polynucleotide or compound of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains at least 1 mg of an antibody, polynucleotide or compound of the invention for delivery to the patient. It will be appreciated that he overall daily dose with an aerosol will vary from patient to patient, and may be administered in a single dose or, more usually, in divided doses throughout the day.

Alternatively, the antibody, polynucleotide or compound of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the antibody, polynucleotide or compound of the invention can be formulated as micronised suspensions in isotonic, pH adjusted, sterile saline, or, preferably, as solutions in isotonic, pH adjusted, sterile saline, optionally in combination with a preservative such as a to benzylalkonium chloride. Alternatively, they may be formulated in an ointment such as petrolatum.

For application topically to the skin, the antibody, polynucleotide or compound of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

For veterinary use, a compound of the invention is administered as a suitably acceptable formulation in accordance with normal veterinary practice and the veterinary surgeon will determine the dosing regimen and route of administration which will be most appropriate for a particular animal.

A nineteenth aspect of the invention provides an antibody as defined in the seventh, eighth or tenth aspects of the invention, or a polynucleotide as defined in the ninth, eleventh and thirteenth aspects of the invention, or a compound as defined in the twelfth or fourteenth aspects of the invention, for use in medicine.

A twentieth aspect of the invention provides the use of an antibody as defined in the seventh, eighth, or tenth aspects of the invention, or a polynucleotide as defined in the ninth, eleventh and thirteenth aspects of the invention, or a compound as defined in the twelfth or fourteenth aspects of the invention, in the preparation of a medicament for inhibiting angiogenesis.

Conditions which involve unwanted or undesirable angiogenesis are described above.

A twenty-first aspect of the invention provides a method of inhibiting angiogenesis in an individual in need thereof comprising administering an antibody as defined in the seventh, eighth, or tenth aspects of the invention, or a polynucleotide as defined in the ninth, eleventh and thirteenth aspects of the invention, or a compound as defined in the twelfth or fourteenth aspects of the invention, to the individual.

In an embodiment, polypeptides, such as antibodies, may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The polypeptide can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of polypeptides. A device which delivers a pulsed electric field to cells increases the permeability of the cell membranes to the drug, resulting in a significant enhancement of intracellular drug delivery.

Polypeptides can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of polypeptide delivery is the ReGel injectable system that is thermo-sensitive. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Polypeptide pharmaceuticals can also be delivered orally. The process employs a natural process for oral uptake of vitamin $B_{12}$ in the body to co-deliver proteins and peptides. By riding the vitamin $B_{12}$ uptake system, the protein or peptide can move through the intestinal wall. Complexes are synthesised between vitamin $B_{12}$ analogues and the drug that retain both significant affinity for intrinsic factor (IF) in the vitamin $B_{12}$ portion of the complex and significant bioactivity of the drug portion of the complex.

Polynucleotides may be administered by any effective method, for example, parenterally (eg intravenously, subcutaneously, intramuscularly) or by oral, nasal or other means which permit the oligonucleotides to access and circulate in the patient's bloodstream. Polynucleotides administered systemically preferably are given in addition to locally administered polynucleotides, but also have utility in the absence of local administration. A dosage in the range of from about 0.1 to about 10 grams per administration to an adult human generally will be effective for this purpose.

The polynucleotide may be administered as a suitable genetic construct as is described below and delivered to the patient where it is expressed. Typically, the polynucleotide in the genetic construct is operatively linked to a promoter which can express the antibody or compound in the cell.

Although genetic constructs for delivery of polynucleotides can be DNA or RNA it is preferred if it is DNA.

Preferably, the genetic construct is adapted for delivery to a human cell.

Means and methods of introducing a genetic construct into a cell in an animal body are known in the art. For example, the constructs of the invention may be introduced into cells by any convenient method, for example methods involving retroviruses, so that the construct is inserted into the genome of the cell. For example, in Kuriyama et al (1991) *Cell Struc. and Func.* 16, 503-510 purified retroviruses are administered. Retroviral DNA constructs comprising a polynucleotide as described above may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a neo$^R$ gene). Independent colonies are isolated and expanded and the culture supernatant removed, filtered through a 0.45 µm pore-size filter and stored at -70° C. For the introduction of the retrovirus into the tumour cells, it is convenient to inject directly retroviral supernatant to which 10 µg/ml Polybrene has been added. For tumours exceeding 10 mm in diameter it is appropriate to inject between 0.1 ml and 1 ml of retroviral supernatant; preferably 0.5 ml.

Alternatively, as described in Culver et al (1992) *Science* 256, 1550-1552, cells which produce retroviruses are injected. The retrovirus-producing cells so introduced are engineered to actively produce retroviral vector particles so that continuous productions of the vector occurred within the tumour mass in situ. Thus, proliferating epidermal cells can be successfully transduced in vivo if mixed with retroviral vector-producing cells.

Targeted retroviruses are also available for use in the invention; for example, sequences conferring specific binding affinities may be engineered into pre-existing viral env genes (see Miller & Vile (1995) *Faseb J.* 9, 190-199 for a review of this and other targeted vectors for gene therapy).

Other methods involve simple delivery of the construct into the cell for expression therein either for a limited time or, following integration into the genome, for a longer time. An example of the latter approach includes liposomes (Nassander et al (1992) *Cancer Res.* 52, 646-653).

For the preparation of immuno-liposomes MPB-PE (N-[4-(p-maleimidophenyl)butyryl]-phosphatidylethanolamine) is synthesised according to the method of Martin & Papahadjopoulos (1982) *J. Biol. Chem.* 257, 286-288. MPB-PE is incorporated into the liposomal bilayers to allow a covalent coupling of the antibody, or fragment thereof, to the liposomal surface. The liposome is conveniently loaded with the DNA or other genetic construct of the invention for delivery to the target cells, for example, by forming the said liposomes in a solution of the DNA or other genetic construct, followed by sequential extrusion through polycarbonate membrane filters with 0.6 µm and 0.2 µm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C.

under constant end over end rotation overnight. The immunoliposomes are separated from unconjugated antibodies by ultracentrifugation at 80 000×g for 45 min. Immunoliposomes may be injected intraperitoneally or directly into a tumour.

Other methods of delivery include adenoviruses carrying external DNA via an antibody-polylysine bridge (see Curiel Prog. Med. Virol. 40, 1-18) and transferrin-polycation conjugates as carriers (Wagner et al (1990) Proc. Natl. Acad. Sci. USA 87, 3410-3414). In the first of these methods a polycation-antibody complex is formed with the DNA construct or other genetic construct of the invention, wherein the antibody is specific for either wild-type adenovirus or a variant adenovirus in which a new epitope has been introduced which binds the antibody. The polycation moiety binds the DNA via electrostatic interactions with the phosphate backbone. The adenovirus, because it contains unaltered fibre and penton proteins, is internalised into the cell and carries into the cell with it the DNA construct of the invention. It is preferred if the polycation is polylysine.

The polynucleotide may also be delivered by adenovirus wherein it is present within the adenovirus particle, for example, as described below.

In an alternative method, a high-efficiency nucleic acid delivery system that uses receptor-mediated endocytosis to carry DNA macromolecules into cells is employed. This is accomplished by conjugating the iron-transport protein transferrin to polycations that bind nucleic acids. Human transferrin, or the chicken homologue conalbumin, or combinations thereof is covalently linked to the small DNA-binding protein protamine or to polylysines of various sizes through a disulfide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs of the invention are supplied to the tumour cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et al (1992) Proc. Natl. Acad. Sci. USA 89, 6094-6098 may also be used. This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle.

This approach has the advantages that there is no need to use complex retroviral constructs; there is no permanent modification of the genome as occurs with retroviral infection; and the targeted expression system is coupled with a targeted delivery system, thus reducing toxicity to other cell types.

It will be appreciated that "naked DNA" and DNA complexed with cationic and neutral lipids may also be useful in introducing the DNA of the invention into cells of the individual to be treated. Non-viral approaches to gene therapy are described in Ledley (1995) Human Gene Therapy 6, 1129-1144.

Alternative targeted delivery systems are also known such as the modified adenovirus system described in WO 94/10323 wherein, typically, the DNA is carried within the adenovirus, or adenovirus-like, particle. Michael et al (1995) Gene Therapy 2, 660-668 describes modification of adenovirus to add a cell-selective moiety into a fibre protein. Mutant adenoviruses which replicate selectively in p53-deficient human tumour cells, such as those described in Bischoff et al (1996) Science 274, 373-376 are also useful for delivering the genetic construct of the invention to a cell. Thus, it will be appreciated that a further aspect of the invention provides a virus or virus-like particle comprising a genetic construct of the invention. Other suitable viruses, viral vectors or virus-like particles include lentivirus and lentiviral vectors, HSV, adeno-assisted virus (AAV) and AAV-based vectors, vaccinia and parvovirus.

The genetic constructs of the invention can be prepared using methods well known in the art.

A twenty-second aspect of the invention provides an in vitro method of inhibiting angiogenesis comprising administering an antibody as defined in the seventh, eighth, or tenth aspects of the invention, or a polynucleotide as defined in the ninth, eleventh and thirteenth aspects of the invention, or a compound as defined in the twelfth or fourteenth aspects of the invention, to tissue or cells in vitro.

A twenty-third aspect of the invention provides a method of producing an antibody as defined in the seventh, eighth or tenth aspects of the invention, or a compound as defined in the twelfth aspect of the invention wherein the antibody and the cytotoxic moiety are polypeptides which are fused, the method comprising expressing a polynucleotide as defined in the ninth, eleventh and thirteenth aspects of the invention, or culturing a stable host cell line as defined in the seventeenth aspect of the invention.

We have also shown that the extracellular fragment of MR (residues 1-467, FIG. 2B, SEQ ID NO: 3, also known as the MR ectodomain) inhibits migration of endothelial cells, including bFGF and VEGF-induced migration.

Interestingly, the MR ectodomain does not appear to affect endothelial cell attachment (data not shown). The MR ectodomain, and fragments of it that show inhibitory activity in the HUVEC migration assay, would be predicted to be therapeutically useful in conditions in which unwanted, undesirable or inappropriate endothelial cell migration contributes to the pathology.

We have also shown that the MR ectodomain inhibits proliferation of endothelial cells. The MR ectodomain, and fragments of it that show anti-proliferative activity in an assay such as that described in Example 5, would be predicted to be therapeutically useful in conditions in which unwanted, undesirable or inappropriate endothelial cell proliferation contributes to the pathology.

A twenty-fourth aspect of the invention provides the MR ectodomain, or a fragment thereof that inhibits endothelial cell migration and/or proliferation.

It is appreciated that, in an embodiment, "a fragment of the MR ectodomain that inhibits endothelial cell migration and/or proliferation" may inhibit endothelial cell migration and not endothelial cell proliferation, or may inhibit endothelial cell proliferation and not endothelial cell migration. In an alternative embodiment, "a fragment of the MR ectodomain that inhibits endothelial cell migration and/or proliferation" may inhibit both endothelial cell migration and endothelial cell proliferation. In this embodiment, the fragment of the MR ectodomain does not necessarily inhibit both endothelial cell migration and/or proliferation to the same extent.

By "inhibiting endothelial cell migration and/or proliferation" we include the meaning of reducing the rate or level of endothelial cell migration and/or proliferation. The reduction can be a low level reduction of about 10%, or about 20%, or about 30%, or about 40% of the rate or level of endothelial cell migration and/or proliferation. Preferably, the reduction is a medium level reduction of about 50%, or about 60%, or about 70%, or about 80% reduction of the rate or level of endothelial cell migration and/or proliferation. More preferably, the reduction is a high level reduction of about 90%, or about 95%, or about 99%, or about 99.9%, or about 99.99% of the rate or level of endothelial cell migration and/or proliferation. Most preferably, inhibition can also include the elimination of endothelial cell migration and/or proliferation, or its reduction to an undetectable level.

Methods and assays for determining the rate or level of endothelial cell migration, and hence for determining whether and to what extent any particular fragment of the MR ectodomain inhibits endothelial cell migration, are known in the art and include the HUVEC assay described in Example 4. Similarly, methods and assays for determining the rate or level of endothelial cell proliferation, and hence for determining whether and to what extent any particular fragment of the MR ectodomain inhibits endothelial cell proliferation, are well known in the art and include the HUVEC assay described in Example 5.

By "a fragment of the MR ectodomain that inhibits endothelial cell migration and/or proliferation" we include the MR ectodomain that has been truncated or deleted, or a polypeptide comprising at least 450 contiguous amino acid residues of the MR ectodomain, which is sufficient to inhibit endothelial cell migration and/or proliferation. More preferably, a fragment of the ectodomain which is sufficient to inhibit endothelial cell migration and/or proliferation comprises at least 400, or at least 350, or at least 300, or at least 250, or at least 200, or at least 150, or at least 100, or at least 90, or at least 80, or at least 70, or at least 60, or at least 50, or at least 40, or at least 30, or at least 20, or at least 15, or at least 10 contiguous amino acid residues of the MR ectodomain. It is more particularly preferred if the fragment of the ectodomain which is sufficient to inhibit endothelial cell migration and/or proliferation comprises at least 60 contiguous amino acid residues of the MR ectodomain. The inhibition of endothelial cell migration and/or proliferation can be tested, for example, using the HUVEC assays as described in Examples 4 and 5.

In an embodiment, the fragment of the ectodomain which is sufficient to inhibit endothelial cell migration and/or proliferation consists of or comprises the Ig region of MR (residues 46-209, SEQ ID NO: 4).

In another embodiment, the fragment of the ectodomain which is sufficient to inhibit endothelial cell migration and/or proliferation consists of or comprises the IgA domain of MR (residues 46-116, SEQ ID NO: 5) or the IgB domain of MR (residues 151-209, SEQ ID NO: 6).

We have shown that the MR ectodomain does not appear to inhibit endothelial cell attachment (data not shown) and, preferably, the fragment of the ectodomain which is sufficient to inhibit endothelial cell migration and/or proliferation does not inhibit endothelial cell attachment.

Thus the MR ectodomain, or fragment thereof which inhibits endothelial cell migration, can be used to inhibit endothelial cell migration and/or proliferation without inhibiting endothelial cell attachment.

A twenty-fifth aspect of the invention provides the MR ectodomain, or a fragment thereof that inhibits endothelial cell migration and/or proliferation, for use in medicine.

A twenty-sixth aspect of the invention provides a method of combating any disease or condition involving unwanted, undesirable or inappropriate endothelial cell migration and/or proliferation in an individual, the method comprising administering the MR ectodomain, or a fragment thereof that inhibits endothelial cell migration and/or proliferation, to the individual.

Thus, the invention includes a method of treating a patient who has a disease or condition in which endothelial cell migration and/or proliferation contributes to the pathology, the method comprising the step of administering to the patient the MR ectodomain, or a fragment thereof that inhibits endothelial cell migration and/or proliferation.

A twenty-seventh aspect of the invention provides the use of the MR ectodomain, or a fragment thereof that inhibits endothelial cell migration and/or proliferation, in the preparation of a medicament for combating any disease or condition involving unwanted, undesirable or inappropriate endothelial cell migration and/or proliferation.

It has been shown that adipose tissue mass can be regulated by its vasculature (Rupnick, M. A. et al (2002) *PNAS USA* 99(16): 10730-10735). Furthermore, leptin, a known regulator of appetite and metabolism, is also known to modulate both migration of endothelial cells (Goetze, S. et al (2002) *Hypertension* 40(5): 748-754) and angiogenesis (Sierra-Honigmann, M. R. et al (1998) *Science* 281: 1683). Hence inhibition of migration of endothelial cells may reduce adipose tissue mass and be useful in treating obesity.

Diseases or conditions involving unwanted, undesirable or inappropriate endothelial cell migration and/or proliferation include tumours/cancer, psoriasis, atherosclerosis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation.

The invention thus includes a method of combating a disease or condition selected from tumours/cancer, psoriasis, atherosclerosis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation in an individual, the method comprising administering the MR ectodomain, or a fragment thereof that inhibits endothelial cell migration and/or proliferation, to the individual.

The invention also includes the use of the MR ectodomain, or a fragment thereof that inhibits endothelial cell migration and/or proliferation, in the preparation of a medicament for combating a disease or condition selected from tumours/cancer, psoriasis, atherosclerosis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation in an individual.

A yet further aspect of the invention provides an in vitro method of inhibiting endothelial cell migration and/or proliferation comprising administering the MR ectodomain, or a fragment thereof that inhibits endothelial cell migration and/or proliferation, to tissue or cells in vitro. The cells may be established cell lines, or cells that have been removed from an individual. The tissue or cells are preferably mammalian tissue or cells, and most preferably are human tissue or cells.

Furthermore, it is appreciated that administration of nucleic acid encoding the extracellular fragment of MR or active fragments thereof, might also be therapeutically useful.

A further aspect of the invention provides a polynucleotide encoding the MR ectodomain, or a fragment thereof that inhibits endothelial cell migration and/or proliferation, for use in medicine.

A further aspect of the invention thus provides a method of combating any disease or condition involving unwanted, undesirable or inappropriate endothelial cell migration and/or proliferation in an individual comprising administering a polynucleotide encoding the MR ectodomain, or a fragment thereof that inhibits endothelial cell migration and/or proliferation, to the individual.

A still further aspect of the invention provides the use of a polynucleotide encoding the MR ectodomain, or a fragment thereof that inhibits endothelial cell migration and/or proliferation, in the preparation of a medicament for combating any disease or condition involving unwanted, undesirable or inappropriate endothelial cell migration and/or proliferation.

A yet further aspect of the invention provides an in vitro method of inhibiting endothelial cell migration and/or proliferation comprising administering a polynucleotide encoding the MR ectodomain, or a fragment thereof that inhibits endothelial cell migration and/or proliferation, to tissue or cells in vitro. The cells may be established cell lines, or cells that have been removed from an individual. The tissue or cells are preferably mammalian tissue or cells, and most preferably are human tissue or cells.

An additional aspect of the invention provides a vector comprising a polynucleotide that encodes the MR ectodomain, or a fragment thereof that inhibits endothelial cell migration and/or proliferation. The invention also includes a host cell comprising a polynucleotide that encodes the MR ectodomain, or a fragment thereof that inhibits endothelial cell migration and/or proliferation, or a vector comprising such a polynucleotide.

A further aspect of the invention provides a pharmaceutical composition comprising the MR ectodomain, or a fragment thereof that inhibits endothelial cell migration and/or proliferation, or a polynucleotide encoding the MR ectodomain or the fragment thereof, and a pharmaceutically acceptable carrier.

Preferably, the pharmaceutical composition is suitable for intravenous administration to a patient.

The preferences for pharmaceutical formulations, routes of administration, vectors, cell lines and so on, are the same in the aspects of the invention directed to inhibiting endothelial cell migration and/or proliferation using the MR ectodomain or a fragment thereof as the preferences described above for the aspects of the invention directed to anti-MR antibodies.

We have also shown that the MR ectodomain is sufficient to inhibit formation of vessel sprouts in vitro in the aortic ring assay, and in vivo in the sponge angiogenesis assay, and would be predicted to be therapeutically useful in the inhibition of angiogenesis. Furthermore, fragments (for example ones made recombinantly or by de novo peptide synthesis) of the extracellular region of MR that show inhibitory activity in the rat aortic ring assay or the sponge angiogenesis assay would also be predicted to be useful in the inhibition of angiogenesis.

A further aspect of the invention thus provides a method of inhibiting angiogenesis in an individual in need thereof comprising administering the MR ectodomain, or a fragment thereof that inhibits angiogenesis, to the individual.

By "a fragment of the MR ectodomain that inhibits angiogenesis" we include the MR ectodomain that has been truncated or deleted, or a polypeptide comprising at least 450 contiguous amino acid residues of the MR ectodomain, which is sufficient to inhibit angiogenesis. More preferably, a fragment of the ectodomain which is sufficient to inhibit angiogenesis comprises at least 400, or at least 350, or at least 300, or at least 250, or at least 200, or at least 150, or at least 100, or at least 90, or at least 80, or at least 70, or at least 60, or at least 50, or at least 40, or at least 30, or at least 20, or at least 15, or at least 10 contiguous amino acid residues of the MR ectodomain. It is more particularly preferred if the fragment of the ectodomain which is sufficient to inhibit angiogenesis comprises at least 60 contiguous amino acid residues of the MR ectodomain. The inhibition of angiogenesis can be tested, for example, using the aortic ring assay as described in Example 2 or the sponge angiogenesis assay as described in Example 3.

In an embodiment, the fragment of the ectodomain which is sufficient to inhibit angiogenesis consists of or comprises the Ig region of MR (residues 46-209, SEQ ID NO: 4).

In another embodiment, the fragment of the ectodomain which is sufficient to inhibit angiogenesis consists of or comprises the IgA domain of MR (residues 46-116, SEQ ID NO: 5) or the IgB domain of MR (residues 151-209, SEQ ID NO: 6).

Another aspect of the invention provides the MR ectodomain, or a fragment thereof that inhibits angiogenesis.

A further aspect of the invention provides the MR ectodomain, or a fragment thereof that inhibits angiogenesis, for use in medicine.

A still further aspect of the invention provides the use of the MR ectodomain, or a fragment thereof that inhibits angiogenesis, in the preparation of a medicament for inhibiting angiogenesis.

A yet further aspect of the invention provides an in vitro method of inhibiting angiogenesis comprising administering the MR ectodomain, or a fragment thereof that inhibits angiogenesis, to tissue or cells in vitro.

Furthermore, it is appreciated that administration of nucleic acid encoding the extracellular fragment of MR or active fragments thereof, would also be a useful mode of anti-angiogenesis therapy.

A further aspect of the invention thus provides a method of inhibiting angiogenesis in an individual in need thereof comprising administering a polynucleotide encoding the MR ectodomain, or a fragment thereof that inhibits angiogenesis.

A further aspect of the invention provides a polynucleotide encoding the MR ectodomain, or a fragment thereof that inhibits angiogenesis, for use in medicine.

A still further aspect of the invention provides the use of a polynucleotide encoding the MR ectodomain, or a fragment thereof that inhibits angiogenesis, in the preparation of a medicament for inhibiting angiogenesis.

A yet further aspect of the invention provides an in vitro method of inhibiting angiogenesis comprising administering a polynucleotide encoding the MR ectodomain, or a fragment thereof that inhibits angiogenesis, to tissue or cells in vitro.

An additional aspect of the invention provides a vector comprising a polynucleotide that encodes the MR ectodomain, or a fragment thereof that inhibits angiogenesis.

Another aspect of the invention provides a host cell comprising a polynucleotide that encodes the MR ectodomain, or a fragment thereof that inhibits angiogenesis, or a vector comprising such a polynucleotide.

A further aspect of the invention provides a pharmaceutical composition comprising the MR ectodomain, or a fragment thereof that inhibits angiogenesis, or a polynucleotide encoding the MR ectodomain or the fragment thereof, and a pharmaceutically acceptable carrier.

Preferably, the pharmaceutical composition is suitable for intravenous administration to a patient.

The preferences for diseases or conditions to be combated, pharmaceutical formulations, routes of administration, vectors, cell lines and so on, are the same in the aspects of the invention directed to the MR ectodomain, or a fragment thereof that inhibits angiogenesis, as the preferences described above for the aspects of the invention directed to anti-MR antibodies.

All of the documents referred to herein are incorporated herein, in their entirety, by reference.

The listing or discussion of a prior-published document in this specification should not necessarily be taken as an acknowledgement that the document is part of the state of the art or is common general knowledge

EXAMPLES

Example 1

Preparation of Antibodies

The cDNA constructs that were used were as described in Table 2:

TABLE 2

| Full length MR cDNA | FIG. 1 |
| MR ectodomain-Fc | FIG. 2 |
| MR IgA + B-Fc | FIG. 3 |
| MR IgA-Fc | FIG. 4 |

"Fc" refers to the Fc region of the pIG vector. It is human IgG constant domains hinge, CH1, CH2, within the ends of the vector (multiple cloning site and splice acceptor region included). The nucleotide sequence of the vector is:

```
                                              (SEQ ID NO: 31)
AAGCTTGATATCGAATTCTGCAGCCCGGGGGATCCGGAGGGAGGG

TGTCTGCTGGAAGCAGGCTCAGCGCTCCTGCCTGGACGCATCCGG

CTATGCAGCCCCAGTCCAGGGCAGCAAGGCAGGCCCCGTCTGCCTC

TTCACCCGGAGGCCTCTGCCCGCCCCACTCATGCTCAGGGAGAGGG

TCTTCTGGCTTTTTCCCCAGGCTCTGGGCAGGCACAGGCTAGGTGC

CCCTAACCCAGGCCCTGCACACAAAGGGGCAGGTGCTGGGCTCAG

ACCTGCCAAGAGCCATATCGGGAGGACCCTGCCCCTGACCTAAGC

CCACCCCAAAGGCCAAACTCTCCACTCCCTCAGCTCGGACACCTTC

TCTCCTCCCAGATTCCAGTAACTCCCAATCTTCTCTCTGCAGAGCCC

AAATCTTGTGACAAAACTCACACATGCCCACCGTGCCCAGGTAAGC

CAGCCCAGGCCTCGCCCTCCAGCTCAAGGCGGGACAGGTGCCCTA

GAGTAGCCTGCATCCAGGGACAGGCCCCAGCCGGGTGCTGACACG

TCCACCTCCATCTCTTCCTCAGCACCTCAACTCCTGGGGGACCGTC

AGTCTTCCTCTTCCCCCCAAAACCCAAGGACACCCTCATGATCTCC

CGGACCCCTGAGGTCACATGCGTGGTGGTGGACGTGAGCCACGAA

GACCCTGAGGTCAAGTTCAACTGGTACGTGGACGGCGTGGAGGTG
```

-continued
```
CATAATGCCAAGACAAAGCCGCGGGAGGAGCAGTACAACAGCACG

TACCGGGTGGTCAGCGTCCTCACCGTCCTGCACCAGGACTGGCTGA

ATGGCAAGGAGTACAAGTGCAAGGTCTCCAACAAAGCCCTCCCAG

CCCCCATCGAGAAAACCATCTCCAAAGCCAAAGGTGGGACCCGTG

GGGTGCGAGGGCCACATGGACAGAGGCCGGCTCGGCCCACCCTCT

GCCCTGAGAGTGACCGCTGTACCAACCTCTGTCCTACAGGGCAGCC

CCGAGAACCACAGGTGTACACCCTGCCCCCATCCCGCCATGACCTG

ACCAAGAACCAGGTCAGCCTGACCTGCCTGGTCAAAGGCTTCTATC

CCAGCGACATCGCCGTGGAGTGGGAGAGCAATGGGCAGCCGGAGA

ACAACTACAAGACCACGCCTCCCGTGCTGGACTCCGACGGCTCCTT

CTTCCTCTACAGCAAGCTCACCGTGGACAAGAGCAGGTGGCAGCA

GGGGAACGTCTTCTCATGCTCCGTGATGCATGAGGCTCTGCACAAC

CACTACACGCAGAAGAGCCTCTCCCTGTCTCCGGGTAAATGAGTGC

GACGGCCGGCAAGCCCCGCTCCCCGGGCTCTCGCGGTCGCACGACC

ATGCTTGGCACGTACCCCCTGTACATACTTCCCGGGCGCCCAGCAT

GGAAATAAAGCACCCAGCGCTGCCCTGGGCCCCTGCGAGACTGTG

ATGGTTCTTTCCACGGGTCACCCCGAGTCTGAGGCCTGAGTGGCAT

GAGGGAGGCAGCGGCCGCGACTCTAG.
```

Generation of plasmid vectors N1 and NH10 for generation of anti-MR antibodies using genetic immunisation was carried out as follows. The plasmid vectors N1 and NH10, encoding N1 (membrane bound) and NH10 (soluble), were generated as follows:

N1 was generated by removal of the full length MR pBluescript KS+ by a NotI digest. The product was cleaned from a gel and ligated into pcDNA3 (which had been digested with NonI).

NH10 was generated by amplifying the extracellular domain of MR using primers which incorporated a 5' HinDIII site and a 3' NotI site. This was ligated into a pcDNA3 vector which had been digested with the same enzymes.

Genetic immunisation of mice to generate anti-MR antibodies was carried out as follows:

The constructs N1 and NH10 were used to immunise mice from three different genetic background according to the method reported in (Boyle, J. S., A. Silva, et al (1997) "DNA immunization: induction of higher avidity antibody and effect of route on T cell cytotoxicity." *Proc Natl Acad Sci USA* 94(26): 14626-31). The mice were immunised with an intramuscular injection of 100 µg of endotoxin free plasmid once every two weeks. Following the immunisation with the DNA constructs, the mice were each injected with 200 µl of purified MR ectodomain intravenously as a final boost before harvesting the spleen for generating the hybridomas. Three different genetic strains of mice were tested for their ability to generate suitable immune response to genetic immunisation, as shown in Table 3.

TABLE 3

| Group | Immunisation with N1 | Immunisation with NH10 |
|---|---|---|
| Group B - Balb/c mice | B1-B5 | B6-B10 |
| Group C - C57Bl mice | C1-C5 | C6-C10 |
| Group M - MFI outbred mice | M1-M5 | M6-M10 |

The schedule for immunisation is shown in Table 4.

TABLE 4

|  | Day |
| --- | --- |
| Pre Bleed | −2 |
| 1st Immunisation I/M | 0 |
| 2nd Immunisation I/M | 14 |
| 3rd Immunisation I/M | 28 |
| Test Bleed | 35 |
| I/V boost with cells or protein 200 µl of 129 µg/ml purified ECSM4 protein I/V in PBSa | 59 |
| Sacrifice the mice and remove spleens for fusion. | 63 |

During the course of immunisation, the test bleed were assayed for anti-MR antibodies using the following capture ELISA. This ELISA is a robust and flexible assay which can be used to measure level of fusion protein in supernatant or presence/level of antibody to the fusion protein in hybridoma supernatant. It is very sensitive, detecting human IgG in the range 0.001 to 0.5 µg/ml. It has a low background, typically in the region of OD405=0.07. In comparison, neat hybridoma supernatants in this system (MR-pIG) give positive results of OD405>1.0 (and in some cases >2.0).

Summary of ELISA Method

Coat plate with 5 µg/ml goat anti-human IgG Fc-specific; block with 1% BSA in PBS; add fusion protein supernatant or human IgG control; add detection antibody or goat anti human alkaline phosphatase conjugate; add secondary conjugate if unconjugated detection antibody used; add pNPP substrate; stop with 3M NaOH after 20-30 min.

Detailed Protocol for Capture ELISA for pIG Fusion Proteins (1) Coat plate with 2 to 5 µg/ml goat-anti-human IgG (Fc-specific) purified unconjugated antibody diluted in PBS, e.g. Sigma I-2136. 50 µl/well, tap plate gently to ensure even coverage of base of wells.

(2) Incubate overnight at +4° C. Plates can be stored like this for at least a week, as long as they are kept in a humidified container to prevent drying out.

(3) Wash 3× with PBS-Tween 20 (0.04% Tween 20) by flooding plate and tapping dry on tissue paper each time.

(4) Block with 1% BSA in PBS, 200 µl/well. Incubate at room temperature for 1-2 hours, or overnight at +4° C. Plates can be stored blocked at +4° C., as for point (2) above.

(5) Repeat wash step (step 3).

(6) Coat plate with the fusion protein supernatant e.g. MR-ecto-pIG. Supernatant containing 0.5 to 1.0 µg/ml fusion protein gives a very strong result, so there is no need to purify or concentrate. Incubate 1 hour at room temperature. Human IgG can be used instead of supernatant as a positive control for detecting the Fc domain and titrated for quantifying the amount of NABA-pIG fusion protein present in the supernatant.

(7) Repeat wash step (step 3)

(8) Detect the pIG domain using goat anti-human IgG-alkaline phosphatase conjugate, 1/5000 dilution in PBS (positive control), or mouse serum from test bleed, various dilutions in PBS (1/10 to 1/1000). Incubate 1 hour at room temperature. This is followed by an additional step of a secondary conjugate (anti-mouse-alkaline phosphatase). Incubate for a further 1 hour at room temperature.

(9) Repeat wash step (step 3). (Also between use of detection antibody and secondary conjugate, if alternative method used)

(10) Measure colour change using Sigma pNPP substrate made up from tablets, 50 µl/well. Incubate for 20-30 min. in the dark then stop the reaction by the addition of 50 µl/well 3M NaOH. Read the colour change at 405 nm.

Anti-MR antibodies were generated as follows: The spleens harvested from the above mentioned immunised mice were fused to NSO cells. The resulting hybridomas were tested for their ability generate antibodies that recognise MR using ELISA. Of the antibodies identified, one was chosen for further studies –MR7.

The Mr7 Antibody was Characterised as Follows:

MR7 was tested for its ability to recognise various domains of MR using ELISA. It was found that MR7 recognises the MR IgA domain. The DNA sequence encoding the Complementary Determining Regions (CDRs) of MR7 was determined by PCR amplification and standard sequencing techniques using the primers shown below.

Primers

A mixture of eleven 5' primers (listed in Table 5) was used to amplify the kappa chain CDRs.

TABLE 5

| Primer | Sequence |
| --- | --- |
| MKV1 | ACTAGTCGACATGAAGTTGCCTGTTAGGCTGTTGGTGCTG (SEQ ID NO: 32) |
| MKV2 | ACTAGTCGACATGGAGWCAGACACACTCCTGYTATGGGT (SEQ ID NO: 33) |
| MKV3 | ACTAGTCGACATGAGTGTGGCTCACTCAGGTCCTGGSGTTG (SEQ ID NO: 34) |
| MKV4 | ACTAGTCGACATGAGGRCCCCTGCTCAGWTTYTTGGMWTCTTG (SEQ ID NO: 35) |
| MKV5 | ACTAGTCGACATGGATTTWCAGGTGCAGATTWTCAGCTTC (SEQ ID NO: 36) |
| MKV6 | ACTAGTCGACATGAGGTKCCYTGYTCAGYTYCTGRGG (SEQ ID NO: 37) |
| MKV7 | ACTAGTCGACATGGGCWTCAAGATGGAGTCACAKWYYCWGG (SEQ ID NO: 38) |
| MKV8 | ACTAGTCGACATGTGGGGAYCTTKTTYAMMTTTTTCAATTG (SEQ ID NO: 39) |
| MKV9 | ACTAGTCGACATGGTRTCCWCASCTCAGTTCCTTG (SEQ ID NO: 40) |
| MKV10 | ACTAGTCGACATGTATATATGTTTGTTGTCTATTTCT (SEQ ID NO: 41) |
| MKV11 | ACTAGTCGACATGGAAGCCCCATGCTCAGCTTCTCTTCC (SEQ ID NO: 42) |

The primer sequence which amplified the MR7 kappa chain 5' end was MK5

The sequence of the 3' primer was GTTTGATCTA-GAGCTTGGTCCC (SEQ ID NO: 43) which amplifies from after CDR3 and adds an XbaI restriction site on the end of the product if you need to clone the product. The same product was also produced when the 5' mix was used with the 3' constant region primer TTGGAGGGCGTTATCCACCT (SEQ ID NO: 44).

Heavy Chain Primers

The 5' primer was:

ATCGGATCCAGGTSMARCTGCAGSAGTCWGG, (SEQ ID NO: 45)

and the 3' primer was:

(SEQ ID NO: 46)
CTCGAATTCTGAGGAGACGGTGACCGTGGTCCCTTGGCCCC.

The redundancy code for these primers is shown in Table 6.

TABLE 6

| IUB ambiguity code | | |
|---|---|---|
| Nucleotides | Code | |
| A + C | M | aMino |
| A + G | R | puRine |
| A + T | W | Weak |
| C + G | S | Strong |
| C + T | Y | pYrimidine |
| G + T | K | Keto |
| A + G + C | V | not T |
| A + C + T | H | not G |
| A + G + T | D | not C |
| C + G + T | B | not A |
| A + G + C + T | N | aNy |

MR7Sequence

The amino acid sequence of the light and heavy V regions of MR7 antibody is given below. The CDRs are underlined.

MR7 kappa V region:
(SEQ ID NO: 12)
QIVLTQSPALMSASPGEKVTMTC<u>SASSSVSYMY</u>WYQQKPRSSP KPWIY<u>LTSNLAS</u>GVPARFSGSGSGTSYSLTISSMEAEDAATYY C<u>QQWSSNPLT</u>FGAGTKLELK.

MR7 heavy V region:
(SEQ ID NOs: 16-17)
QVK/QLQESGPELVKPGASVKISCKASGYSLT<u>DYNLN</u>WVKQNKGKSLEWI G<u>VINPNYGTTSYNQKFKG</u>KATLTVDQSSSTTYMQLNSLTSEDSAVYYCAR <u>GRDYFGY</u>WGQGTTVTVSS, The nucleotide sequence encoding the light and heavy V regions of MR7 antibody. The CDRs are underlined.

MR7 kappa V region:
(SEQ ID NO: 21)
CAA,ATT,GTT,CTC,ACC,CAG,TCT,CCA,GCA,CTC,ATG,TCT, GCA,TCT,CCA,GGG,GAG,AAG,GTC,ACC,ATG,ACC,TGC,<u>AGT,</u>

<u>GCC,AGC,TCA,AGT,GTA,AGT,TAC,ATG,TAC,</u>TGG,TAC,CAG,

CAG,AAG,CCA,AGA,TCC,TCC,CCC,AAA,CCC,TGG,ATT,TAT,

<u>CTC,ACA,TCC,AAC,CTG,GCT,TCT,</u>GGA,GTC,CCT,GCT,CGC,

TTC,AGT,GGC,AGT,GGG,TCT,GGG,ACC,TCT,TAC,TCT,CTC,

ACA,ATC,AGC,AGC,ATG,GAG,GCT,GAA,GAT,GCT,GCC,ACT,

TAT,TAC,TGC,<u>CAG,CAG,TGG,AGT,AGT,AAC,CCA,CTC,ACG,</u>

TTC,GGT,GCT,GGG,ACC,AAG,CTG,GAG,CTG,AAA.

MR7 heavy V region:
(SEQ ID NOs: 25-27)
CAG,GTC,AAG(orA/CAA),CTG,CAG,GAG,TCA,GGA,CCT,GAG,

CTG,GTG,AAG,CCT,GGC,GCT,TCA,GTG,AAG,ATA,TCC,TGC,

AAG,GCT,TCT,GGT,TAC,TCA,CTC,ACT,<u>GAC,TAC,AAC,CTG,</u>

<u>AAC,</u>TGG,GTG,AAG,CAG,AAC,AAA,GGA,AAG,AGC,CTT,GAG,

-continued
TGG,ATT,GGA,<u>GTA,ATT,AAT,CCA,AAC,TAT,GGT,ACT,AGT,</u>

<u>TAC,AAT,CAG,AAG,TTC,AAG,GGC,</u>AAG,GCC,ACA,TTG,ACT,

GTA,GAC,CAA,TCT,TCC,AGC,ACA,ACC,TAC,ATG,CAG,CTC,

AAC,AGC,CTG,ACA,TCT,GAG,GAC,TCT,GCA,GTC,TAT,TAC,

TGT,GCA,AGA,<u>GGG,AGG,GAT,TAC,TTC,GGC,</u>TAC,TGG,GGC,

CAA,GGG,ACC,ACG,GTC,ACC,GTC,TCC,TCA.

Example 2

Figure 5:
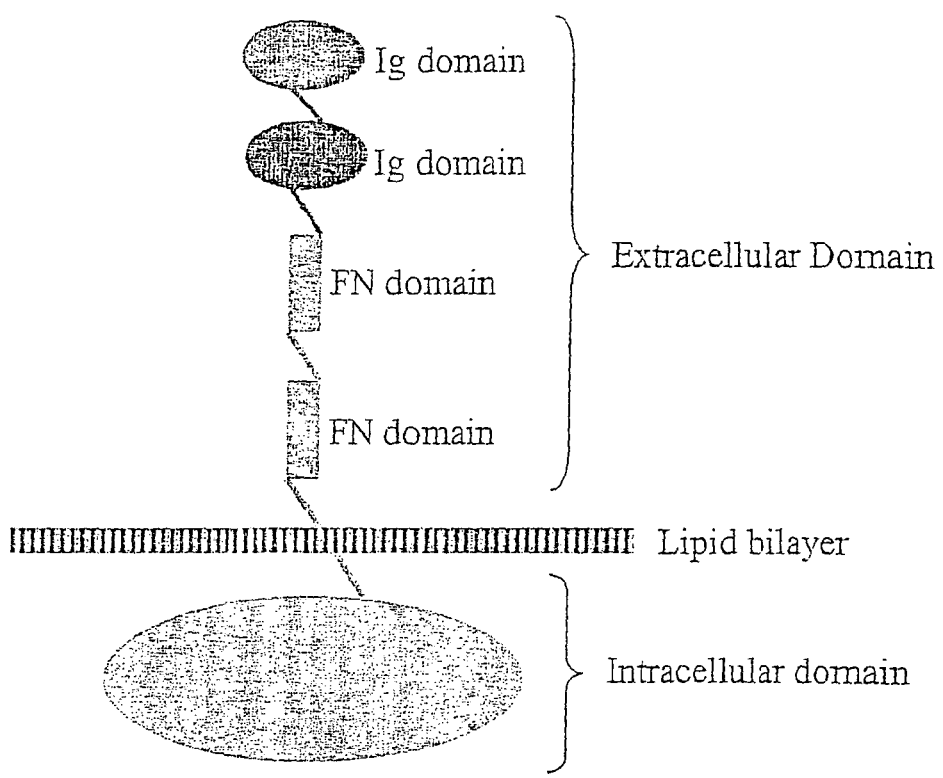
FIG. 5 shows a pictorial representation of the structure of MR.
Figure 6A:
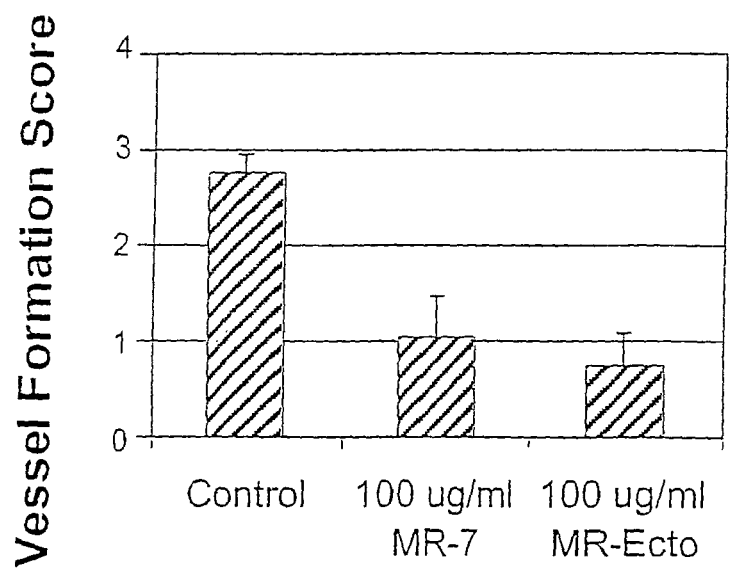
FIG. 6A is a graph and a table showing the effect of the antibody (MR-7) and the soluble extracellular domain of MR (MR Ecto) on formation of new vessels in the aortic ring assay.
Figure 6B:
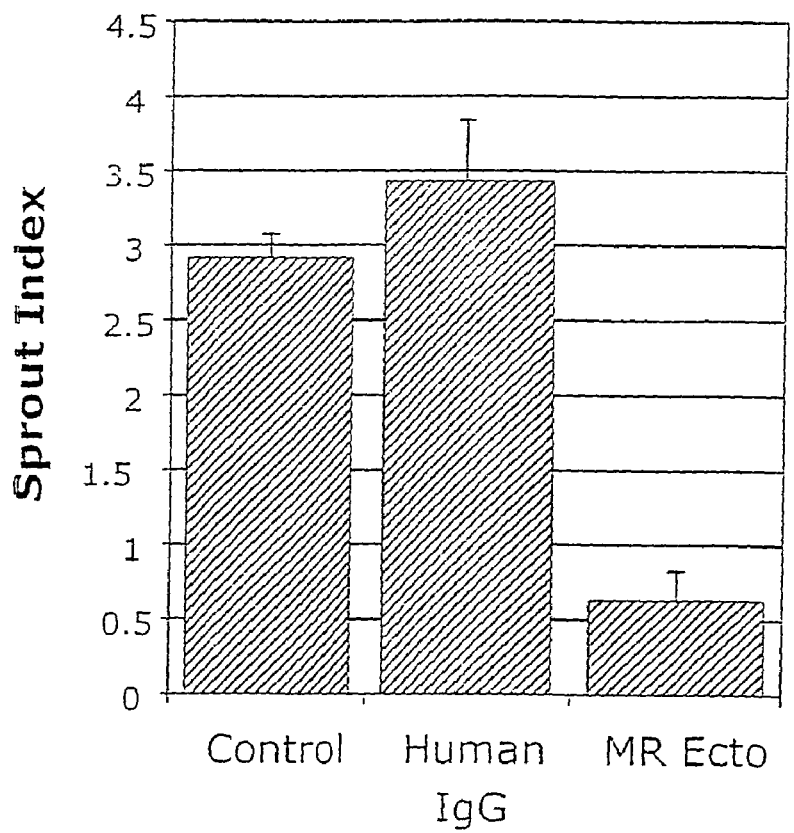
FIG. 6B is a graph and a table showing the effect of the soluble extracellular domain of MR (MR ectodomain, MR Ecto) on formation of new vessels in the aortic ring assay with a human IgG control.

The Antibody MR7 and the MR Ectodomain (Extracellular Fragment of MR Residues 1-467) Inhibit Formation of Vessel Sprouts in the Aortic Ring Assay Summary The role of MR in angiogenesis was investigated using the rat aortic ring assay. Segments of rat aorta were embedded in Matrigel and treated with either antibody MR7 or purified MR ectodomain protein. The sprouting vessels were allowed to develop over five day before scoring by three independent observers. The averaged scores over 20-25 separate experiments are shown in FIGS. 6A and 6B. Inter-scorer reliability was assessed using the method of Landis and Koch. The weighted kappa values calculated were 0.96 for MR7 and 0.93 for MR ectodomain. These kappa values show that there was a high degree of consistency between independent scorers.

Methods

Aortas were harvested from 200 g-300 g rats (6-8 weeks old) and immediately placed in MCDB 131 media. Connective tissue was removed and aortas cut into 1 mm-1.5 mm rings. 48-well plates were coated with 110 μl of Matrigel (BD Biosciences) diluted 1:1 with PBS and allowed to gel at 37° C. for 30 min. The rings were placed in the wells and sealed in place with an overlay of 40 μl of Matrigel. Antibodies (100 μg/ml) or MR ectodomain (soluble robo4 extracellular domain) (15 μg/ml) were added to wells in a final volume of 250 μl of MCDB 131 media containing 20% foetal bovine serum and 50 μg/ml endothelial cell growth supplement. Media was changed after two days and aortas analysed and photographed after five days.

Results

Representative photomicrographs of segments of the aortic rings are shown in FIGS. 7 A-C. As the figure shows, treatment of the aortic rings with either MR7 or MR ectodomain resulted in significant decrease in sprouting of vessels from the aortic segment.

Statistical Analysis of Aortic Ring Assay

Aortic rings were scored according to the vessel growth on a scale of 0 (low) to 4 (high) as follows: 0=no growth, 1=few vessels, 2=intermediate vessels, 3=many vessels but sporadic sprouting centres around the ring and 4=many vessels sprouting from all regions of the ring.

All experiments were scored blind by three independent researchers. Inter-scorer reliability was assessed using the method of Landis and Koch (*Biometrics*, 1977, 33(1), 159-174). Weighted kappa was calculated in order to establish the inter-rater reliability of the examiners. Weighted kappa is given by:

$$k_W = \frac{p_{o(w)} - p_{e(w)}}{1 - p_{e(w)}}$$

where $p_{o(w)}$ and $p_{e(w)}$ are the weighted observed and expected agreement calculated with the formulas:

$$p_o(w) = \frac{1}{n}\sum_{i=1}^{g}\sum_{j=1}^{g} w_{ij}f_{ij}$$

$$p_e(w) = \frac{1}{n^2}\sum_{i=1}^{g}\sum_{j=1}^{g} w_{ij}r_i c_j$$

The i represents the category for one examiner and j represent the category for the second examiner. The $r_i$ represents the grand total of cases in category i for one examiner, and $c_j$ represents the grand total of cases in category j for the other examiner.

The difference between the categories considered to be 1, therefore with the introduction of the new categories for the description of the additional transition categories the difference to one category to another was considered to be 0.5 points. The total number of categories therefore g=9. The number of cases is n=80.

The weight wij for the observed frequency fij of cases which were in category by one examiner and in category j for the second examiner is calculated as:

$$w_{ij} = 1 - \frac{|i-j|}{g-1}$$

The strength of the agreement was regarded as poor if the Kappa statistics was <0.00, slight for values 0.00-0.20, fair for 0.21-0.40, moderate for 0.41-0.60, substantial for 0.61-0.80 and high for 0.81-1.00.

The data was then collated together and analysed by ANOVA and the Kruskall Wallis method. The resulting p values show a highly significant difference between the control group and those treated with either MR7 or the ectodomain.

Example 3

The MR Ectodomain (Extracellular Fragment of MR Residues 1-467) Inhibits Formation of Vessel Sprouts In Vivo The ability of the MR ectodomain to inhibit angiogenesis in vivo was tested using a sponge angiogenesis assay (Hori Y. et al (1996) "Differential effects of angiostatic steroids and dexamethasone on angiogenesis and cytokine levels in rat sponge implants" *Br. J. Pharmacol.* 118(7): 1584-1591) performed on female C57 black mice. All mice received a subcutaneous sterile polyether sponge (type 611-9) disc (15×5×5 mm) under the dorsal skin at day 0. Test reagents were injected through the skin directly into the sponges every second day for 21 days (100 μl injection volume). Groups of 2 mice received either PBS control; 10 ng/ml basic fibroblast growth factor (bFGF); or 10 ng/ml bFGF+100 mg/ml MR ectodomain. Animals were scarified on day 21 and sponges were removed, fixed in 3.7% paraformaldeyde and paraffin embedded. 5 micron sections were stained with haematoxylin and eosin and digital photos taken using a Zeiss Axioskop 2 plus microscope with an Axiocam digital camera at 20× magnification. The number of vessels invading the sponges were counted as a measure of angiogenesis.

There were clear differences between the sponges from the mice who were injected with bFGF alone (controls) and those who were injected with both bFGF and the MR ectodomain. The differences were:
a) significantly fewer vessel numbers in the MR ectodomain treated sponges compared to control (FIG. 8; p=0.0014 using the Student t-test);
b) an absence of very large vessels from the MR ectodomain treated sponges; and
c) much lower fibroblast cell density in the MR ectodomain treated sponges.

Example 4

The MR Ectodomain (Extracellular Fragment of MR Residues 1-467) Inhibits Migration of Primary Human Vascular Endothelial Cells A primary human vascular endothelial cell (HUVEC) migration assay was performed using the BD BioCoat™ Angiogenesis System for Endothelial Cell Migration which is available as Catalog No. 354143 from BD Biosciences, Bedford, Mass., USA. Instructions for using this kit can be found at the BD Biosciences website. This system uses a 24-multi-well insert system and consists of a BD Falcon FluoroBlok PET membrane with 3 micron pore size coated uniformly on the top side with fibronectin. Quantitation of cell migration is achieved by post-labelling of cells with the fluorescent dye Calcein AM and measuring the fluorescence of migrating cells in a fluorescence plate reader. The FluoroBlok membrane effectively blocks the passage of light from 490-700 nm at >99% efficiency meaning labelled cells that have not migrated are blocked from detection.

The upper chamber was seeded with 50,000 HUVEC/well in MCDB 131 medium supplemented with 1% heat-inactivated foetal calf serum (FCS). The bottom chambers were loaded with or without bFGF (5 ng/ml), VEGF (10 ng/ml) and MR ectodomain (100 μg/ml) in 750 μl of MCDB 131+1% FCS. After 22 hr incubation at 37° C. the insert membranes were stained with 4 μg/ml Calcein AM (Molecular Probes) in Hanks Balanced Salt Solution (HBSS) for 90 min. Fluorescence on the bottom side of the membrane was measured at excitation/emission wavelengths of 485/530 nm. Images were taken using a Zeiss Axiovert 135 microscope with an Axiocam digital camera at 10× magnification. Both bFGF and VEGF are known to stimulate migration of endothelial cells (Cross & Claesson-Welsh, 2001 *Trends Pharmacol Sci.* 22(4): 201-207). As shown in FIGS. 9A and 9B, the MR ectodomain was shown to significantly inhibit migration of HUVEC cells induced by either bFGF or VEGF.

Example 5

The MR Ectodomain (Extracellular Fragment of MR Residues 1-467) Inhibits Endothelial Cell Proliferation $5\times10^4$ primary human vascular endothelial cells (HUVEC) were seeded per well of a 6-well plate in 1.5 ml full growth media containing treatment (6.25, 12.5, 25, 50 or 100 μg/ml of the MR ectodomain (Robo4-Fc) or 100 mg/ml human IgG), or no treatment as a control. After four days incubation at 37° C., the cells were washed in PBS and detached from the wells by addition of 1 ml trypsin solution. After all the cells had detached, 400 μl of the cell suspension was transferred to 19.6 ml Isoton buffer (Beckman Coulter), and the number of cells in each sample was determined in a Coulter Particle Count and Size Analyser (Beckman Coulter). The experiment was carried out in triplicate, and replicated three times.

As shown in FIG. 10, incubation in the presence of 12.5 µg/ml MR ectodomain decreased proliferation of the HUVEC cells to about 75% of the control levels, and higher concentrations of MR ectodomain had an increasingly strong anti-proliferative effect.

Example 6

Treatment of a Patient Exhibiting Undesirable Angiogenesis by Administering an Antibody that Specifically Binds to the Extracellular Region of MR A patient exhibiting undesirable angiogenesis is treated with intravenous infusions of saline solutions of a pharmaceutical composition comprising an antibody that specifically binds to the extracellular region of MR. The infusions are administered weekly for a time of 3 to 6 months.

Example 7

Treatment of a Patient Exhibiting Undesirable Angiogenesis by Administering the Extracellular Region of MR A patient exhibiting undesirable angiogenesis is treated with intravenous infusions of saline solutions of a pharmaceutical composition comprising the MR ectodomain. The infusions are administered weekly, typically for 3 to 6 months.

We claim:

1. An isolated antibody having at least one light chain variable region comprising the following CDRs:

```
CDR1:
SASSSVSYMY;        (SEQ ID NO: 9)

CDR2:
LTSNLAS;           (SEQ ID NO: 10)
and

CDR3:
QQWSSNPLT;         (SEQ ID NO: 11)
and
``` the antibody having at least one heavy chain variable region comprising the following CDRs:

```
CDR1:
DYNLN;             (SEQ ID NO: 13)

CDR2:
VINPNYGTTSYNQKFKG; (SEQ ID NO: 14)
and

CDR3:
GRDYFGY.           (SEQ ID NO: 15)
```

2. An isolated antibody that selectively binds to the magic roundabout (MR) epitope bound by an antibody according to claim 1, having at least one kappa light chain variable region comprising:

the amino acid sequence Q I V L T Q S P A L M S A S P G E K V T M T C S A S S S V S Y M Y W Y Q Q K P R S S P K P W I Y L T S N L A S G V P A R F S G S G S G T S Y S L T I S S M E A E D A A T Y Y C Q Q W S S N P L T F G A G T K L E L K (SEQ ID NO:12); and at least one heavy chain variable region comprising the amino acid sequence Q V K L Q E S G P E L V K P G A S V K I S C K A S G Y S L T D Y N L N W V K Q N K G K S L E W I G V I N P N Y G T T S Y N Q K F K G K A T L T V D Q S S S T T Y M Q L N S L T S E D S A V Y Y C A R G R D Y E G Y W G Q G T T V T V S S (SEQ ID NO 16) or Q V Q L Q E S G P E L V K P G A S V K I S C K A S G Y S L T D Y N L N W V K Q N K G K S L E W I G V I N P N Y G T T S Y N Q K F K G K A T L T V D Q S S S T T Y M Q L N S L T S E D S A V Y Y C A R G R D Y F G Y W G Q G T T V T V S S (SEQ ID NO:17).

3. A compound comprising an antibody according to claim 1 and a detectable moiety.

4. A compound according to claim 3 wherein the detectable moiety comprises a suitable amount of any one of iodine-123, iodine-131, indium-111, fluorine-19, carbon-13, nitrogen-15, oxygen-17, technetium-99m, gadolinium, manganese or iron.

5. An isolated monoclonal antibody that selectively binds the Ig region of magic roundabout (MR) (corresponding to amino acid residues 46-209, set forth herein as SEQ ID NO: 4) but does not selectively bind to the peptide LLQP-PARGHAHDGQALSTDL (SEQ ID NO: 28).

6. A compound comprising a monoclonal antibody according to claim 5 and a detectable moiety.

7. A compound according to claim 6 wherein the detectable moiety comprises a suitable amount of any one of iodine-123, iodine-131, indium-111, fluorine-19, carbon-13, nitrogen-15, oxygen-17, technetium-99m, gadolinium, manganese or iron.

8. An isolated monoclonal antibody that selectively binds the IgA region of MR (corresponding to amino acid residues 46-116, set forth herein as SEQ ID NO: 5) but does not selectively bind to the peptide LLQPPARGHAHDGQAL-STDL (SEQ ID NO: 28).

9. A compound comprising a monoclonal antibody according to claim 8 and a detectable moiety.

10. A compound according to claim 9 wherein the detectable moiety comprises a suitable amount of any one of iodine-123, iodine-131, indium-111, fluorine-19, carbon-13, nitrogen-15, oxygen-17, technetium-99m, gadolinium, manganese or iron.

11. An isolated monoclonal antibody that selectively binds the IgB region of MR (corresponding to amino acid residues 151-209, set forth herein as SEQ ID NO: 6).

12. A compound comprising a monoclonal antibody according to claim 11 and a detectable moiety.

13. A compound according to claim 12 wherein the detectable moiety comprises a suitable amount of any one of iodine-123, iodine-131, indium-111, fluorine-19, carbon-13, nitrogen-15, oxygen-17, technetium-99m, gadolinium, manganese or iron.

* * * * *